(12) United States Patent
Usui et al.

(10) Patent No.: US 9,309,221 B2
(45) Date of Patent: Apr. 12, 2016

(54) 1-SUBSTITUTED INDAZOLE DERIVATIVE

(71) Applicant: Dainippon Sumitomo Pharma Co., Ltd., Osaka (JP)

(72) Inventors: Shinya Usui, Osaka (JP); Hiroki Yamaguchi, Osaka (JP); Yoko Nakai, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 14/128,516

(22) PCT Filed: Apr. 9, 2013

(86) PCT No.: PCT/JP2013/060744
§ 371 (c)(1),
(2) Date: Dec. 20, 2013

(87) PCT Pub. No.: WO2013/154109
PCT Pub. Date: Oct. 17, 2013

(65) Prior Publication Data
US 2015/0031681 A1    Jan. 29, 2015

(30) Foreign Application Priority Data
Apr. 10, 2012    (JP) .................................. 2012-089057

(51) Int. Cl.
| | |
|---|---|
| *C07D 401/04* | (2006.01) |
| *A61K 31/445* | (2006.01) |
| *C07D 401/14* | (2006.01) |
| *C07D 405/14* | (2006.01) |
| *C07D 231/56* | (2006.01) |
| *C07D 405/12* | (2006.01) |
| *C07D 471/04* | (2006.01) |
| *C12N 15/00* | (2006.01) |
| *A61K 31/416* | (2006.01) |
| *A61K 31/439* | (2006.01) |
| *A61K 31/454* | (2006.01) |
| *A61K 31/4545* | (2006.01) |
| *A61K 31/501* | (2006.01) |
| *A61K 31/55* | (2006.01) |
| *A61K 45/06* | (2006.01) |
| *C07D 403/04* | (2006.01) |

(52) U.S. Cl.
CPC ............ *C07D 401/04* (2013.01); *A61K 31/416* (2013.01); *A61K 31/439* (2013.01); *A61K 31/454* (2013.01); *A61K 31/4545* (2013.01); *A61K 31/501* (2013.01); *A61K 31/55* (2013.01); *A61K 45/06* (2013.01); *C07D 231/56* (2013.01); *C07D 401/14* (2013.01); *C07D 403/04* (2013.01); *C07D 405/12* (2013.01); *C07D 405/14* (2013.01); *C07D 471/04* (2013.01); *C12N 15/00* (2013.01)

(58) Field of Classification Search
CPC .. C07D 401/04; C07D 401/14; A61K 31/445; A61K 31/4545
USPC ............. 514/318, 322, 403; 546/133 M, 194, 546/199, 133; 548/361.1
See application file for complete search history.

(56) References Cited

U.S. PATENT DOCUMENTS

| 8,765,786 B2 | 7/2014 | Usui et al. ...................... 514/322 |
|---|---|---|
| 9,051,295 B2 | 6/2015 | Usui et al. ...................... 514/322 |

(Continued)

FOREIGN PATENT DOCUMENTS

| WO | WO 96/41803 | 12/1996 |
|---|---|---|
| WO | WO 03/024942 | 3/2003 |

(Continued)

OTHER PUBLICATIONS

Dowskin et al. "Competitive neuronal . . ." J. Pharm. Exp. Therap. v/ 298(2) 395-402 (2001).*

(Continued)

*Primary Examiner* — Celia Chang
(74) *Attorney, Agent, or Firm* — Fish & Richardson P.C.

(57) ABSTRACT

A medicament for treating diseases associated with cholinergic properties in the central nervous system (CNS) and/or peripheral nervous system (PNS), diseases associated with smooth muscle contraction, endocrine disorders, neurodegenerative disorders and the like, which comprises a compound of Formula (I):

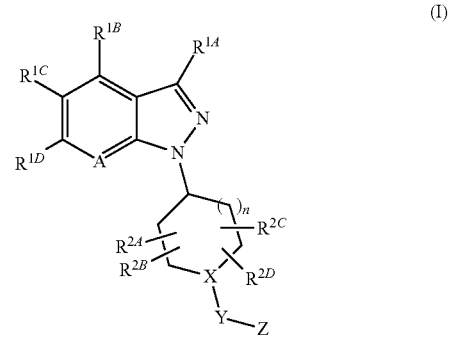

wherein A is $CR^{1E}$ or a nitrogen atom, X—Y—Z is N—CO—$NR^{3A}R^{3B}$ and the like, $R^{1A}$ to $R^{1E}$ are each independently a hydrogen atom and the like, $R^{2A}$ to $R^{2D}$ are each independently a hydrogen atom and the like, $R^{3A}$ and $R^{3B}$ are each independently an optionally-substituted $C_{3-10}$ cycloalkyl and the like, and n is 1 or 2
or a pharmaceutically acceptable salt thereof, which exhibits potent modulatory-effects on the activity of α7 nicotinic acetylcholine receptor (α7 nAChR).

12 Claims, No Drawings

(56) References Cited

U.S. PATENT DOCUMENTS

| | | | |
|---|---|---|---|
| 2009/0088418 A1 | 4/2009 | Pfister et al. | |
| 2014/0121243 A1 | 5/2014 | Usui et al. | 514/322 |
| 2014/0121244 A1 | 5/2014 | Usui et al. | 514/322 |
| 2014/0364393 A1 | 12/2014 | Yang et al. | 514/63 |

FOREIGN PATENT DOCUMENTS

| | | |
|---|---|---|
| WO | WO 03/093250 | 11/2003 |
| WO | WO 2005/073219 | 8/2005 |
| WO | WO 2006/138510 | 12/2006 |
| WO | WO 2007/030366 | 3/2007 |
| WO | WO 2007/102883 | 9/2007 |
| WO | WO 2008/157404 | 12/2008 |
| WO | WO 2009/001132 | 12/2008 |
| WO | WO 2009/046025 | 4/2009 |
| WO | WO 2009/088103 | 7/2009 |
| WO | WO 2010/032009 | 3/2010 |
| WO | WO 2011/035159 | 3/2011 |
| WO | WO 2011/051282 | 5/2011 |
| WO | WO 2012/068106 | 5/2012 |
| WO | WO 2012/118812 | 9/2012 |
| WO | WO 2012/133509 | 10/2012 |
| WO | WO 2012/176763 | 12/2012 |
| WO | WO 2013/085954 | 6/2013 |

OTHER PUBLICATIONS

Edink "Structure-based design . . . " p. 1-34 (2011).*
CNS Wikipedia p. 1-8 (2015).*
Silverman "The organic chemistry of drug . . . " -.65-73 (1993).*
Yang et al. "{re[aratopm pf sibstotited . . . " CA159:922769 (2013).*
Improper Markush Fed. Reg. V. 76 p. 7162-7175, slide 1, 64-67 (2011).*
International Search Report in International Application No. PCT/JP2013/060744, mailed May 14, 2013, 5 pages.
Arnautu et al., "Sonogashira cross-coupling reaction of 3-iodoindazoles with various terminal alkynes: a mild and flexible strategy to design 2-aza tryptamines," Tetrahedron Lett., 2002, 43:2695-2697.
Bhuiyan et al., "Synthesis of Symmetric Diester-Functionalised Tröger's Base Analogues," Eur J Org. Chem., 2010, 24:4662-4670.
Crestey et al., "A new and efficient synthesis of 2-azatryptophans," Tetrahedron, 2006, 62:7772-7775.
Cui et al., "Non-covalent thrombin inhibitors featuring P3-Heterocycles with P1-Bicyclic arginine surrogates," Bioorg. Medicinal Chem. Lett., 2002, 12 (20):2925-2930.
Fussell et al., "A three-step synthesis of 4-(4-iodo-1H-pyrazol-1-yl)piperidine, a key intermediate in the synthesis of Crizotinib," Tetrahedron Lett., 2012, 53:948-951.
Mastalerz et al., "New C-5 substituted pyrrolotriazine dual inhibitors of EGFR and HER2 protein tyrosine kinases," Bioorg. Medicinal Chem. Lett., 2007, 17(7):2036-2042.
Pelleter and Renaud, "Facile, Fast and Safe Process Development of Nitration and Bromination Reactions Using Continuous Flow Reactors," Org. Process Res & Dev., 2009, 13(4):698-705.
Randall, and Duval "Regioselective O-Alkylations of Indazolinone Using (Cyanomethylene)triphenylphosphorane," Synlett., 2009, 16:2673-2675.
Yoshino et al., "Organic Field-effect Transistors Based on Solution-processible Dibenzotetrathiafulvalene Derivatives," Chem. Lett., 2009, 38(3):200-201.
Sharma et al., "Deuterium Isotope Effects on Drug Pharmacokinetics. I. System—Dependent Effects of Specific Deuteration with Aldehyde Oxidase Cleared Drugs," *Drug Metabolism and Disposition*, 2012, 40(3):625-634.
Supplementary European Search Report in European Application No. 13774975.0, dated Dec. 4, 2015, 6 pages.

* cited by examiner

SEQUENCE LISTING

<160> NUMBER OF SEQ ID NOS: 1

<210> SEQ ID NO 1
<211> LENGTH: 1514

```
<212> TYPE: DNA
<213> ORGANISM: homo sapience
<220> FEATURE:
<223> OTHER INFORMATION: Human alpha7 nAChR gene

<400> SEQUENCE: 1
ccaccatgcg ctgctcgccg ggaggcgtct ggctggcgct ggccgcgtcg ctcctgcacg      60
tgtccctgca aggcgagttc cagaggaagc tttacaagga gctggtcaag aactacaatc     120
ccttggagag gcccgtggcc aatgactcgc aaccactcac cgtctacttc tccctgagcc     180
tcctgcagat catggacgtg gatgagaaga accaagtttt aaccaccaac atttggctgc     240
aaatgtcttg gacagatcac tatttacagt ggaatgtgtc agaatatcca ggggtgaaga     300
ctgttcgttt cccagatggc cagatttgga aaccagacat tcttctctat aacagtgctg     360
atgagcgctt tgacgccaca ttccacacta acgtgttggt gaattcttct gggcattgcc     420
agtacctgcc tccaggcata ttcaagagtt cctgctacat cgatgtacgc tggtttccct     480
ttgatgtgca gcactgcaaa ctgaagtttg ggtcctggtc ttacggaggc tggtccttgg     540
atctgcagat gcaggaggca gatatcagtg gctatatccc caatggagaa tgggacctag     600
tgggaatccc cggcaagagg agtgaaaggt tctatgagtg ctgcaaagag ccctaccccg     660
atgtcacctt cacagtgacc atgcgccgca ggacgctcta ctatggcctc aacctgctga     720
tcccctgtgt gctcatctcc gccctcgccc tgctggtgtt cctgcttcct gcagattccg     780
gggagaagat ttccctgggg ataacagtct tactctctct taccgtcttc atgctgctcg     840
tggctgagat catgcccgca acatccgatt cggtaccatt gatagcccag tacttcgcca     900
gcaccatgat catcgtgggc ctctcggtgg tggtgacagt gatcgtgctg cagtaccacc     960
accacgaccc cgacggggc aagatgccca gtggaccag agtcatcctt ctgaactggt    1020
gcgcgtggtt cctgcgaatg aagaggcccg gggaggacaa ggtgcgcccg gcctgccagc    1080
acaagcagcg gcgctgcagc ctggccagtg tggagatgag cgccgtggcg ccgccgcccg    1140
ccagcaacgg gaacctgctg tacatcggct tccgcggcct ggacggcgtg cactgtgtcc    1200
cgacccccga ctctggggta gtgtgtggcc gcatggcctg ctcccccacg cacgatgagc    1260
acctcctgca cggcgggcaa cccccgaggc gggacccgga cttggccaag atcctggagg    1320
aggtccgcta cattgccaac cgcttccgct gccaggacga aagcgaggcg gtctgcagcg    1380
agtggaagtt cgccgcctgt gtggtggacc gcctgtgcct catggccttc tcggtcttca    1440
ccatcatctg caccatcggc atcctgatgt cggctcccaa cttcgtggag gccgtgtcca    1500
aagactttgc gtaa                                                     1514
```

US 9,309,221 B2

1-SUBSTITUTED INDAZOLE DERIVATIVE

This application is the U.S. national stage under 35 U.S.C. §371 of International Application Number PCT/JP2013/060744, filed on Apr. 9, 2013, which claims priority to Japanese Application No. 2012-089057, filed on Apr. 10, 2012, each of these applications is hereby incorporated by reference in its entirety.

TECHNICAL FIELD

The present invention relates to a novel indazole derivative which is a modulator of α7 nicotinic acetylcholine receptor (α7 nAChR). On the basis of such pharmacological properties, the present compound can be useful for treating, for example, diseases related to cholinergic properties in the central nervous system (CNS) and/or peripheral nervous system (PNS), diseases associated with smooth muscle contraction, endocrine disorders, neurodegenerative disorders, diseases such as inflammation and pain, and diseases associated with withdrawal symptoms caused by addictive drug abuse.

BACKGROUND OF THE INVENTION

Recently, potential neuroprotective-effects of nicotine have been shown, and meanwhile various neurodegenerative-models in animals and cultured cells suffering from excitotoxic injury, athrepsia, ischemia, injury, neuronal cell death induced by amyloid beta (Aβ) or neurodegeneration induced by protein aggregation have been proposed. In many cases where nicotine shows neuroprotective effects, it has been found that nicotinic acetylcholine receptors containing alpha7 subtype are activated. These findings suggest that nicotine is useful in providing neuroprotective effects, and indicate that receptors containing α7-subtype are directly related with the effects. These data suggest that α7 nicotinic acetylcholine receptor is typically a suitable molecular-target for neuroprotection. In other words, the neuroprotection may be accomplished by developing an active agonist/positive modulator (i.e. positive allosteric modulator: PAM) of the receptor. In fact, α7 nicotinic acetylcholine receptor agonist has already been identified, and is expected to provide a possible clue to the development of neuroprotective drugs. In addition, it has recently been reported that α7 nicotinic acetylcholine receptor is also involved in inflammation. Thus, the development of a novel modulator of the receptor is expected to lead to a novel treatment for nervous system diseases, psychiatric diseases and inflammatory diseases.

In the past, there were some disclosures about modulators of α7 nicotinic acetylcholine receptor (α7 nAChR), but the chemical structures thereof are different from that of the present compound (see, Patent Reference 1 and Patent Reference 2).

PRIOR ART DOCUMENTS

Patent References

[Patent Reference 1] WO 2003/093250
[Patent Reference 2] WO 2006/138510

SUMMARY OF THE INVENTION

Technical Problem

A problem to be solved by the present invention is to provide a novel compound which has potent modulatory-effects on the activity of α7 nicotinic acetylcholine receptor (α7 nAChR), and can be useful as a novel medicament for treating and/or preventing nervous system diseases, psychiatric diseases and inflammatory diseases.

In addition, WO 2012/133509 and WO 2012/176763 are applications related to the present application, which have already been published. The compounds therein have similar but different structures from that of the present compound. However, the priority date of the present application is earlier than the published dates of the related applications, and thus they are not prior art documents for the present application.

Solution to Problem

The present inventors have extensively studied to solve the above problem and then have found that a novel compound of the following Formula (I) exhibits potent modulatory-effects on the activity of α7 nicotinic acetylcholine receptor (α7 nAChR). On the basis of the new findings, the present invention has been completed. The present invention provides a 1-substituted indazole derivative of the following Formula (I) or a pharmaceutically acceptable salt thereof (hereinafter, optionally referred to as "the present compound"). In specific, the present invention is as follows:

Term 1. A compound of Formula (I):

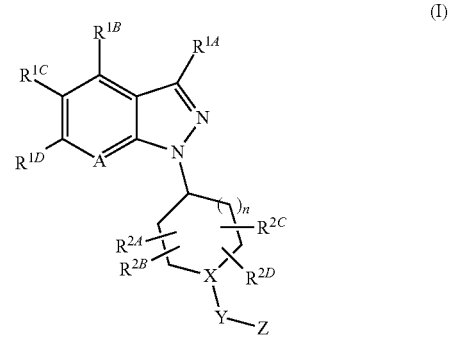

or a pharmaceutically acceptable salt thereof
wherein
A is $CR^{1E}$ or a nitrogen atom,
X—Y—Z is $N-CO-NR^{3A}R^{3B}$, $N-CO-R^4$, $CR^{2E}-CO-NR^{3A}R^{3B}$, $CR^{2E}-NR^5-COR^4$ or $CR^{2E}-NR^5-CONR^{3A}R^{3B}$,
$R^{1A}$ is a $C_{1-6}$ alkyl optionally substituted with 1 to 5 substituents independently selected from the group consisting of a fluorine atom, a hydroxy group, a $C_{1-6}$ alkoxy, a $C_{3-6}$ cycloalkyl, $-NR^6R^7$, $-CONR^6R^7$ and $-NR^6COR^7$; a $C_{3-10}$ cycloalkyl or a 4- to 10-membered saturated heterocycle (wherein the cycloalkyl and the saturated heterocycle may be optionally substituted with 1 to 5 substituents independently selected from the group consisting of a fluorine atom, a hydroxy group, a $C_{1-6}$ alkyl, a $C_{1-6}$ alkoxy and $-NR^6R^7$); a $C_{1-6}$ alkoxy optionally substituted with 1 to 5 substituents independently selected from the group consisting of a fluorine atom, a hydroxy group, a $C_{1-6}$ alkoxy, $-NR^6R^7$, $-CONR^6R^7$ and $-NR^6COR^7$; a hydrogen atom; a halogen; $-NR^6R^7$; a cyano group; $-CONR^6R^7$; $-NR^6COR^7$; or $-SO_2R^6$, provided that both $R^6$ and $R^7$ are not a hydrogen atom,
$R^{1B}$ to $R^{1E}$ are each independently a $C_{1-6}$ alkyl optionally substituted with 1 to 5 substituents independently selected from the group consisting of a fluorine atom, a hydroxy group, a $C_{1-6}$ alkoxy, a $C_{3-6}$ cycloalkyl, —$NR^{6'}R^{7'}$, —$CONR^{6'}R^{7'}$ and —$NR^{6'}COR^{7'}$; a $C_{3-10}$ cycloalkyl or a 4- to 10-membered saturated heterocycle (wherein the cycloalkyl and the saturated heterocycle may be optionally substituted with 1 to 5 substituents independently selected from the group consisting of a fluorine atom, a hydroxy group, a $C_{1-6}$ alkyl, a $C_{1-6}$ alkoxy, —$NR^{6'}R^{7'}$, —$CONR^{6'}R^{7'}$ and —$NR^{6'}COR^{7'}$); a $C_{1-6}$ alkoxy or a $C_{3-10}$ cycloalkoxy (wherein the alkoxy and the cycloalkoxy may be optionally substituted with 1 to 5 substituents independently selected from the group consisting of a fluorine atom, a hydroxy group, a $C_{1-6}$ alkoxy, —$CONR^{6'}R^{7'}$ and —$NR^{6'}COR^{7'}$); a hydrogen atom; a hydroxy group; a halogen; an aryl or a heteroaryl (wherein the aryl and the heteroaryl may be optionally substituted with 1 to 5 substituents independently selected from the group consisting of a halogen, a hydroxy group, a $C_{1-6}$ alkyl optionally substituted with 1 to 5 fluorine atoms, a $C_{1-6}$ alkoxy, —$NR^{6'}R^{7'}$, —$CONR^{6'}R^{7'}$ and —$NR^{6'}COR^{7'}$); —$NR^{6'}R^{7'}$; a cyano group; —$CONR^{6'}R^{7'}$; —$NR^{6'}COR^{7'}$; or —$SO_2R^{6'}$, provided that both $R^{6'}$ and $R^{7'}$ are not a hydrogen atom, $R^{2A}$ to $R^{2E}$ are each independently a $C_{1-6}$ alkyl optionally substituted with 1 to 5 substituents independently selected from the group consisting of a halogen, a hydroxy group, a $C_{1-6}$ alkoxy and —$NR^8R^9$; a hydrogen atom; a halogen; a hydroxy group; or a $C_{1-6}$ alkoxy optionally substituted with 1 to 5 fluorine atoms, or when two of $R^{2A}$ to $R^{2E}$ are a $C_{1-6}$ alkyl, they may be taken together to form a 4- to 10-membered saturated carbocyclic ring (which may be optionally substituted with 1 to 5 substituents independently selected from the group consisting of a fluorine atom, a hydroxy group, a $C_{1-6}$ alkyl, a $C_{1-6}$ alkoxy and —$NR^8R^9$), $R^{3A}$, $R^{3B}$ and $R^4$ are each independently a $C_{1-10}$ alkyl optionally substituted with 1 to 5 substituents independently selected from the group consisting of a phenyl group, a monocyclic heteroaryl, a 4- to 10-membered saturated heterocycle, a $C_{3-10}$ cycloalkyl, a fluorine atom, a hydroxy group, a $C_{1-6}$ alkoxy optionally substituted with 1 to 5 fluorine atoms, and —$NR^{10}R^{11}$; a $C_{3-10}$ cycloalkyl; a 4- to 10-membered saturated heterocycle; a phenyl group; a monocyclic heteroaryl; or a hydrogen atom, wherein the cycloalkyl, the saturated heterocycle, the phenyl and the monocyclic heteroaryl may be optionally substituted with 1 to 5 substituents independently selected from the group consisting of an aryl (which may be optionally substituted with 1 to 5 substituents independently selected from the group consisting of a fluorine atom, a $C_{1-6}$ alkoxy and —$NR^{10}R^{11}$), a halogen, a hydroxy group, a $C_{1-6}$ alkyl (which may be optionally substituted with 1 to 5 substituents independently selected from the group consisting of a fluorine atom, a $C_{1-6}$ alkoxy and —$NR^{10}R^{11}$), a $C_{1-6}$ alkoxy (which may be optionally substituted with 1 to 5 substituents independently selected from the group consisting of a $C_{3-6}$ cycloalkyl, a $C_{3-6}$ cycloalkyl-$C_{1-6}$ alkyl, a $C_{1-6}$ alkoxy and a fluorine atom), a $C_{1-6}$ alkylcarbonyl and —$NR^{10}R^{11}$, provided that (1) $R^{3A}$ and $R^{3B}$ may be taken together to form a 4- to 10-membered saturated heterocycle (which may be optionally substituted with 1 to 5 substituents independently selected from the group consisting of a fluorine atom, a hydroxy group, a $C_{1-6}$ alkyl, a $C_{1-6}$ alkoxy and —$NR^{10}R^{11}$), (2) both $R^{3A}$ and $R^{3B}$ are not a hydrogen atom, and (3) $R^4$ is not a hydrogen atom, $R^5$ to $R^{11}$, $R^{6'}$ and $R^{7'}$ are the same or different (each symbol is also the same or different when each symbol exists plurally) and are a hydrogen atom or a $C_{1-6}$ alkyl optionally substituted with 1 to 5 fluorine atoms, provided that in each combination of $R^6$-$R^7$, $R^{6'}$-$R^{7'}$, $R^8$-$R^9$, and $R^{10}$-$R^{11}$, (1) when one is a hydrogen atom, the other one is not a hydrogen atom, and (2) each combination may be taken together to form a 4- to 10-membered saturated heterocycle (which may be optionally substituted with 1 to 5 substituents independently selected from the group consisting of a fluorine atom, a hydroxy group, a $C_{1-6}$ alkyl, a $C_{1-6}$ alkoxy and —$NR^6R^7$), and n is 1 or 2.

Term 2. A compound of Formula (I):

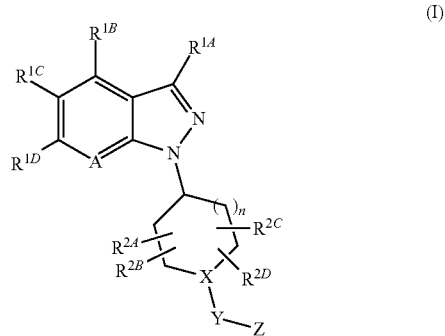

or a pharmaceutically acceptable salt thereof
wherein
A is $CR^{1E}$ or a nitrogen atom,
X—Y—Z is N—CO—$NR^{3A}R^{3B}$, N—CO—$R^4$, $CR^{2E}$—CO—$NR^{3A}R^{3B}$, $CR^{2E}$—$NR^5$—$COR^4$ or $CR^{2E}$—$NR^5$—CO—$NR^{3A}R^{3B}$, $R^{1A}$ is a $C_{1-6}$ alkyl optionally substituted with 1 to 5 substituents independently selected from the group consisting of a fluorine atom, a hydroxy group, a $C_{1-6}$ alkoxy, a $C_{3-6}$ cycloalkyl, —$NR^6R^7$, —$CONR^6R^7$, and —$NR^6COR^7$; a $C_{3-10}$ cycloalkyl or a 4- to 10-membered saturated heterocycle optionally substituted with 1 to 5 substituents independently selected from the group consisting of a fluorine atom, a hydroxy group, a $C_{1-6}$ alkyl, a $C_{1-6}$ alkoxy and —$NR^6R^7$; a $C_{1-6}$ alkoxy optionally substituted with 1 to 5 substituents independently selected from the group consisting of a fluorine atom, a hydroxy group, a $C_{1-6}$ alkoxy, —$NR^6R^7$, —$CONR^6R^7$, and —$NR^6COR^7$; a hydrogen atom; a halogen; —$NR^6R^7$; a cyano group; —$CONR^6R^7$; —$NR^6COR^7$; or —$SO_2R^6$, provided that both $R^6$ and $R^7$ are not a hydrogen atom, $R^{1B}$ to $R^{1E}$ are each independently a $C_{1-6}$ alkyl optionally substituted with 1 to 5 substituents independently selected from the group consisting of a fluorine atom, a hydroxy group, a $C_{1-6}$ alkoxy, a $C_{3-6}$ cycloalkyl, —$NR^6R^7$, —$CONR^6R^7$ and —$NR^6COR^7$; a $C_{3-10}$ cycloalkyl or a 4- to 10-membered saturated heterocycle optionally substituted with 1 to 5 substituents independently selected from the group consisting of a fluorine atom, a hydroxy group, a $C_{1-6}$ alkyl, a $C_{1-6}$ alkoxy, —$NR^6R^7$, —$CONR^6R^7$ and —$NR^6COR^7$; a $C_{1-6}$ alkoxy optionally substituted with 1 to 5 substituents independently selected from the group consisting of a fluorine atom, a hydroxy group, a $C_{1-6}$ alkoxy, —$CONR^6R^7$ and —$NR^6COR^7$; a hydrogen atom; a hydroxy group; a halogen; an aryl or heteroaryl optionally substituted with 1 to 5 substituents independently selected from the group consisting of a halogen, a hydroxy group, a $C_{1-6}$ alkyl optionally substituted with 1 to 5 fluorine atoms, a $C_{1-6}$ alkoxy, —$NR^6R^7$, —$CONR^6R^7$ and —$NR^6COR^7$; —$NR^6R^7$; a cyano group; —$CONR^6R^7$; —$NR^6COR^7$; or —$SO_2R^6$ provided that both $R^6$ and $R^7$ are not a hydrogen atom, $R^{2A}$ to $R^{2E}$ are each independently a $C_{1-6}$ alkyl optionally substituted with 1 to 5 substituents independently selected from the group consisting of a halogen, a hydroxy group, a $C_{1-6}$ alkoxy and —$NR^8R^9$; a hydrogen atom; a halogen; a hydroxy group; or a $C_{1-6}$ alkoxy optionally substituted with 1 to 5 fluorine atoms, or when two of $R^{2A}$ to $R^{2E}$ are a $C_{1-6}$ alkyl, they may be taken together to form a 4- to 10-membered saturated carbocyclic ring (which may be optionally substituted with 1 to 5 substituents independently selected from the group consisting of a fluorine atom, a hydroxy group, a $C_{1-6}$ alkyl, a $C_{1-6}$ alkoxy and —$NR^6R^7$), $R^{3A}$, $R^{3B}$ and $R^4$ are each independently a $C_{1-10}$ alkyl optionally substituted with 1 to 5 substituents independently selected from the group consisting of a phenyl group, a monocyclic heteroaryl, a 4- to 10-membered saturated heterocycle, a $C_{3-10}$ cycloalkyl, a fluorine atom, a hydroxy group, a $C_{1-6}$ alkoxy optionally substituted with 1 to 5 fluorine atoms and —$NR^{10}R^{11}$; a $C_{3-10}$ cycloalkyl; a 4- to 10-membered saturated heterocycle; a phenyl group; a monocyclic heteroaryl; or a hydrogen atom, wherein the cycloalkyl, the saturated heterocycle, the phenyl and the monocyclic heteroaryl may be optionally substituted with 1 to 5 substituents independently selected from the group consisting of a fluorine atom, a hydroxy group, a $C_{1-6}$ alkyl (which may be optionally substituted with 1 to 5 substituents independently selected from the group consisting of a fluorine atom, a $C_{1-6}$ alkoxy and —$NR^{10}R^{11}$), a alkoxy optionally substituted with 1 to 5 fluorine atoms and $C_{3-6}$ cycloalkyl or with 1 to 5 fluorine atoms, a alkylcarbonyl and —$NR^{10}R^{11}$, provided that (1) $R^{3A}$ and $R^{3B}$ may be taken together to form a 4- to 10-membered saturated heterocycle (which may be optionally substituted with 1 to substituents independently selected from the group consisting of a fluorine atom, a hydroxy group, a $C_{1-6}$ alkyl, a $C_{1-6}$ alkoxy and —$NR^6R^7$), (2) both $R^{3A}$ and $R^{3B}$ are not a hydrogen atom, and (3) $R^4$ is not a hydrogen atom, $R^5$ to $R^{11}$ are the same or different (each symbol is also the same or different when each symbol exists plurally) and a hydrogen atom or a $C_{1-6}$ alkyl optionally substituted with 1 to 5 fluorine atoms, provided that in each combination of $R^6$-$R^7$, $R^8$-$R^9$, and $R^{10}$-$R^{11}$, (1) when one is a hydrogen atom, the other one is not a hydrogen atom, and (2) each combination may be taken together to form a 4- to 10-membered saturated heterocycle (which may be optionally substituted with 1 to 5 substituents independently selected from the group consisting of a fluorine atom, a hydroxy group, a $C_{1-6}$ alkyl, a $C_{1-6}$ alkoxy and —$NR^6R^7$), and n is 1 or 2.

Term 3. The compound of Term 1 or 2 or a pharmaceutically acceptable salt thereof wherein X—Y—Z is N—CO—$NR^{3A}R^{3B}$, N—CO—$R^4$ or $CR^{2E}$—$NR^5$—$COR^4$.

Term 4. The compound of any one of Terms 1 to 3 or a pharmaceutically acceptable salt thereof wherein n is 1.

Term 5. The compound of any one of Terms 1 to 4 or a pharmaceutically acceptable salt thereof wherein either $R^{3A}$ or $R^{3B}$ is a hydrogen atom.

Term 6. The compound of any one of Terms 1 to 5 or a pharmaceutically acceptable salt thereof wherein $R^{2A}$ to $R^{2E}$ are each independently a $C_{1-6}$ alkyl optionally substituted with 1 to 5 fluorine atoms; a $C_{1-6}$ alkoxy; a hydrogen atom; or a fluorine atom.

Term 7. The compound of any one of Terms 1 to 6 or a pharmaceutically acceptable salt thereof wherein $R^{3A}$, $R^{3B}$ and $R^4$ are each independently a $C_{1-10}$ alkyl optionally substituted with 1 to 5 substituents independently selected from the group consisting of a 4- to 10-membered saturated heterocycle, a $C_{3-10}$ cycloalkyl, a fluorine atom, a hydroxy group, a $C_{1-6}$ alkoxy optionally substituted with 1 to 5 fluorine atoms and —$NR^{10}R^{11}$; a $C_{3-10}$ cycloalkyl; a 4- to 10-membered saturated heterocycle; a nitrogen-containing monocyclic heteroaryl; or a hydrogen atom, wherein the cycloalkyl, the saturated heterocycle and the nitrogen-containing monocyclic heteroaryl may be optionally substituted with 1 to 5 substituents independently selected from the group consisting of a fluorine atom, a hydroxy group, a $C_{1-6}$ alkyl (which may be optionally substituted with 1 to 5 substituents independently selected from the group consisting of a fluorine atom, a $C_{1-6}$ alkoxy and —$NR^{10}R^{11}$), a $C_{1-6}$ alkoxy optionally substituted with a $C_{3-6}$ cycloalkyl or 1 to 5 fluorine atoms, and —$NR^{10}R^{11}$, provided that (1) $R^{3A}$ and $R^{3B}$ may be taken together to form a 4- to 10-membered nitrogen-containing saturated heterocycle (which may be optionally substituted with 1 to 5 substituents independently selected from the group consisting of a fluorine atom, a hydroxy group, a $C_{1-6}$ alkyl, a $C_{1-6}$ alkoxy and —$NR^{10}R^{11}$), (2) both $R^{3A}$ and $R^{3B}$ are not a hydrogen atom, and (3) $R^4$ is not a hydrogen atom.

Term 8. The compound of any one of Terms 1 to 7 or a pharmaceutically acceptable salt thereof wherein $R^{1A}$ to $R^{1E}$ are each independently a $C_{1-6}$ alkyl optionally substituted with 1 to 5 substituents independently selected from the group consisting of a fluorine atom, a $C_{3-6}$ cycloalkyl, a hydroxy group and a $C_{1-6}$ alkoxy; a $C_{3-8}$ cycloalkyl optionally substituted with 1 to 5 substituents independently selected from the group consisting of a fluorine atom, a hydroxy group, a $C_{1-6}$ alkyl and a $C_{1-6}$ alkoxy; a $C_{1-6}$ alkoxy optionally substituted with 1 to 5 substituents independently selected from the group consisting of a fluorine atom, a hydroxy group and a $C_{1-6}$ alkoxy; a hydrogen atom; a halogen; or a 4- to 10-membered saturated heterocycle optionally substituted with a $C_{1-6}$ alkyl.

Term 9. The compound of any one of Terms 1 to 8 or a pharmaceutically acceptable salt thereof wherein X—Y—Z is N—CO—$NR^{3A}R^{3B}$ or $CR^{2E}$—$NR^5$—$COR^4$.

Term 10. The compound of any one of Terms 1 to 9 or a pharmaceutically acceptable salt thereof wherein A is $CR^{1E}$.

Term 11. The compound of any one of Terms 1 to 10 or a pharmaceutically acceptable salt thereof wherein $R^{3A}$, $R^{3B}$ and $R^4$ are each independently a $C_{1-10}$ alkyl optionally substituted with 1 to 5 substituents independently selected from the group consisting of a fluorine atom and a $C_{1-6}$ alkoxy optionally substituted with 1 to 5 fluorine atoms; a $C_{3-10}$ cycloalkyl; a 4- to 10-membered saturated heterocycle; or a hydrogen atom, wherein the cycloalkyl and the saturated heterocycle may be optionally substituted with 1 to 5 substituents independently selected from the group consisting of a fluorine atom, a $C_{1-6}$ alkyl (which may be optionally substituted with 1 to 5 substituents independently selected from the group consisting of a fluorine atom and a $C_{1-6}$ alkoxy) and a $C_{1-6}$ alkoxy optionally substituted with 1 to 5 fluorine atoms, provided that (1) both $R^{3A}$ and $R^{3B}$ are not a hydrogen atom, and (2) $R^4$ is not a hydrogen atom.

Term 12. The compound of any one of Terms 1 to 11 or a pharmaceutically acceptable salt thereof wherein $R^{1A}$ to $R^{1E}$ are each independently a $C_{1-6}$ alkyl optionally substituted with 1 to 5 substituents independently selected from the group consisting of a fluorine atom and a $C_{1-6}$ alkoxy; a $C_{3-8}$ cycloalkyl optionally substituted with 1 to 5 substituents independently selected from the group consisting of a fluorine atom, a $C_{1-6}$ alkyl and a $C_{1-6}$ alkoxy; a $C_{1-6}$ alkoxy optionally substituted with 1 to 5 substituents independently selected from the group consisting of a fluorine atom and a $C_{1-6}$ alkoxy; a hydrogen atom; or a halogen.

Term 13. The compound of any one of Terms 1 to 12 or a pharmaceutically acceptable salt thereof wherein X—Y—Z is N—CO—$NR^{3A}R^{3B}$.

7

Term 14. The compound of Term 1 selected from the following compounds or a pharmaceutically acceptable salt thereof:
N-(trans-4-methoxycyclohexyl)-4-(5-methyl-1H-indazol-1-yl)piperidine-1-carboxamide (Example 1),
4-(3-ethoxy-5-ethyl-1H-indazol-1-yl)-N-(tetrahydro-2H-pyran-4-yl)piperidine-1-carboxamide (Example 2),
(4,4-difluorocyclohexyl)(4-(5-ethoxy-1H-indazol-1-yl)piperidin-1-yl)methanone (Example 3),
N-(cis-4-(5-ethyl-1H-indazol-1-yl)cyclohexyl)-4,4-difluorocyclohexanecarboxamide (Example 4),
1-(4,4-difluorocyclohexyl)-3-(cis-4-(5-ethyl-1H-indazol-1-yl)cyclohexyl)urea (Example 5),
cis-N-(4,4-difluorocyclohexyl)-4-(5-ethyl-1H-indazol-1-yl)cyclohexanecarboxamide (Example 6),
N-cyclohexyl-4-(5-methyl-1H-indazol-1-yl)piperidine-1-carboxamide (Example 8),
N-(4,4-difluorocyclohexyl)-4-(5-methyl-1H-indazol-1-yl)piperidine-1-carboxamide (Example 13),
4-(5-propyl-1H-indazol-1-yl)-N-(tetrahydro-2H-pyran-4-yl)piperidine-1-carboxamide (Example 15),
4-(5-ethyl-1H-indazol-1-yl)-N-(trans-4-methoxycyclohexyl)piperidine-1-carboxamide (Example 16),
N-cyclohexyl-4-(5-ethoxy-1H-indazol-1-yl)piperidine-1-carboxamide (Example 18),
4-(5-ethyl-1H-indazol-1-yl)-N-(tetrahydro-2H-pyran-3-yl)piperidine-1-carboxamide (Example 22),
N-(4,4-difluorocyclohexyl)-4-(5-ethoxy-1H-indazol-1-yl)piperidine-1-carboxamide (Example 27),
N-(4,4-difluorocyclohexyl)-4-(5-fluoro-1H-indazol-1-yl)piperidine-1-carboxamide (Example 28),
4-(5-chloro-1H-indazol-1-yl)-N-cyclopentylpiperidine-1-carboxamide (Example 33),
4-(5-chloro-1H-indazol-1-yl)-N-(4,4-difluorocyclohexyl)piperidine-1-carboxamide (Example 34),
N-(4,4-difluorocyclohexyl)-4-(3-(methoxymethyl)-5-methyl-1H-indazol-1-yl)piperidine-1-carboxamide (Example 36),
N-(4,4-difluorocyclohexyl)-4-(5-methoxy-1H-indazol-1-yl)piperidine-1-carboxamide (Example 41),
N-(4,4-difluorocyclohexyl)-4-(3-ethyl-5-methyl-1H-indazol-1-yl)piperidine-1-carboxamide (Example 42),
N-(4,4-difluorocyclohexyl)-4-(3,5-dimethyl-1H-indazol-1-yl)piperidine-1-carboxamide (Example 45),
N-(4,4-difluorocyclohexyl)-4-(5-isopropoxy-1H-indazol-1-yl)piperidine-1-carboxamide (Example 46),
N-cyclohexyl-4-(5-isopropoxy-1H-indazol-1-yl)piperidine-1-carboxamide (Example 48),
N-(4,4-difluorocyclohexyl)-4-(5-methyl-3-(tetrahydro-2H-pyran-4-yl)-1H-indazol-1-yl)piperidine-1-carboxamide (Example 52),
4-(5-ethyl-3-isopropoxy-1H-indazol-1-yl)-N-(tetrahydro-2H-pyran-4-yl)piperidine-1-carboxamide (Example 63),
N-(4,4-difluorocyclohexyl)-4-(4-ethyl-1H-indazol-1-yl)piperidine-1-carboxamide (Example 64),
4-(4-ethyl-1H-indazol-1-yl)-N-(trans-4-methoxycyclohexyl)piperidine-1-carboxamide (Example 66),
N-(4,4-difluorocyclohexyl)-4-(5-(4-fluorophenyl)-1H-indazol-1-yl)piperidine-1-carboxamide (Example 70),
4-(5-cyclopropyl-1H-indazol-1-yl)-N-(trans-4-methoxycyclohexyl)piperidine-1-carboxamide (Example 74),
(R)—N-(2,2-difluorocyclohexyl)-4-(5-methyl-1H-indazol-1-yl)piperidine-1-carboxamide (Example 78),
(S)—N-(2,2-difluorocyclohexyl)-4-(5-methyl-1H-indazol-1-yl)piperidine-1-carboxamide (Example 79),
(S)—N-(2,2-difluorocyclopentyl)-4-(5-methyl-1H-indazol-1-yl)piperidine-1-carboxamide (Example 80),

8

(R)—N-(2,2-difluorocyclopentyl)-4-(5-methyl-1H-indazol-1-yl)piperidine-1-carboxamide (Example 81),
N-(trans-4-ethoxycyclohexyl)-4-(5-methyl-1H-indazol-1-yl)piperidine-1-carboxamide (Example 90), and
(4-(5-isobutyl-1H-indazol-1-yl)piperidin-1-yl)(tetrahydro-2H-pyran-4-yl)methanone (Example 103).
Term 15. The compound of Term 1 selected from the following compounds or a pharmaceutically acceptable salt thereof:
N-(trans-4-methoxycyclohexyl)-4-(5-methyl-1H-indazol-1-yl)piperidine-1-carboxamide (Example 1),
(4,4-difluorocyclohexyl)(4-(5-ethoxy-1H-indazol-1-yl)piperidin-1-yl)methanone (Example 3),
N-(4,4-difluorocyclohexyl)-4-(5-methyl-1H-indazol-1-yl)piperidine-1-carboxamide (Example 13),
4-(5-ethyl-1H-indazol-1-yl)-N-(trans-4-methoxycyclohexyl)piperidine-1-carboxamide (Example 16),
4-(5-ethyl-3-isopropoxy-1H-indazol-1-yl)-N-(tetrahydro-2H-pyran-4-yl)piperidine-1-carboxamide (Example 63),
4-(4-ethyl-1H-indazol-1-yl)-N-(trans-4-methoxycyclohexyl)piperidine-1-carboxamide (Example 66),
4-(5-cyclopropyl-1H-indazol-1-yl)-N-(trans-4-methoxycyclohexyl)piperidine-1-carboxamide (Example 74), and
N-(trans-4-ethoxycyclohexyl)-4-(5-methyl-1H-indazol-1-yl)piperidine-1-carboxamide (Example 90).
Term 16. The compound of Term 1 selected from the following compounds or a pharmaceutically acceptable salt thereof:
N-(trans-4-methoxycyclohexyl)-4-[5-($^2H_3$)methyl-1H-indazol-1-yl]piperidine-1-carboxamide (Example 144),
4-(4-ethoxy-5-methyl-1H-indazol-1-yl)-N-(trans-4-methoxycyclohexyl)piperidine-1-carboxamide (Example 145),
N-(trans-4-methoxycyclohexyl)-4-[5-(trifluoromethyl)-1H-indazol-1-yl]piperidine-1-carboxamide (Example 163),
N-{trans-4-[($^2H_3$)methoxy]cyclohexyl}-4-[5-(trifluoromethyl)-1H-indazol-1-yl]piperidine-1-carboxamide (Example 178),
N-(trans-4-methoxycyclohexyl)-4-[5-(trifluoromethoxy)-1H-indazol-1-yl]piperidine-1-carboxamide (Example 219),
N-{trans-4-[($^2H_3$)methoxy]cyclohexyl}-4-[5-(trifluoromethoxy)-1H-indazol-1-yl]piperidine-1-carboxamide (Example 226),
N-(tetrahydro-2H-pyran-4-yl)-4-[5-(trifluoromethoxy)-1H-indazol-1-yl]piperidine-1-carboxamide (Example 227),
4-[5-(cyclopropoxy)-1H-indazol-1-yl]-N-(trans-4-methoxycyclohexyl)piperidine-1-carboxamide (Example 230),
4-[5-(cyclopropoxy)-1H-indazol-1-yl]-N-(4,4-difluorocyclohexyl)piperidine-1-carboxamide (Example 249),
4-(5-ethyl-4-methoxy-1H-indazol-1-yl)-N-(trans-4-methoxycyclohexyl)piperidine-1-carboxamide (Example 255),
4-(5-cyclopropyl-4-methyl-1H-indazol-1-yl)-N-(tetrahydro-2H-pyran-4-yl)piperidine-1-carboxamide (Example 283),
4-(5-methyl-1H-indazol-1-yl)-N-{trans-4-[($^2H_3$)methoxy]cyclohexyl}piperidine-1-carboxamide (Example 295),
4-(5-cyclopropyl-1H-indazol-1-yl)-N-{trans-4-[($^2H_3$)methoxy]cyclohexyl}piperidine-1-carboxamide (Example 296),
N-(tetrahydro-2H-pyran-3-yl)-4-[5-(trifluoromethoxy)-1H-indazol-1-yl]piperidine-1-carboxamide (Example 300),
4-(5-cyclopropyl-1H-indazol-1-yl)-N-[(1S,3S)-3-methoxycyclohexyl]piperidine-1-carboxamide (Example 211),
4-(5-cyclopropyl-4-methoxy-1H-indazol-1-yl)-N-(trans-4-methoxycyclohexyl)piperidine-1-carboxamide (Example 263),
4-(4-ethoxy-5-ethyl-1H-indazol-1-yl)-N-(trans-4-methoxycyclohexyl)piperidine-1-carboxamide (Example 272),
4-(5-ethyl-4-methoxy-1H-indazol-1-yl)-N-(tetrahydro-2H-pyran-4-yl)piperidine-1-carboxamide (Example 275), 4-(5-cyclopropyl-4-methyl-1H-indazol-1-yl)-N-(trans-4-methoxycyclohexyl)piperidine-1-carboxamide (Example 277),
4-[5-(difluoromethoxy)-1H-indazol-1-yl]-N-(trans-4-methoxycyclohexyl)piperidine-1-carboxamide (Example 291), and
N-cyclobutyl-4-[5-(trifluoromethyl)-1H-indazol-1-yl]piperidine-1-carboxamide (Example 298).

Term 17. The compound of Term 1 selected from the following compounds or a pharmaceutically acceptable salt thereof:
N-(trans-4-methoxycyclohexyl)-4-(5-methyl-1H-indazol-1-yl)piperidine-1-carboxamide (Example 1),
4-(5-ethyl-3-isopropoxy-1H-indazol-1-yl)-N-(tetrahydro-2H-pyran-4-yl)piperidine-1-carboxamide (Example 63),
4-(5-cyclopropyl-1H-indazol-1-yl)-N-(trans-4-methoxycyclohexyl)piperidine-1-carboxamide (Example 74),
N-(trans-4-methoxycyclohexyl)-4-[5-($^2H_3$)methyl-1H-indazol-1-yl]piperidine-1-carboxamide (Example 144),
4-(4-ethoxy-5-methyl-1H-indazol-1-yl)-N-(trans-4-methoxycyclohexyl)piperidine-1-carboxamide (Example 145),
N-(trans-4-methoxycyclohexyl)-4-[5-(trifluoromethyl)-1H-indazol-1-yl]piperidine-1-carboxamide (Example 163),
N-{trans-4-[($^2H_3$)methoxy]cyclohexyl}-4-[5-(trifluoromethyl)-1H-indazol-1-yl]piperidine-1-carboxamide (Example 178),
N-{trans-4-[($^2H_3$)methoxy]cyclohexyl}-4-[5-(trifluoromethoxy)-1H-indazol-1-yl]piperidine-1-carboxamide (Example 226),
N-(tetrahydro-2H-pyran-4-yl)-4-[5-(trifluoromethoxy)-1H-indazol-1-yl]piperidine-1-carboxamide (Example 227),
4-(5-methyl-1H-indazol-1-yl)-N-{trans-4-[($^2H_3$)methoxy]cyclohexyl}piperidine-1-carboxamide (Example 295),
4-(5-cyclopropyl-1H-indazol-1-yl)-N-{trans-4-[($^2H_3$)methoxy]cyclohexyl}piperidine-1-carboxamide (Example 296), and
N-(tetrahydro-2H-pyran-3-yl)-4-[5-(trifluoromethoxy)-1H-indazol-1-yl]piperidine-1-carboxamide (Example 300).

Term 18. The compound of Term 1 which is N-(trans-4-methoxycyclohexyl)-4-(5-methyl-1H-indazol-1-yl)piperidine-1-carboxamide (Example 1), or a pharmaceutically acceptable salt thereof.

Term 19. The compound of Term 1 which is 4-(5-ethyl-3-isopropoxy-1H-indazol-1-yl)-N-(tetrahydro-2H-pyran-4-yl)piperidine-1-carboxamide (Example 63), or a pharmaceutically acceptable salt thereof.

Term 20. The compound of Term 1 which is N-(trans-4-methoxycyclohexyl)-4-[5-($^2H_3$)methyl-1H-indazol-1-yl]piperidine-1-carboxamide (Example 144), or a pharmaceutically acceptable salt thereof.

Term 21. The compound of Term 1 which is N-(tetrahydro-2H-pyran-4-yl)-4-[5-(trifluoromethoxy)-1H-indazol-1-yl]piperidine-1-carboxamide (Example 227), or a pharmaceutically acceptable salt thereof.

Term 22. The compound of Term 1 which is 4-(5-methyl-1H-indazol-1-yl)-N-{trans-4-[($^2H_3$)methoxy]cyclohexyl}piperidine-1-carboxamide (Example 295), or a pharmaceutically acceptable salt thereof.

Term 23. A pharmaceutical composition comprising the compound of any one of Terms 1 to 22 or a pharmaceutically acceptable salt thereof.

Term 24. A medicament for treating a disease related to acetylcholine comprising the compound of any one of Terms 1 to 22 or a pharmaceutically acceptable salt thereof as an active ingredient.

Term 25. The medicament of Term 24 wherein the disease related to acetylcholine is a nervous system disease, psychiatric disease or inflammatory disease.

Term 26. The medicament of Term 25 wherein the nervous system disease, the psychiatric disease or the inflammatory disease is dementia, schizophrenia, CIAS (cognitive impairment associated with schizophrenia), Alzheimer's disease, Down's syndrome, attention deficit disorder or cerebral angiopathy.

Term 27. A method for treating or preventing a nervous system disease, psychiatric disease or inflammatory disease which comprises administering a therapeutically effective amount of the compound of any one of Terms 1 to 22 or a pharmaceutically acceptable salt thereof to a patient in need thereof.

Term 28. A combination drug comprising the compound of any one of Terms 1 to 22 or a pharmaceutically acceptable salt thereof, and at least one drug selected from drugs classified as atypical antipsychotic drugs.

Term 29. A method for treating a disease due to an abnormality of the intracellular signaling mediated by acetylcholine which comprises administering a therapeutically effective amount of the compound of any one of Terms 1 to 22 or a pharmaceutically acceptable salt thereof to a patient in need thereof.

Term 30. The compound of any one of Terms 1 to 22 or a pharmaceutically acceptable salt thereof for use in the treatment of a disease due to an abnormality of the intracellular signaling mediated by acetylcholine.

Term 31. A pharmaceutical composition comprising the compound of any one of Terms 1 to 22 or a pharmaceutically acceptable salt thereof for use in the treatment of a disease due to an abnormality of the intracellular signaling mediated by acetylcholine.

Term 32. Use of the compound of any one of Terms 1 to 22 or a pharmaceutically acceptable salt thereof for the manufacture of a medicament to treat a disease due to an abnormality of the intracellular signaling mediated by acetylcholine.

Effects of Invention

The present compound is useful as a novel medicament for treating and/or preventing nervous system diseases, psychiatric diseases, and inflammatory diseases such as dementia, schizophrenia, CIAS (cognitive impairment associated with schizophrenia), Alzheimer's disease, Down's syndrome, attention deficit disorder and cerebrovascular disorder. Furthermore, the present compound in combination with a drug classified as atypical antipsychotic drugs is useful for treating and/or preventing nervous system diseases and psychiatric diseases such as schizophrenia.

DESCRIPTION OF EMBODIMENTS

The present compound may exist in a form of hydrates and/or solvates, and thus such hydrates and/or solvates are also included in the present compound.

The compound of Formula (I) may contain one or more asymmetric carbon atoms, or may have a geometrical isomerism or an axial chirality; thus the compound may exist as several stereoisomers. Such stereoisomers, mixtures thereof, and racemates are also included in the present compound of Formula (I).

The compound of Formula (I) wherein one or more of $^1H$ are substituted with $^2H(D)$ (i.e. deuterated form) is also included in the present compound of Formula (I).

The compound of Formula (I) or a pharmaceutically acceptable salt thereof can be obtained in a form of crystal which may show polymorphism, thus such crystalline polymorphism is also included in the present invention.

The terms used herein are explained hereinafter.

The term "alkyl" as used herein refers to a straight or branched saturated hydrocarbon group. For example, the terms "$C_{1-4}$ alkyl", "$C_{1-6}$ alkyl" and "$C_{1-10}$ alkyl" refer to an alkyl with 1 to 4, 1 to 6 and 1 to 10 carbon atoms, respectively. In specific, "$C_{1-4}$ alkyl" includes, for example, methyl, ethyl, propyl, isopropyl, butyl, isobutyl, sec-butyl, and tert-butyl. In addition to said groups, "$C_{1-6}$ alkyl" includes, for example, pentyl, isopentyl, neopentyl, and hexyl. In addition to said groups, "$C_{1-10}$ alkyl" includes, for example, heptyl and octyl.

The term "cycloalkyl" as used herein refers to a monocyclic or polycyclic saturated hydrocarbon including those which have a partially-cross-linked structure or form a fused ring with an aryl or heteroaryl. For example, "$C_{3-10}$ cycloalkyl" refers to a cyclic alkyl with 3 to 10 carbon atoms and includes, for example, cyclopropyl, cyclobutyl, cyclopentyl, cyclohexyl, cycloheptyl, cyclooctyl, and adamantyl.

The term "alkoxy" as used herein refers to a straight or branched saturated hydrocarbon group attached to the parent molecular moiety through an oxygen atom. For example, "$C_{1-6}$ alkoxy" refers to an alkoxy with 1 to 6 carbon atoms and includes, for example, methoxy, ethoxy, propoxy, isopropoxy, butyloxy, pentyloxy, isopentyloxy, neopentyloxy, and hexyloxy.

The term "cycloalkoxy" as used herein refers to the above-defined "cycloalkyl" which is attached to the parent molecular moiety through an oxygen atom.

The term "$C_{1-6}$ alkylcarbonyl" as used herein includes, for example, acetyl, ethylcarbonyl, propylcarbonyl, isopropylcarbonyl, butylcarbonyl, isobutylcarbonyl, and t-butylcarbonyl; preferably "$C_{1-3}$ alkylcarbonyl"; and more preferably acetyl.

The term "halogen" as used herein refers to a fluorine, chlorine, bromine or iodine atom; and preferably a fluorine or chlorine atom.

The term "aryl" as used herein includes, for example, phenyl, 1-naphthyl, 2-naphthyl, and anthracenyl; and preferably phenyl.

The term "heteroaryl" as used herein includes a 5- to 7-membered monocyclic aromatic heterocyclic group, a 8- to 11-membered bicyclic aromatic heterocyclic group, and a 12- to 16-membered tricyclic aromatic heterocyclic group which comprise 1 to 4 atoms selected from the group consisting of nitrogen, oxygen and sulfur atoms. The heteroaryl includes, for example, pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, triazinyl, triazolyl, imidazolidinyl, oxadiazolyl, triazolyl, tetrazolyl, indolyl, indazolyl, chromenyl, quinolyl, isoquinolyl, benzofuranyl, benzothienyl, benzoxazolyl, benzothiazolyl, benzisoxazolyl, benzisothiazolyl, benzotriazolyl, benzimidazolyl, thioxanthenyl, and 6,11-dihydrodibenzo[B,E]thiepinyl; and preferably pyridyl, pyrimidinyl, quinolyl, and isoquinolyl.

The term "monocyclic heteroaryl" as used herein includes a 5- to 7-membered monocyclic aromatic heterocyclic group which comprises 1 to 4 atoms selected from the group consisting of nitrogen, oxygen and sulfur atoms. The monocyclic heteroaryl includes, for example, pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, triazinyl, triazolyl, imidazolidinyl, oxadiazolyl, triazolyl, and tetrazolyl; preferably a nitrogen-containing monocyclic heteroaryl, for example, pyridyl and pyrimidinyl.

The term "4- to 10-membered saturated heterocycle" as used herein refers to a monocyclic or bicyclic saturated heterocycle comprising 4 to 10 ring atoms which include 1 to 2 atoms selected from the group consisting of nitrogen, oxygen and sulfur atoms. The 4- to 10-membered saturated heterocycle also includes those which have a partially-cross-linked structure, those which are partially spirocyclized, those which are partially unsaturated, and those which form a fused ring with an aryl or heteroaryl. The 4- to 10-membered saturated heterocycle includes, for example, azetidine, pyrrolidine, piperidine, piperazine, morpholine, homopiperidine, tetrahydrofuran, tetrahydropyran, and 3,6-dihydro-2H-pyran.

Among the present compounds represented by Formula (I), A, X—Y—Z, $R^{1A}$ to $R^{1E}$, $R^{2A}$ to $R^{2E}$, $R^{3A}$, $R^{3B}$, $R^4$ to $R^{11}$, $R^{6'}$, $R^{7'}$ and n are preferably those shown below, but the technical scope of the present invention should not be limited to the following compounds. In addition, the phrase "$R^4$ to $R^{11}$" means $R^4$, $R^5$, $R^6$, $R^7$, $R^8$, $R^9$, $R^{10}$ and $R^{11}$, and other similar phrases mean likewise.

A is preferably $CR^{1E}$ or a nitrogen atom, and more preferably $CR^{1E}$.

X—Y—Z is preferably N—CO—$NR^{3A}R^{3B}$, N—CO—$R^4$, $CR^{2E}$—CO—$NR^{3A}R^{3B}$ or $CR^{2E}$—$NR^5$—$COR^4$, more preferably N—CO—$NR^{3A}R^{3B}$ or $CR^{2E}$—$NR^5$—$COR^4$, and even more preferably N—CO—$NR^{3A}R^{3B}$.

$R^{1A}$ to $R^{1E}$ are preferably a $C_{1-6}$ alkyl optionally substituted with 1 to 5 substituents independently selected from the group consisting of a fluorine atom, a hydroxy group and a $C_{1-6}$ alkoxy; a $C_{3-8}$ cycloalkyl optionally substituted with 1 to 5 substituents independently selected from the group consisting of a fluorine atom, a hydroxy group, a $C_{1-6}$ alkyl and a $C_{1-6}$ alkoxy; a $C_{1-6}$ alkoxy optionally substituted with 1 to 5 substituents independently selected from the group consisting of a fluorine atom, a hydroxy group and a $C_{1-6}$ alkoxy; a hydrogen atom; a halogen; or a 4- to 10-membered saturated heterocycle optionally substituted with a $C_{1-6}$ alkyl. $R^{1A}$ to $R^{1E}$ are more preferably a $C_{1-6}$ alkyl optionally substituted with 1 to 5 substituents independently selected from the group consisting of a fluorine atom and a $C_{1-6}$ alkoxy; a $C_{3-8}$ cycloalkyl optionally substituted with 1 to 5 substituents independently selected from the group consisting of a fluorine atom, a $C_{1-6}$ alkyl and a $C_{1-6}$ alkoxy; a $C_{1-6}$ alkoxy optionally substituted with 1 to 5 fluorine atoms; a hydrogen atom; or a halogen. $R^{1A}$ to $R^{1E}$ are even more preferably a $C_{1-6}$ alkyl optionally substituted with 1 to 5 substituents independently selected from the group consisting of a fluorine atom and a $C_{1-6}$ alkoxy; a $C_{1-6}$ alkoxy optionally substituted with 1 to 5 fluorine atoms; a hydrogen atom; or a halogen. $R^{1A}$ to $R^{1E}$ are the most preferably a $C_{1-6}$ alkyl optionally substituted with 1 to 5 fluorine atoms; a $C_{1-6}$ alkoxy optionally substituted with 1 to 5 fluorine atoms; or a hydrogen atom.

$R^{2A}$ to $R^{2E}$ are preferably a $C_{1-6}$ alkyl optionally substituted with 1 to 5 fluorine atoms; a $C_{1-6}$ alkoxy; a hydrogen atom; or a fluorine atom. $R^{2A}$ to $R^{2E}$ are more preferably a $C_{1-6}$ alkyl, a hydrogen atom or a fluorine atom, even more preferably a $C_{1-6}$ alkyl or a hydrogen atom, and the most preferably a hydrogen atom.

$R^{3A}$, $R^{3B}$ and $R^4$ are preferably a $C_{1-10}$ alkyl optionally substituted with 1 to 5 substituents independently selected from the group consisting of a 4- to 10-membered saturated heterocycle, a $C_{3-10}$ cycloalkyl, a fluorine atom, a hydroxy group, a $C_{1-6}$ alkoxy optionally substituted with 1 to 5 fluorine atoms, and —$NR^{10}R^{11}$; a $C_{3-10}$ cycloalkyl; a 4- to 10-membered saturated heterocycle; a nitrogen-containing monocyclic heteroaryl; or a hydrogen atom, wherein the cycloalkyl, the saturated heterocycle and the nitrogen-containing monocyclic heteroaryl may be optionally substituted with 1 to 5 substituents independently selected from the group consisting of a fluorine atom, a hydroxy group, a $C_{1-6}$ alkyl (which may be optionally substituted with 1 to 5 substituents independently selected from the group consisting of a fluorine atom, a $C_{1-6}$ alkoxy and —$NR^{10}R^{11}$), a $C_{1-6}$ alkoxy optionally substituted with 1 to 5 fluorine atoms and —$NR^{10}R^{11}$, provided that (1) $R^{3A}$ and $R^{3B}$ may be taken together to form a 4- to 10-membered nitrogen-containing saturated heterocycle (which may be optionally substituted with the substituents of the above-mentioned saturated heterocycle), (2) both $R^{3A}$ and $R^{3B}$ are not a hydrogen atom, and (3) $R^4$ is not a hydrogen atom.

$R^{3A}$, $R^{3B}$ and $R^4$ are more preferably, a $C_{1-10}$ alkyl optionally substituted with 1 to 5 substituents independently selected from the group consisting of a fluorine atom and a $C_{1-6}$ alkoxy optionally substituted with 1 to 5 fluorine atoms; a $C_{3-10}$ cycloalkyl; a 4- to 10-membered saturated heterocycle; or a hydrogen atom, wherein the cycloalkyl and the saturated heterocycle may be optionally substituted with 1 to 5 substituents independently selected from the group consisting of a fluorine atom, a $C_{1-6}$ alkyl (which may be optionally substituted with 1 to 5 substituents independently selected from the group consisting of a fluorine atom and a $C_{1-6}$ alkoxy) and a $C_{1-6}$ alkoxy optionally substituted with 1 to 5 fluorine atoms.

$R^{3A}$, $R^{3B}$ and $R^4$ are even more preferably a $C_{1-10}$ alkyl; a $C_{3-10}$ cycloalkyl; a 4- to 10-membered saturated heterocycle; or a hydrogen atom, wherein the cycloalkyl and the saturated heterocycle may be optionally substituted with 1 to 3 substituents independently selected from the group consisting of a fluorine atom, a $C_{1-6}$ alkyl and a $C_{1-6}$ alkoxy.

$R^{3A}$, $R^{3B}$ and $R^4$ are the most preferably a $C_{3-10}$ cycloalkyl; a 4- to 10-membered saturated heterocycle; or a hydrogen atom, wherein the cycloalkyl and the saturated heterocycle may be optionally substituted with 1 to 3 substituents independently selected from the group consisting of a $C_{1-6}$ alkyl and a $C_{1-6}$ alkoxy.

Furthermore, in another embodiment, either $R^{3A}$ or $R^{3B}$ is a hydrogen atom.

$R^5$ to $R^{11}$, $R^{6'}$ and $R^{7'}$ are the same or different (each symbol is also the same or different when each symbol exists plurally) and are preferably a hydrogen atom or a $C_{1-6}$ alkyl optionally substituted with 1 to 5 fluorine atoms, more preferably a hydrogen atom or a $C_{1-6}$ alkyl, and even more preferably a $C_{1-6}$ alkyl, provided that in each combination of $R^6$-$R^7$, $R^{6'}$-$R^{7'}$, $R^8$-$R^9$, and $R^{10}$-$R^{11}$, (1) when one is a hydrogen atom, the other one is not a hydrogen atom, and (2) each combination may be taken together to form a 4- to 10-membered saturated heterocycle.

n is 1 or 2, and preferably 1.

A pharmaceutically acceptable salt of the compound of Formula (I) means that the structure of Formula (I) has a group which can form an acid or base addition salt, thereby forming a pharmaceutically acceptable acid or base addition salt of the compound of Formula (I).

When the present compound has basic groups such as an amino group, it may form various acid salts. The acid addition salt of the present compound includes, for example, inorganic acid salts such as hydrochloride, hydrobromide, hydroiodide, sulfate, perchlorate, and phosphate; organic acid salts such as oxalate, malonate, maleate, fumarate, lactate, malate, citrate, tartrate, benzoate, trifluoroacetate, acetate, methanesulfonate, p-toluenesulfonate, and trifluoromethanesulfonate; and amino-acid salts such as glutamate and aspartate.

When the present compound has acid groups such as a carboxyl group, it may form salts with various bases. Such pharmaceutically acceptable salts include, for example, alkali metal salts such as sodium and potassium salts, alkaline earth metal salts such as calcium salts, and ammonium salts.

These salts can be prepared by mixing the present compound of Formula (I) with the above-mentioned acid or base and then isolating it according to conventional methods such as recrystallization.

For the purpose of simplifying expressions, the following abbreviations may be optionally used herein.

o-: ortho-
m-: meta-
p-: para-
t-: tert-
s-: sec-
$CHCl_3$: chloroform
$CH_2Cl_2$: dichloromethane
THF: tetrahydrofuran
DMF: N,N-dimethylformamide
DMSO: dimethylsulfoxide
PAM: positive allosteric modulator
HEPES: N-2-hydroxyethylpiperazine-N'-2-ethanesulfonic acid
BSA: bovine serum albumin
FDSS: Functional Drug Screening System
Boc: tert-butoxycarbonyl
c-Hex: cyclohexyl
c-Pen: cyclopentyl
iPr: isopropyl
c-Pr: cyclopropyl
n-Pr: normalpropyl
EDCI·HCl: N-(3-dimethylaminopropyl)-N'-ethylcarbodiimide hydrochloride
HOBt: 1-hydroxybenzotriazole
DIEA: diisopropylethylamine
TEA: triethylamine
Ms: methanesulfonyl Hereinafter, processes of the present compound are explained. The present compound of Formula (I) can be prepared by, for example, the following Processes $A^1$, $A^2$, B, $C^1$, $C^2$ and D.

Process $A^1$

Among the compounds of Formula (I), those wherein X—Y—Z is N—CO—$NR^{3A}R^{3B}$ and $R^{1A}$ is neither alkoxy nor hydrogen atom as shown by Formula A1 (i.e. Compound A1) can be prepared by, for example, the following process:

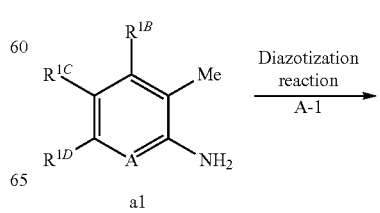

a1

-continued

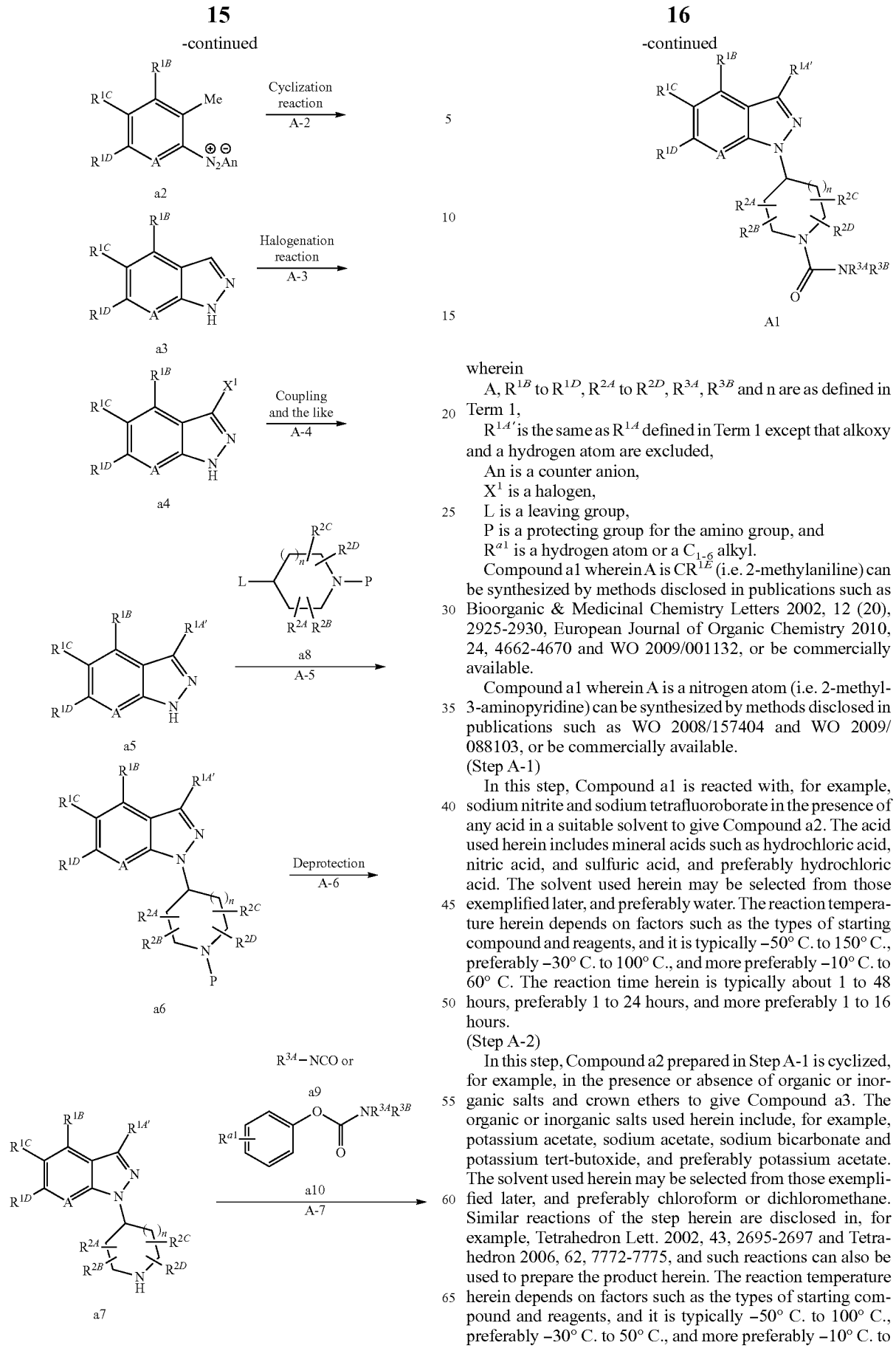

A1 wherein
A, $R^{1B}$ to $R^{1D}$, $R^{2A}$ to $R^{2D}$, $R^{3A}$, $R^{3B}$ and n are as defined in Term 1,
$R^{1A'}$ is the same as $R^{1A}$ defined in Term 1 except that alkoxy and a hydrogen atom are excluded,
An is a counter anion,
$X^1$ is a halogen,
L is a leaving group,
P is a protecting group for the amino group, and
$R^{a1}$ is a hydrogen atom or a $C_{1-6}$ alkyl.

Compound a1 wherein A is $CR^{1E}$ (i.e. 2-methylaniline) can be synthesized by methods disclosed in publications such as Bioorganic & Medicinal Chemistry Letters 2002, 12 (20), 2925-2930, European Journal of Organic Chemistry 2010, 24, 4662-4670 and WO 2009/001132, or be commercially available.

Compound a1 wherein A is a nitrogen atom (i.e. 2-methyl-3-aminopyridine) can be synthesized by methods disclosed in publications such as WO 2008/157404 and WO 2009/088103, or be commercially available.

(Step A-1)

In this step, Compound a1 is reacted with, for example, sodium nitrite and sodium tetrafluoroborate in the presence of any acid in a suitable solvent to give Compound a2. The acid used herein includes mineral acids such as hydrochloric acid, nitric acid, and sulfuric acid, and preferably hydrochloric acid. The solvent used herein may be selected from those exemplified later, and preferably water. The reaction temperature herein depends on factors such as the types of starting compound and reagents, and it is typically −50° C. to 150° C., preferably −30° C. to 100° C., and more preferably −10° C. to 60° C. The reaction time herein is typically about 1 to 48 hours, preferably 1 to 24 hours, and more preferably 1 to 16 hours.

(Step A-2)

In this step, Compound a2 prepared in Step A-1 is cyclized, for example, in the presence or absence of organic or inorganic salts and crown ethers to give Compound a3. The organic or inorganic salts used herein include, for example, potassium acetate, sodium acetate, sodium bicarbonate and potassium tert-butoxide, and preferably potassium acetate. The solvent used herein may be selected from those exemplified later, and preferably chloroform or dichloromethane. Similar reactions of the step herein are disclosed in, for example, Tetrahedron Lett. 2002, 43, 2695-2697 and Tetrahedron 2006, 62, 7772-7775, and such reactions can also be used to prepare the product herein. The reaction temperature herein depends on factors such as the types of starting compound and reagents, and it is typically −50° C. to 100° C., preferably −30° C. to 50° C., and more preferably −10° C. to 30° C. The reaction time herein is typically about 1 to 48 hours, preferably 1 to 24 hours, and more preferably 1 to 16 hours.

(Step A-3)

In this step, Compound a3 prepared in Step A-2 is halogenated to give Compound a4. For example, in case of iodination, the reaction can be carried out with iodine in the presence of any base in a suitable solvent. The base used herein may be selected from those exemplified later, and preferably sodium hydroxide or potassium hydroxide. The solvent used herein may be selected from those exemplified later, and preferably dimethylformamide or chloroform. The reaction temperature herein depends on factors such as the types of starting compound and reagents, and it is typically −30° C. to 200° C., preferably −10° C. to 100° C., and more preferably 0° C. to 80° C. The reaction time herein is typically about 1 to 48 hours, preferably 1 to 24 hours, and more preferably 1 to 16 hours.

(Step A-4)

In this step, Compound a4 prepared in Step A-3 is coupled with borane acid and the like in the presence of a catalyst and base to give Compound a5. The catalyst used herein includes those wherein a transition metal (e.g. palladium), a salt, complex or polymer thereof, or the like is supported on a carrier. The base used herein may be selected from those exemplified later, and preferably sodium carbonate, potassium carbonate or the like. The solvent used herein may be selected from those exemplified later, and preferably a mixed solvent of dioxane and water. Similar reactions of the step herein are disclosed in, for example, WO 2005/073219 and such reactions can also be used to prepare the product herein. The reaction temperature herein depends on factors such as the types of starting compound and reagents, and it is typically 0° C. to 200° C., preferably 30° C. to 150° C., and more preferably 50° C. to 120° C. The reaction time herein is typically about 1 to 48 hours, preferably 1 to 24 hours, and more preferably 1 to 16 hours.

(Step A-5)

In this step, Compound a5 prepared in Step A-4 is reacted with Compound a8 in the presence of a base to give Compound a6. The base used herein may be selected from those exemplified later, and preferably sodium hydride, potassium t-butoxide or the like. The reductant used herein may be hydrogen, formates such as ammonium formate, or hydrazine. The solvent used herein may be selected from those exemplified later, and preferably DMF or THF. In addition, Compound a8 can also be synthesized by methods disclosed in publications such as WO 2012/068106, WO 2007/030366 and Tetrahedron Lett. 2012, 53, 948-951, or be commercially available. The reaction temperature herein depends on factors such as the types of starting compound and reagents, and it is typically 0° C. to 200° C., preferably 30° C. to 150° C., and more preferably 50° C. to 120° C. The reaction time herein is typically about 1 to 48 hours, preferably 1 to 24 hours, and more preferably 1 to 16 hours.

(Step A-6)

In this step, the protecting group for the amino group of Compound a6 prepared in Step A-5 (defined as "P") is deprotected to give Compound a7. The step herein can be carried out according to methods disclosed in, for example, Protective Groups in Organic Synthesis (Theodora W. Greene, Peter G. M. Wuts, John Wiley & Sons, Inc., 1999). The reaction temperature herein depends on factors such as the types of starting compound and reagents, and it is typically −30° C. to 200° C., preferably 0° C. to 150° C., and more preferably 0° C. to 80° C. The reaction time herein is typically about 1 to 48 hours, preferably 1 to 24 hours, and more preferably 1 to 16 hours.

(Step A-7)

In this step, Compound a7 prepared in Step A-6 is reacted with Compound a9 or a10 in the presence of any base in a suitable solvent to give compound A1. The base used herein may be selected from those exemplified later, and preferably diisopropylethylamine or triethylamine. The solvent used herein may be selected from those exemplified later, and preferably tetrahydrofuran or dimethylformamide. In addition, Compound a9 or a10 can be commercially available or prepared according to conventional methods. The reaction temperature herein depends on factors such as the types of starting compound and reagents, and it is typically −50° C. to 200° C., preferably −20° C. to 150° C., and more preferably 0° C. to 100° C. The reaction time herein is typically about 1 to 48 hours, preferably 1 to 24 hours, and more preferably 1 to 16 hours.

Process $A^2$

Among the compounds of Formula (I), those wherein X—Y—Z is N—CO—NR$^{3A}$R$^{3B}$ and R$^{1A}$ is an optionally-substituted alkoxy as shown by Formula A2 (i.e. Compound A2) can be prepared by, for example, the following process:

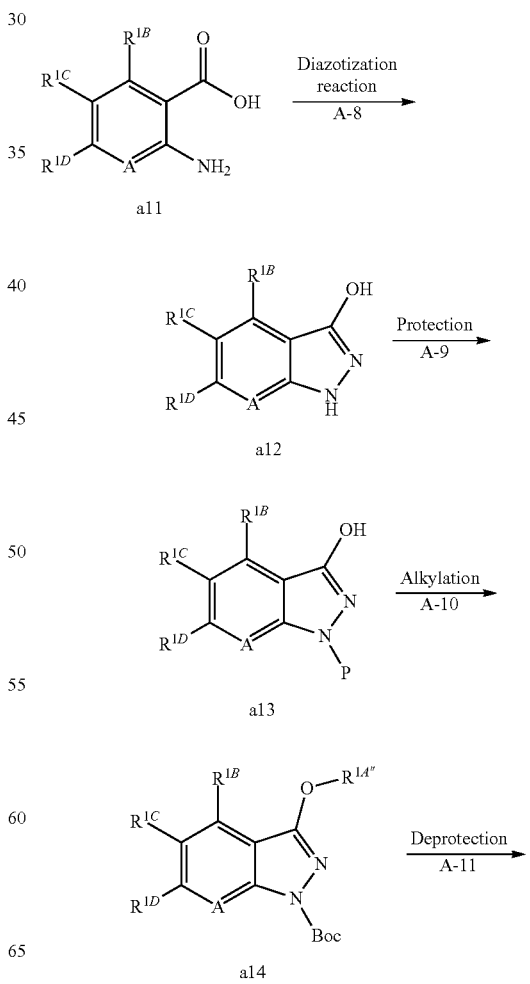

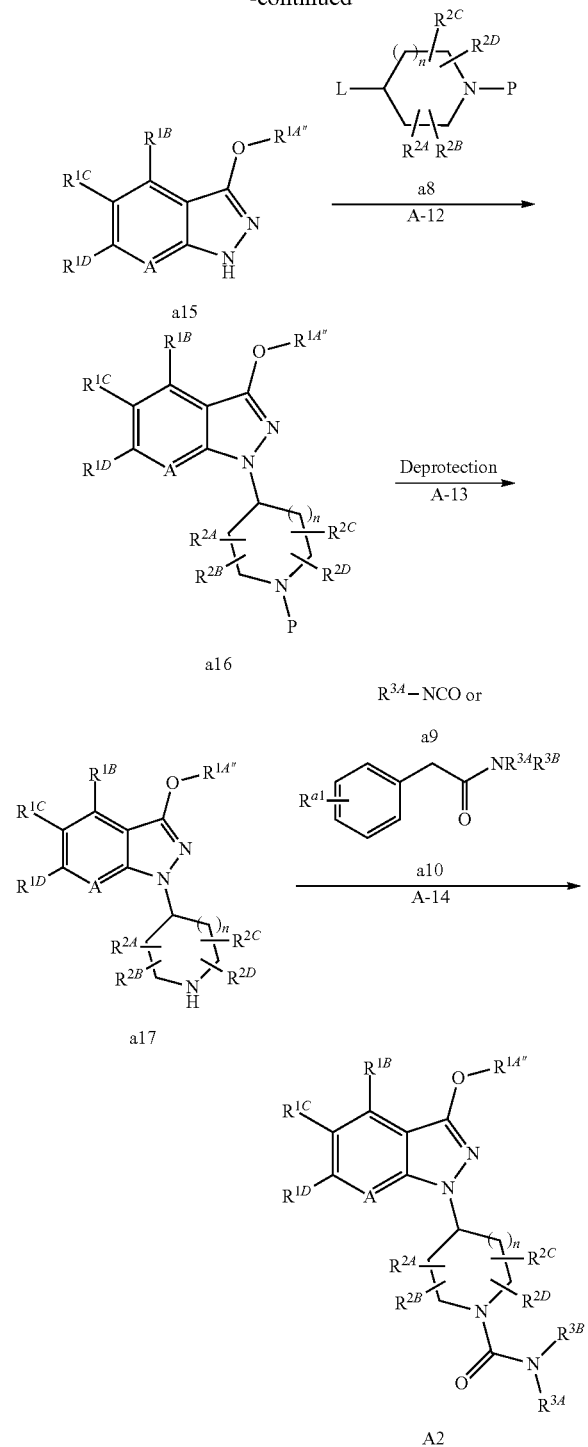

wherein

A, $R^{1B}$ to $R^{1D}$, $R^{2A}$ to $R^{2D}$, $R^{3A}$, $R^{3B}$ and n are as defined in Term 1, $R^{14''}$ is an optionally-substituted $C_{1-6}$ alkyl, and P is a protecting group for the amino group.

2-Aminobenzoate derivative (Compound a11) can be synthesized by methods disclosed in publications such as Chemistry Letters, 2009, 38 (3), 200-201 and Organic Process Research & Development, 2009, 13 (4), 698-705, or be commercially available.

(Step A-8)

In this step, Compound a11 is reacted with sodium nitrite and then sodium thiosulfate in the presence of any acid in a suitable solvent to give Compound a12. The acid used herein is selected from mineral acids such as hydrochloric acid, nitric acid and sulfuric acid, and preferably hydrochloric acid. The solvent used herein may be selected from those exemplified later, and preferably water. The reaction temperature herein depends on factors such as the types of starting compound and reagents, and it is typically −50° C. to 150° C., preferably −30° C. to 100° C., and more preferably −10° C. to 60° C. The reaction time herein is typically about 1 to 48 hours, preferably 1 to 24 hours, and more preferably 1 to 16 hours.

(Step A-9)

In this step, the hydrogen atom at 1-position of the indazole in Compound a12 prepared in Step A-8 is replaced with a protecting group for the amino group (defined as "P") to give Compound a13. The step herein can be carried out according to methods disclosed in, for example, Protective Groups in Organic Synthesis (Theodora W. Greene, Peter G. M. Wuts, John Wiley & Sons, Inc., 1999). The reaction temperature herein depends on factors such as the types of starting compound and reagents, and it is typically −30° C. to 200° C., preferably 0° C. to 150° C., and more preferably 0° C. to 60° C. The reaction time herein is typically about 1 to 48 hours, preferably 1 to 24 hours, and more preferably 1 to 16 hours.

(Step A-10)

In this step, Compound a13 prepared in Step A-9 is reacted with any alkylating agent in the presence of any base in a suitable solvent to give Compound a14. The electrophile used herein may be, for example, 1-methyl-1-nitrosourea, ethyl iodide, or isopropyl iodide. The base used herein may be selected from those exemplified later, and preferably potassium carbonate, cesium carbonate, silver carbonate or the like. The solvent used herein is preferably acetonitrile or diethyl ether. The reaction temperature herein depends on factors such as the types of starting compound and reagents, and it is typically −30° C. to 200° C., preferably 0° C. to 150° C., and more preferably 0° C. to 100° C. The reaction time herein is typically about 1 to 48 hours, preferably 1 to 24 hours, and more preferably 1 to 16 hours.

(Step A-11)

In this step, the protecting group for the amino group of Compound a14 prepared in Step A-10 (defined as "P") is deprotected to give Compound a15. The step herein can be carried out according to methods disclosed in, for example, Protective Groups in Organic Synthesis (Theodora W. Greene, Peter G. M. Wuts, John Wiley & Sons, Inc., 1999). The reaction temperature herein depends on factors such as the types of starting compound and reagents, and it is typically −30° C. to 200° C., preferably 0° C. to 150° C., and more preferably 0° C. to 60° C. The reaction time herein is typically about 1 to 48 hours, preferably 1 to 24 hours, and more preferably 1 to 16 hours.

(Step A-12)

In this step, Compound a15 prepared in Step A-11 is converted to Compound a16 according to the conditions in Step A-5.

(Step A-13)

In this step, Compound a16 prepared in Step A-12 is converted to Compound a17 according to the conditions in Step A-6.

(Step A-14)

In this step, Compound a17 prepared in Step A-13 is converted to compound A2 according to the conditions in Step A-7.

Process B

Among the compounds of Formula (I), those wherein X—Y—Z is N—CO—NR$^4$ as shown by Formula B1 (i.e. Compound B1) can be prepared by, for example, the following process:

Process C$^1$

Among the compounds of Formula (I), those wherein X—Y—Z is CR$^{2E}$—NR$^5$—COR$^4$ as shown by Formulae C1 and C2 (i.e. Compounds C1 and C2) can be prepared by, for example, the following process:

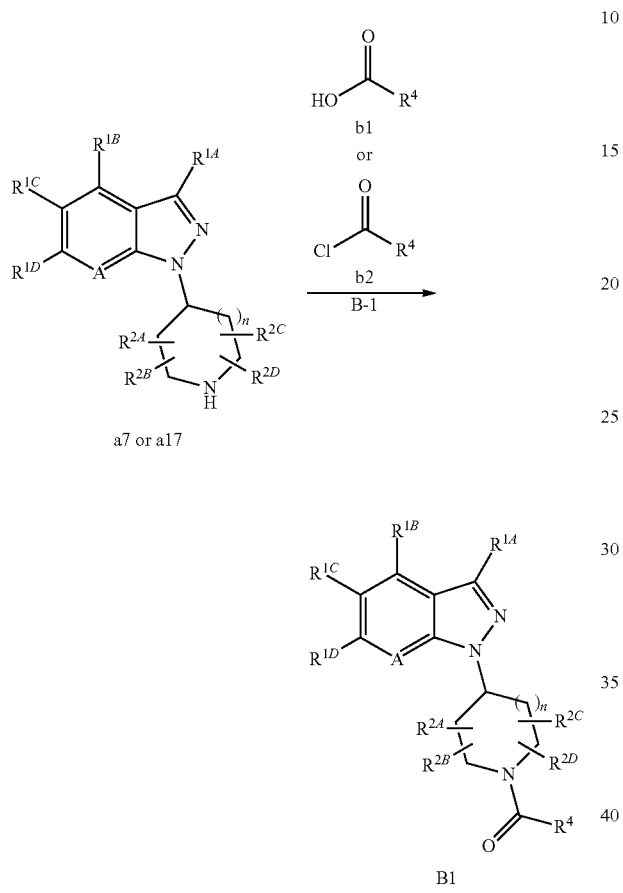

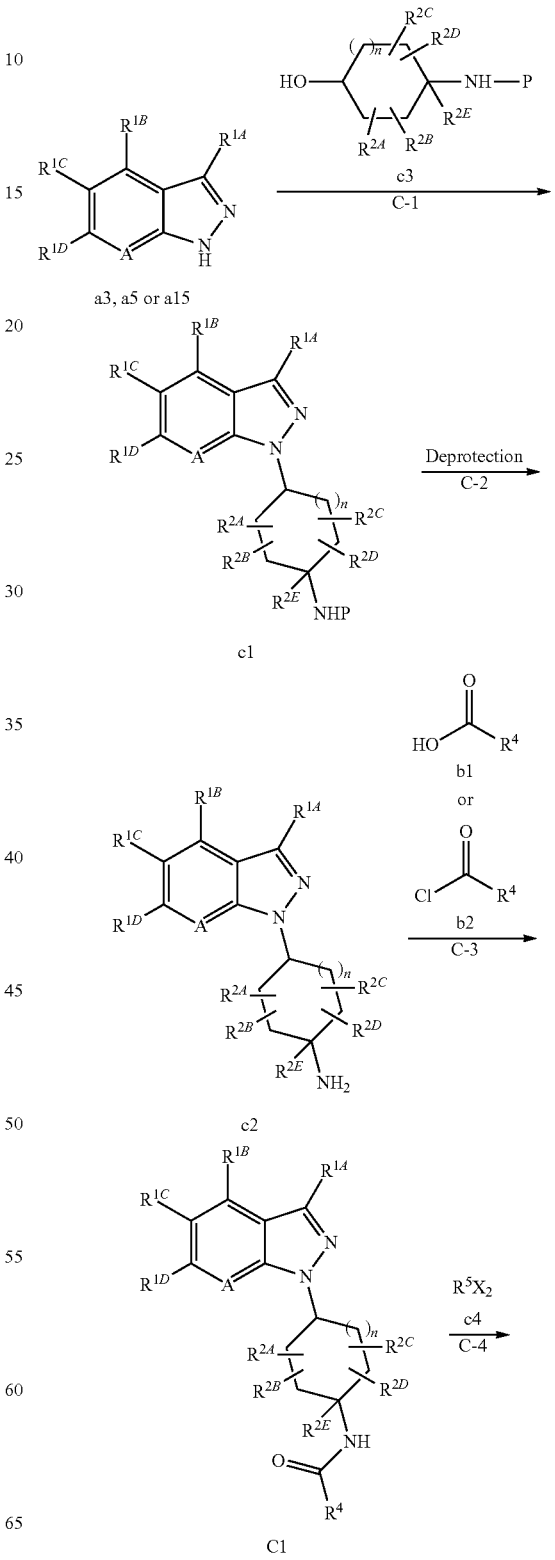

wherein A, R$^{1A}$ to R$^{1D}$, R$^{2A}$ to R$^{2D}$, R$^4$ and n are as defined in Term 1.

(Step B-1)

In this step, Compound a7 or a17 prepared in Step A-6 or A-13 respectively is reacted with Compound b1 or b2 in the presence of any condensing agent or base in a suitable solvent to give compound B1. The condensing agent used herein includes various types used in conventional methods, and preferably 1-ethyl-3-(3-dimethylaminopropyl)carbodiimide (including hydrochloride thereof). The base used herein may be selected from those exemplified later and preferably diisopropylethylamine or triethylamine. The solvent used herein may be selected from those exemplified later, and preferably dimethylformamide or tetrahydrofuran. The reaction temperature herein depends on factors such as the types of starting compound and reagents, and it is typically −30° C. to 200° C., preferably 0° C. to 150° C., and more preferably 0° C. to 80° C. The reaction time herein is typically about 1 to 48 hours, preferably 1 to 24 hours, and more preferably 1 to 16 hours.

-continued

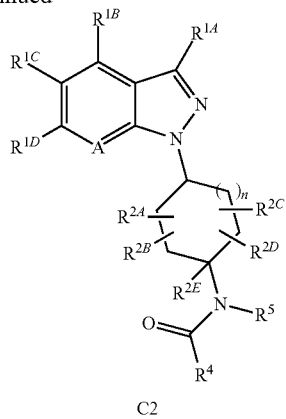

C2 wherein

A, $R^{1A}$ to $R^{1D}$, $R^{2A}$ to $R^{2E}$, $R^4$, $R^5$ and n are as defined in Term 1, $X_2$ is a leaving group such as a halogen, and P is a protecting group for the amino group.

(Step C-1)

In this step, Compound a3, a5 or a15 is reacted with Cyclohexylalcohol c3 by Mitsunobu reaction in the presence of an azo compound analog and an organophosphorus compound to give Compound c1. The azo compound analog used herein includes, for example, diethylazodicarboxylate and diisopropylazodicarboxylate. The organophosphorus compound used herein is preferably triphenylphosphine or the like. The solvent used herein may be selected from those exemplified later, and preferably tetrahydrofuran. Similar reactions of the step herein are disclosed in, for example, Synlett, 2009, 16, 2673-2675 and Bioorganic & Medicinal Chemistry Letters, 2007, 17 (7), 2036-2042. In addition, Compound c3 can be synthesized by methods disclosed in publications such as WO 2011/035159 and WO 2010/032009, or be commercially available. The reaction temperature herein depends on factors such as the types of starting compound and reagents, and it is typically −30° C. to 200° C., preferably 0° C. to 150° C., and more preferably 0° C. to 100° C. The reaction time herein is typically about 1 to 48 hours, preferably 1 to 24 hours, and more preferably 1 to 16 hours.

(Step C-2)

In this step, the protecting group for the amino group of Compound c1 prepared in Step C-1 (defined as "P") is deprotected to give Compound c2. The step herein can be carried out according to methods disclosed in, for example, Protective Groups in Organic Synthesis (Theodora W. Greene, Peter G. M. Wuts, John Wiley & Sons, Inc., 1999). The reaction temperature herein depends on factors such as the types of starting compound and reagents, and it is typically −30° C. to 200° C., preferably 0° C. to 150° C., and more preferably 0° C. to 60° C. The reaction time herein is typically about 1 to 48 hours, preferably 1 to 24 hours, and more preferably 1 to 16 hours.

(Step C-3)

In this step, Compound c2 prepared in Step C-2 is converted to Compound C1 according to the conditions in Step B-1.

(Step C-4)

In this step, Compound C1 prepared in Step C-3 is reacted with Compound c4 in the presence of any base in a suitable solvent to give Compound C2. The base used herein may be selected from those exemplified later, and preferably sodium hydride or diisopropylamine. The solvent used herein may be selected from those exemplified later, and preferably dimethylformamide or tetrahydrofuran. The reaction temperature herein depends on factors such as the types of starting compound and reagents, and it is typically −30° C. to 200° C., preferably 0° C. to 150° C., and more preferably 0° C. to 80° C. The reaction time herein is typically about 1 to 48 hours, preferably 1 to 24 hours, and more preferably 1 to 16 hours.

Process $C^2$

Among the compounds of Formula (I), those wherein X—Y—Z is $CR^{2E}$—$NR^5$—$CONR^{3A}R^{3B}$ as shown by Formulae C3 and C4 (i.e. Compounds C3 and C4) can be prepared by, for example, the following process:

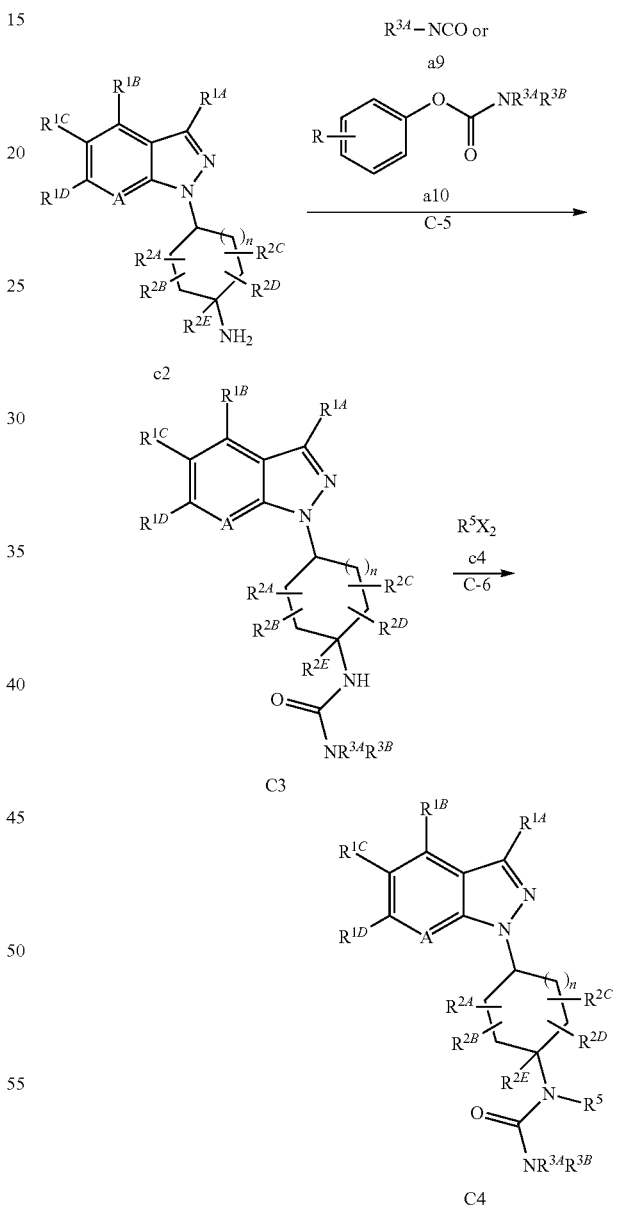

wherein

A, $R^{1A}$ to $R^{1D}$, $R^{2A}$ to $R^{2E}$, $R^{3A}$, $R^{3B}$, $R^5$ and n are as defined in Term 1, $X_2$ is a leaving group such as a halogen, and P is a protecting group for the amino group.

(Step C-5)

In this step, Compound c2 prepared in Step C-2 is converted to Compound C3 according to the conditions in Step A-14.

(Step C-6)

In this step, Compound C3 prepared in Step C-5 is converted to Compound C4 according to the conditions in Step C-4.

Process D

Among the compounds of Formula (I), those wherein X—Y—Z is $CR^{2E}$—CO—$NR^{3A}R^{3B}$ as shown by Formula D1 (i.e. Compound D1) can be prepared by, for example, the following process:

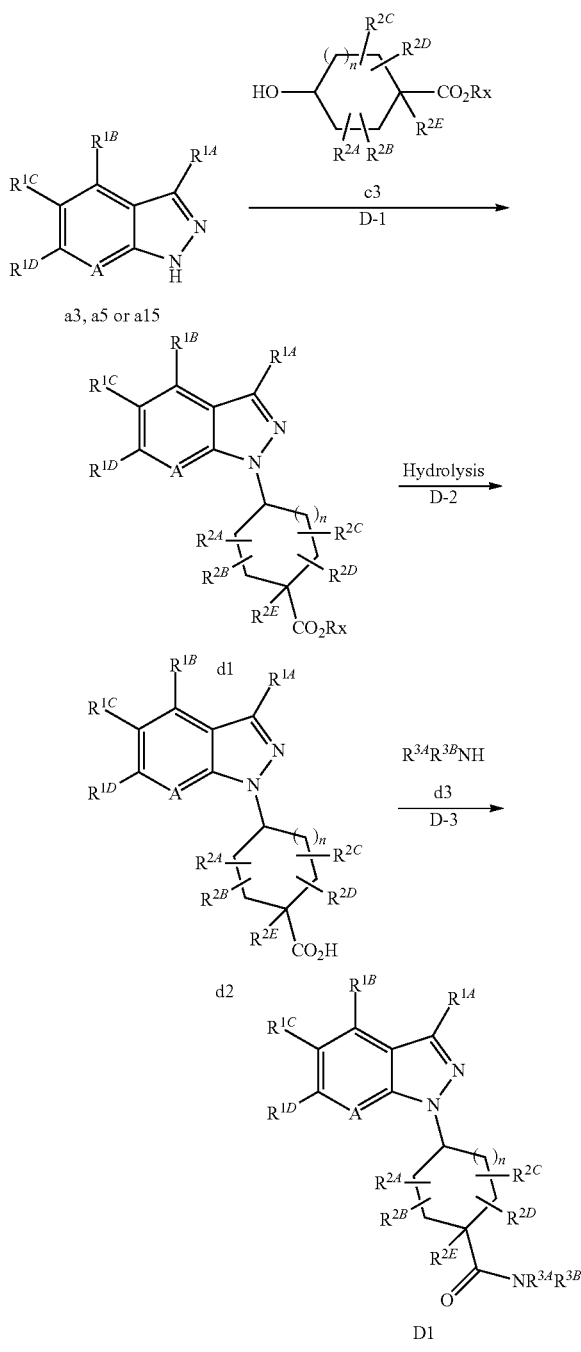

wherein

A, $R^{1A}$ to $R^{1D}$, $R^{2A}$ to $R^{2E}$, $R^{3A}$, $R^{3B}$ and n are as defined in Term 1, and Rx is a protecting group for the carboxyl group.

(Step D-1)

In this step, Compound a3, a5 or a15 is converted to Compound d1 according to the conditions in Step C-1.

(Step D-2)

In this step, the ester Compound d1 prepared in Step D-1 is converted to a corresponding carboxylic Compound d2. The step herein can be carried out according to methods disclosed in, for example, Protective Groups in Organic Synthesis (Theodora W. Greene, Peter G. M. Wuts, John Wiley & Sons, Inc., 1999). The reaction temperature herein depends on factors such as the types of starting compound and reagents, and it is typically −30° C. to 200° C., preferably 0° C. to 150° C., and more preferably 0° C. to 60° C. The reaction time herein is typically about 1 to 48 hours, preferably 1 to 24 hours, and more preferably 1 to 16 hours.

(Step D-3)

In this step, Compound d2 prepared in Step D-2 is reacted with Compound d3 in the presence of any condensing agent in a suitable solvent to give compound D1. The condensing agent used herein includes various types used in conventional methods, and preferably 1-ethyl-3-(3-dimethylaminopropyl)carbodiimide (including hydrochloride thereof). The solvent used herein may be selected from those exemplified later. The reaction temperature herein depends on factors such as the types of starting compound and reagents, and it is typically −30° C. to 200° C., preferably 0° C. to 150° C., and more preferably 0° C. to 80° C. The reaction time herein is typically about 1 to 48 hours, preferably 1 to 24 hours, and more preferably 1 to 16 hours.

The base used in each step in each of the above-shown processes can be selected depending on various factors such as the type of reaction and starting compound; and includes, for example, alkaline bicarbonates such as sodium bicarbonate and potassium bicarbonate, alkaline carbonates such as sodium carbonate and potassium carbonate, metal hydrides such as sodium hydride and potassium hydride, alkali metal hydroxides such as sodium hydroxide and potassium hydroxide, alkali metal alkoxides such as sodium methoxide and sodium t-butoxide, organometallic bases such as butyllithium and lithium diisopropylamide, and organic bases such as triethylamine, diisopropylethylamine, pyridine, 4-dimethylaminopyridine (DMAP) and 1,8-diazabicyclo[5.4.0]-7-undecene (DBU).

The solvent used in each step in the above-shown processes can be optionally selected depending on various factors such as the type of reaction and starting compound; and includes, for example, alcohols such as methanol, ethanol and isopropanol, ketones such as acetone and methyl ketone, halogenated hydrocarbons such as methylene chloride and chloroform, ethers such as tetrahydrofuran (THF) and dioxane, aromatic hydrocarbons such as toluene and benzene, aliphatic hydrocarbons such as hexane and heptane, esters such as ethyl acetate and propyl acetate, amides such as N,N-dimethylformamide (DMF) and N-methyl-2-pyrrolidone, sulfoxides such as dimethylsulfoxide (DMSO), and nitriles such as acetonitrile. These solvents can be used alone or in combination with two or more. In addition, organic bases may also be used as the solvent, depending on the type of reaction.

The present compound of Formula (I) or an intermediate thereof can be isolated and purified by well-known methods such as extraction, partition, reprecipitation, column chromatography (e.g. silica gel column chromatography, ion exchange column chromatography and preparative liquid chromatography) and recrystallization. The recrystallization solvent used herein includes, for example, alcohol solvents such as methanol, ethanol and 2-propanol, ether solvents such as diethyl ether, ester solvents such as ethyl acetate, aromatic hydrocarbon solvents such as benzene and toluene, ketone solvents such as acetone, halogen solvents such as dichloromethane and chloroform, hydrocarbon solvents such as hexane, aprotic solvents such as dimethylformamide and acetonitrile, water, and a mixed solvent selected from two or more of the above-listed solvents. Other purification methods, for example, those disclosed in Experimental Chemistry Textbook Vol. 1 (the Chemical Society of Japan, ed., Maruzen) can also be used herein.

The present compound of Formula (I) or a pharmaceutically acceptable salt thereof may exhibit chirality or contain a substituent with an asymmetric carbon, which can exist as optical isomers. The present compound includes a mixture of each of the isomers and an isolated single isomer, which can be prepared according to a conventional process, for example, using a starting material with an asymmetric center or introducing chirality during the process. In detail, in order to obtain an optical isomer, it can be prepared by using optically active compounds as a starting material or optically resolving the mixture at an appropriate stage during the process. The optical resolution method used herein includes, for example, an isolation technique via diastereomeric salt formed as follows. When the compound of Formula (I) or an intermediate thereof has a basic group, such diastereomeric salt can be formed with optically active acids such as monocarboxylic acids (e.g. mandelic acid, N-benzyloxyalanine, and lactic acid), dicarboxylic acids (e.g. tartaric acid, o-diisopropylidene tartaric acid, and malic acid) and sulfonic acids (e.g. camphor sulfonic acid and bromocamphor sulfonic acid) in an inert solvent such as alcohol solvents (e.g. methanol, ethanol, and 2-propanol), ether solvents (e.g. diethyl ether), ester solvents (e.g. ethyl acetate), hydrocarbon solvents (e.g. toluene), aprotic solvents (e.g. acetonitrile), and a mixed solvent selected from two or more of the above-listed solvents. When the present compound of Formula (I) or an intermediate thereof has an acidic group such as a carboxyl group, such diastereomeric salt can be formed with optically active amines such as organic amines (e.g. 1-phenylethylamine, kinin, quinidine, cinchonidine, cinchonine and strychnine). Thus, it is possible to resolve a mixture of optical isomers via the resolution of such diastereomeric salt.

The present compound can be a novel medicament for treating and/or preventing a disease due to an abnormality of the intracellular signaling mediated by acetylcholine, and in particular, nervous system diseases, psychiatric diseases, and inflammatory diseases [e.g. dementia, schizophrenia, CIAS (cognitive impairment associated with schizophrenia), Alzheimer's disease, Down's syndrome, attention deficit disorder, and cerebral angiopathy]. The administration route of the present compound may be any of oral, parenteral and rectal ones; and the daily dosage thereof may vary depending on the type of compound, administration method, symptom/age of the patient, and other factors. For example, in case of oral administration, the present compound can be administered to human beings or mammals at typically about 0.01 mg to 1000 mg and preferably about 0.1 mg to 500 mg per kg of body weight as a single or multiple doses. In case of parenteral administration such as intravenous injection, the present compound can be administered to human beings or mammals at typically about 0.01 mg to 300 mg and preferably about 1 mg to 100 mg per kg of body weight.

The dosage forms of the present compound include, for example, tablets, capsules, granules, powders, syrups, suspensions, injections, suppositories, eye drops, ointments, embrocations, adhesive skin patches, and inhalants. These formulations can be prepared according to conventional methods. In addition, liquid formulations may be in a form wherein the present compound is dissolved or suspended in water, appropriate aqueous solutions, or other appropriate vehicles at the time of use. Tablets and granules may be coated according to known methods. Furthermore, the formulations may comprise additional ingredients which are useful for the treatment.

The present compound can be used in combination with a drug classified as atypical antipsychotic drugs. The atypical antipsychotic drugs include, for example, olanzapine, risperidone, paliperidone, quetiapine, ziprasidone, aripiprazole, asenapine, iloperidone, clozapine, sertindole, blonanserin and lurasidone.

The temperature for forming the salt is in the range of room temperature to boiling point of a solvent as used. In order to improve the optical purity, it is desirable that the temperature is once raised to around the boiling point of the solvent. The precipitated salt is collected on a filter; and if necessary, the filtration may be carried out under cooled conditions to improve the yield. The appropriate amount of an optically active acid or amine used herein is about 0.5 to about 2.0 equivalents, preferably about 1 equivalent per the reactant. If necessary, the crystal can be recrystallized from an inert solvent such as alcohol solvents (e.g. methanol, ethanol and 2-propanol), ether solvents (e.g. diethyl ether), ester solvents (e.g. ethyl acetate), hydrocarbon solvents (e.g. toluene), aprotic solvents (e.g. acetonitrile), and a mixed solvent selected from two or more of the above-listed solvents to give the optically active salt in high purity. In addition, if necessary, it is also possible to treat the optically-resolved salt with an acid or base by a conventional method to give a free form thereof.

EXAMPLE

Hereinafter, the present invention is further explained in detail in Reference Examples, Examples and Test Examples, but the present invention should not be limited thereto. In addition, the compounds were identified by, for example, elementary analysis, mass spectra, high performance liquid chromatograph-mass spectrometer, LCMS, IR spectra, NMR spectra, and high performance liquid chromatography (HPLC).

For the purpose of simplifying expressions, the following abbreviations may be optionally used in Reference Examples, Examples and the tables thereof. When referring to substituents, Me and Ph are abbreviations of methyl and phenyl respectively. TFA is an abbreviation of trifluoroacetic acid. The following abbreviations are used in NMR data.

s: singlet
d: doublet
dd: doublet of doublet
t: triplet
td: triplet of doublet
q: quartet
m: multiplet
br: broad
brs: broad singlet
brs: broad multiplet
J: coupling constant The measurement conditions of LCMS by high performance liquid chromatograph-mass spectrometer are shown below. The observed value of mass spectrometry [MS(m/z)] is shown as MH+, and the retention time is shown as Rt (min).

In addition, the conditions used in measuring each of the observed value are shown as A to F:

Measurement Condition A
Detector: Agilent 1100 series for API series manufactured by Applied Biosystems
HPLC: API 150EX LC/MS system manufactured by Applied Biosystems
Column: YMC CombiScreen Hydrosphere C18 (S-5 μM, 12 nm, 4.6×50 mm)
Solvent: Solution A: 0.05% TFA/H$_2$O, Solution B: 0.05% TFA/MeOH
Gradient Condition:
    0.0-6.0 min; A/B=75:25-1:99 (linear gradient)
Flow rate: 3.5 mL/min
UV: 254 nm Measurement Condition B
Detector: HPLC: LCMS-2010EV manufactured by Shimadzu
Column: Xtimate (3 μM, 2.1×30 mm) manufactured by Welch Materials
Solvent: Solution A: 0.019% TFA/H$_2$O, Solution B: 0.038% TFA/MeOH
Gradient Condition:
    0.0-1.35 min; A/B=90:10-20:80 (linear gradient)
    1.35-2.25 min; A/B=20:80
Flow rate: 0.8 mL/min
UV: 220 nm
Column temperature: 50° C.

Measurement Condition C
Detector: Perkin-Elmer Sciex API 150EX Massspectrometer (40 eV)
HPLC: Shimadzu LC 10ATVP
Column: Shiseido CAPCELL PAK C18 ACR (S-5 μm, 4.6 mm×50 mm)
Solvent: Solution A: 0.035% TFA/CH$_3$CN, Solution B: 0.05% TFA/H$_2$O
Gradient Condition:
    0.0-0.5 min; A/B=1:99
    0.5-4.8 min; A/B=10:90-99:1 (linear gradient)
    4.8-5.0 min; A/B=99:1
Flow rate: 3.5 mL/min
UV: 220 nm
Column temperature: 40° C.

Measurement Condition D
Detector: Waters ACQUITY UltraPerfomanc LC-PDA-ELSD-SQD
Column: Waters UPLC BEH C18 1.7 m, 2.1×30 mm (Part. No. 186002349)
Solvent: Solution A: 0.05% HCOOH/H$_2$O, Solution B: CH$_3$CN
Gradient Condition:
    0.0 min; A/B=90:10
    0.0-1.3 min; A/B=90:10-5:95 (linear gradient)
Flow rate: 0.80 mL/min
UV: 220, 254 nm
Column temperature: 40° C.

Measurement Condition E
Detector: Shimadzu LCMS-2020
Column: Phenomenex Kinetex (1.7 μm C18, 50 mm×2.10 mm)
Solvent: Solution A: MeOH, Solution B: 0.05% TFA/H$_2$O
Gradient Condition:
    0.0 min; A/B=30:70
    0.0-1.9 min; A/B=99:1
    1.9-3.0 min; A/B=30:70
Flow rate: 0.5 mL/min
UV: 220 nm Column temperature: 40° C.
Measurement Condition F
Detector: Waters ACQUITY UPLC
Column: Waters ACQUITY UPLC BEH Phenyl 1.7 μm 2.1× 50 mm
Solvent: Solution A: 0.05% HCOOH/H$_2$O, Solution B: CH$_3$CN
Gradient Condition:
    0.0-1.3 min; A/B=90:10-1:99 (linear gradient)
    1.3-1.5 min; A/B=1:99
    1.5-2.0 min; A/B=90:10
Flow rate: 0.75 mL/min
UV: 220, 254 nm
Column temperature: 50° C.

REFERENCE EXAMPLE 1

5-methyl-1-(4-piperidyl)-1H-indazole hydrochloride

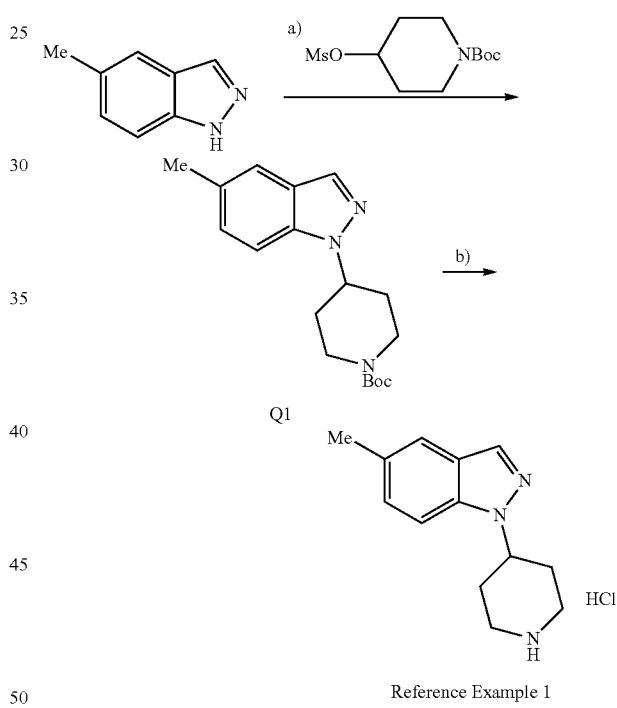

a) Preparation of tert-butyl 4-(5-methyl-1H-indazol-1-yl)piperidine-1-carboxylate (Compound Q1)

To a solution of 5-methylindazole (901 mg) in DMF (10 mL) was added sodium hydride (327 mg) at 0° C., and the mixture was stirred with heating at 40° C. for 30 minutes. To the reaction solution was added tert-butyl 4-(methylsulfonyloxy)piperidine-1-carboxylate (2.28 g), and the mixture was stirred with heating at 90° C. for 19 hours. Then, the mixture was partitioned between ethyl acetate and water, and the organic layer was washed with brine and dried over Na$_2$SO$_4$. The residue was purified by silica gel column chromatography (ethyl acetate:hexane=2:5 as the eluting solvent) to give Compound Q1 (1.04 g).

$^1$H-NMR (400 MHz, CDCl$_3$): 1.47 (9H, s), 2.00 (2H, m), 2.21 (2H, m), 2.43 (3H, s), 2.93 (2H, br), 4.28 (2H, br), 4.50 (1H, m), 7.19 (1H, d, J=8.0 Hz), 7.32 (1H, d, J=8.0 Hz), 7.48 (1H, s), 7.89 (1H, s).

b) Preparation of 5-methyl-1-(4-piperidyl)-1H-indazole hydrochloride (Reference Example 1)

To a solution of Compound Q1 (1.04 g) in chloroform (20 mL) was added 4 mol/L HCl-dioxane (3.3 mL), and the mixture was stirred at room temperature for 7 hours. Then, the solvent was evaporated under reduced pressure to give Reference Example 1 (720 mg).

REFERENCE EXAMPLE 2

3-ethoxy-5-ethyl-1-(piperidin-4-yl)-1H-indazole hydrochloride

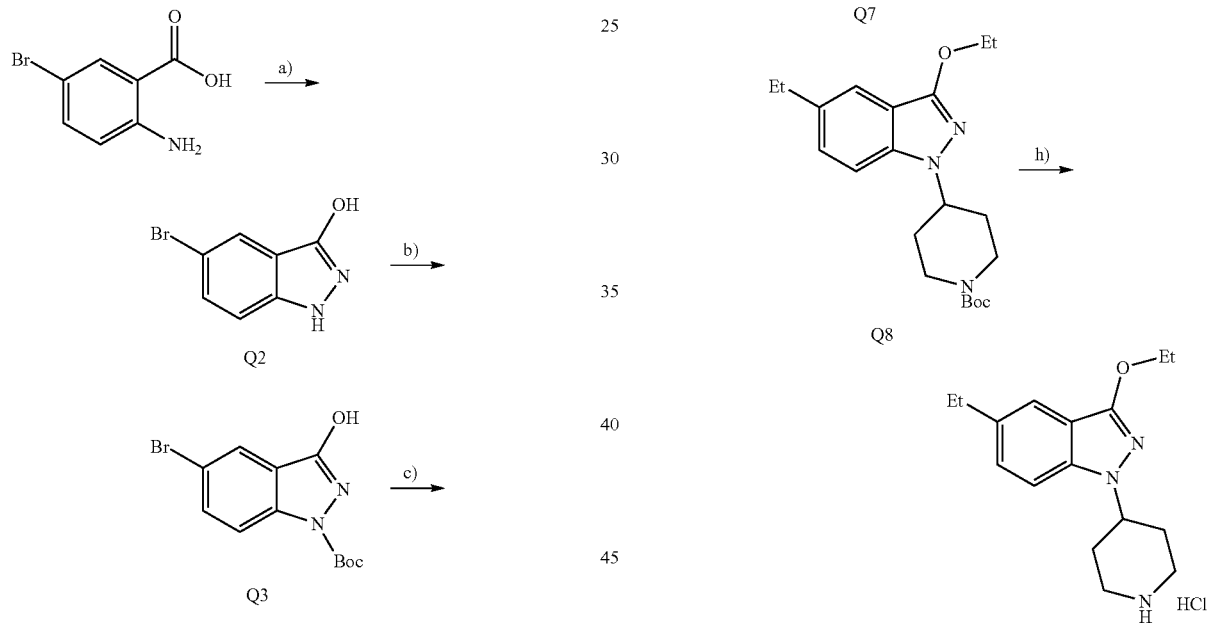

a) Preparation of 5-bromo-1H-indazol-3-ol (Compound Q2)

To a solution of 2-amino-5-bromobenzoic acid (50 g) in water (200 mL) was added HCl (46 mL). To the mixture was added aqueous NaNO$_2$ solution (17.7 g/37 mL) at 0° C., and the mixture was stirred at 0° C. for 30 minutes. To the reaction solution was added dropwise aqueous Na$_2$SO$_3$ solution (79.3 g/200 mL) at 0° C., and the mixture was stirred at room temperature for 2 hours. To the mixture was added HCl (70 mL), and the mixture was stirred at room temperature for 18 hours and then at 80° C. for 4 hours. The precipitated solid was dissolved by basifying the reaction solution, and then the solution was acidified to precipitate a solid. The solid was collected by filtration and dried under reduced pressure to give Compound Q2 (36 g).

¹H-NMR (400 MHz, d-DMSO): 7.28 (1H, d, J=8.0 Hz), 7.39 (1H, d, J=8.0 Hz), 7.82 (1H, s), 10.67 (1H, s), 11.75 (1H, s).

b) Preparation of tert-butyl 5-bromo-3-hydroxy-1H-indazole-1-carboxylate (Compound Q3)

To a solution of Compound Q2 (5.00 g) in acetonitrile (50 mL) were added under nitrogen atmosphere triethylamine (3.60 g) and 4-N,N-dimethylaminopyridine (144 mg), and the mixture was stirred at room temperature for 10 minutes. To the mixture was added di-tert-butyl dicarbonate (5.14 g), and the mixture was stirred for 10 hours at room temperature. The solvent was removed out, the mixture was partitioned between ethyl acetate and water, and the organic layer was washed with brine and dried over $Na_2SO_4$. The solvent was evaporated under reduced pressure to give Compound Q3 (4.5 g).

¹H-NMR (400 MHz, d-DMSO): 1.61 (9H, s), 7.73 (1H, dd, J=8.0 Hz, 1.6 Hz), 7.94 (2H, m).

c) Preparation of tert-butyl 5-bromo-3-ethoxy-1H-indazole-1-carboxylate (Compound Q4)

A solution of Compound Q3 (15.0 g), ethyl iodide (7.5 g) and cesium carbonate (31.3 g) in acetonitrile (250 mL) was stirred with heating at 80° C. for 16 hours. The solvent was removed out, the mixture was partitioned between ethyl acetate and water, and the organic layer was washed with brine and dried over $Na_2SO_4$. The residue was purified by silica gel column chromatography (petroleum ether:ethyl acetate=30:1 as the eluting solvent) to give Compound Q4 (9.00 g).

¹H-NMR (400 MHz, $CDCl_3$): 1.50 (3H, t, J=7.2 Hz), 1.72 (9H, s), 4.56 (2H, q, J=7.2 Hz), 7.60 (1H, dd, J=8.0 Hz, 1.6 Hz), 7.85 (2H, m)

d) Preparation of 5-bromo-3-ethoxy-1H-indazole (Compound Q5)

To a solution of Compound Q4 (7.60 g) in ethyl acetate (50 mL) was added 4 mol/L HCl-ethyl acetate (50 mL), and the mixture was stirred at room temperature for 8 hours. Then, the solvent was evaporated under reduced pressure, and the residue was washed with ethyl acetate, collected by filtration and dried under reduced pressure to give Compound Q5 (6.20 g).

¹H-NMR (400 MHz, $CD_3OD$): 1.48 (3H, t, J=7.2 Hz), 4.44 (2H, q, J=7.2 Hz), 7.31 (1H, d, J=9.2 Hz), 7.49 (1H, d, J=9.2 Hz), 7.80 (1H, s).

e) Preparation of tert-butyl 4-(5-bromo-3-ethoxy-1H-indazol-1-yl)piperidine-1-carboxylate (Compound Q6)

To a solution of the above-obtained Compound Q5 (2.03 g) in dehydrated DMF (120 mL) was added under nitrogen atmosphere sodium hydride (1.17 g), and the mixture was stirred at 0° C. for 30 minutes. To the reaction solution was added tert-butyl 4-(methylsulfonyloxy)piperidine-1-carboxylate (4.08 g), and the mixture was stirred with heating at 90° C. for 16 hours. Then, the mixture was partitioned between ethyl acetate and water, and the organic layer was washed with brine and dried over $Na_2SO_4$. The residue was purified by silica gel column chromatography (ethyl acetate:petroleum ether=1:30 as the eluting solvent) to give Compound Q6 (3.10 g).

¹H-NMR (400 MHz, $CDCl_3$): 1.41 (3H, t, J=7.2 Hz), 1.45 (3H, s), 1.90 (2H, m), 2.15 (2H, m), 2.93 (2H, m), 4.28 (3H, m), 4.40 (2H, q, J=7.2 Hz), 7.14 (1H, d, J=9.2 Hz), 7.39 (1H, dd, J=9.2 Hz, 1.6 Hz), 7.79 (1H, d, J=1.6 Hz).

f) Preparation of tert-butyl 4-(3-ethoxy-5-vinyl-1H-indazol-1-yl)piperidine-1-carboxylate (Compound Q7)

A solution of the above-obtained Compound Q6 (2.40 g), 2,4,6-trivinylcyclotriboroxan (1.09 g), cesium carbonate (5.51 g), 1,1'-bis(diphenylphosphino)ferrocene palladium dichloride (0.83 g) in dioxane (50 mL)-water (5 mL) was stirred under nitrogen atmosphere at 90° C. for 16 hours. Then, the solvent was removed out, the mixture was partitioned between dichloromethane and water, and the organic layer was washed with brine and dried over $Na_2SO_4$. The residue was purified by silica gel column chromatography (ethyl acetate:petroleum ether=1:40 as the eluting solvent) to give Compound Q7 (2.00 g).

¹H-NMR (400 MHz, $CDCl_3$): 1.49 (12H, m), 1.90 (2H, m), 2.19 (2H, m), 2.93 (2H, m), 4.28 (3H, m), 4.43 (2H, q, J=7.2 Hz), 5.16 (1H, d, J=11.0 Hz), 5.69 (1H, d, J=17.2 Hz), 6.80 (1H, dd, J=17.2 Hz, 11.0 Hz), 7.20 (1H, d, J=8.8 Hz), 7.49 (1H, dd, J=8.8 Hz, 1.6 Hz), 7.63 (1H, d, 1.6 Hz).

g) Preparation of tert-butyl 4-(3-ethoxy-5-ethyl-1H-indazol-1-yl)piperidine-1-carboxylate (Compound Q8)

A solution of the above-obtained Compound Q7 (1.62 g) and palladium (II) hydroxide/carbon (162 mg) in ethanol (180 mL) was stirred under hydrogen atmosphere at room temperature for 16 hours. Then, the mixture was filtered through Celite and the solvent was removed out to give Compound Q8 (1.60 g).

¹H-NMR (400 MHz, $CDCl_3$): 1.27 (3H, t, J=7.2 Hz), 1.49 (3H, t, J=7.2 Hz), 1.51 (9H, s), 1.93 (2H, m), 2.16 (2H, m), 2.74 (2H, q, J=7.2 Hz), 2.97 (2H, m), 4.28 (3H, m), 4.43 (2H, q, J=7.2 Hz), 7.27 (2H, m), 7.63 (1H, s).

h) Preparation of 3-ethoxy-5-ethyl-1-(piperidin-4-yl)-1H-indazole (Reference Example 2)

To a solution of the above-obtained Compound Q8 (1.45 g) in ethyl acetate (15 mL) was added 4 mol/L HCl-ethyl acetate (15 mL), and the mixture was stirred at room temperature for 8 hours. Then, the solvent was evaporated under reduced pressure, and the residue was washed with ethyl acetate, collected by filtration and dried under reduced pressure to give Reference Example 2 (1.20 g).

¹H-NMR (400 MHz, $CDCl_3$): 1.28 (3H, t, J=7.2 Hz), 1.49 (3H, t, J=7.2 Hz), 2.40 (2H, br), 2.50 (2H, br), 2.74 (2H, q, J=7.2 Hz), 3.28 (2H, br), 3.75 (2H, br), 4.44 (2H, q, J=7.2 Hz), 4.58 (1H, m), 7.24 (2H, m), 7.49 (1H, s).

REFERENCE EXAMPLE 3

5-ethoxy-1-(piperidin-4-yl)-1H-indazole hydrochloride

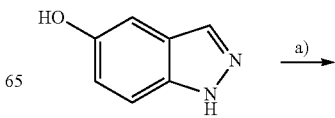

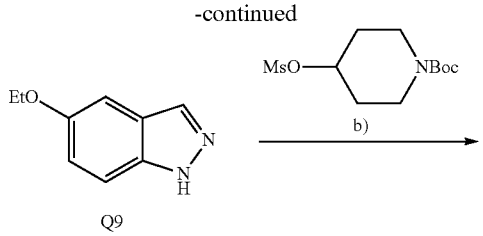

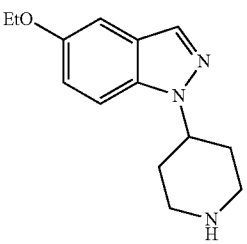

Reference Example 3 a) Preparation of 5-ethoxy-1H-indazole (Compound Q9)

To a solution of 5-hydroxyindazole (2.68 g) in DMF (50 mL) were added ethyl iodide (3.28 g) and potassium carbonate (4.16 g), and the mixture was stirred at room temperature for 1 day. Then, the mixture was partitioned between ethyl acetate and water, the organic layer was washed with brine and dried over $Na_2SO_4$, and the solvent was evaporated under reduced pressure. The residue was purified by silica gel column chromatography (ethyl acetate as the eluting solvent) to give Compound Q9 (1.95 g).

$^1$H-NMR (400 MHz, $CDCl_3$): 1.43 (3H, t, J=7.0 Hz), 4.05 (2H, q, J=7.0 Hz), 7.07 (2H, m), 7.39 (1H, m), 7.98 (1H, s).

b) Preparation of tert-butyl 4-(5-ethoxy-1H-indazol-1-yl)piperidine-1-carboxylate (Compound Q10)

To a solution of the above-obtained Compound Q9 (810 mg) in anhydrous DMF (10 mL) was added sodium hydride (220 mg) at 0° C., and the mixture was stirred with heating at 40° C. for 30 minutes. To the reaction solution was added tert-butyl 4-(methylsulfonyloxy)piperidine-1-carboxylate (1.54 g), and the mixture was stirred with heating at 90° C. for 16 hours. Then, the mixture was partitioned between ethyl acetate and water, and the organic layer was washed with brine and dried over $Na_2SO_4$. The residue was purified by silica gel column chromatography (ethyl acetate:hexane=1:3 as the eluting solvent) to give Compound Q10 (521 mg).

$^1$H-NMR (400 MHz, $CDCl_3$): 1.43 (3H, t, J=7.0 Hz), 1.46 (9H, s), 1.99 (2H, m), 2.17 (2H, m), 2.91 (2H, m), 4.04 (2H, q, J=7.0 Hz), 4.28 (2H, br), 4.50 (1H, m), 7.04 (2H, m), 7.33 (1H, m), 7.87 (1H, s).

c) Preparation of 5-ethoxy-1-(piperidin-4-yl)-1H-indazole hydrochloride (Reference Example 3)

To a solution of the above-obtained Compound Q10 (637 mg) in chloroform (10 mL) was added 4 mol/L HCl-ethyl acetate (1.38 mL), and the mixture was stirred at room temperature for 16 hours. Then, the solvent was evaporated under reduced pressure, and the residue was washed with ethyl acetate, collected by filtration and dried under reduced pressure to give Reference Example 3 (484 mg).

REFERENCE EXAMPLE 4 cis-4-(5-ethyl-1H-indazol-1-yl)cyclohexylamine hydrochloride

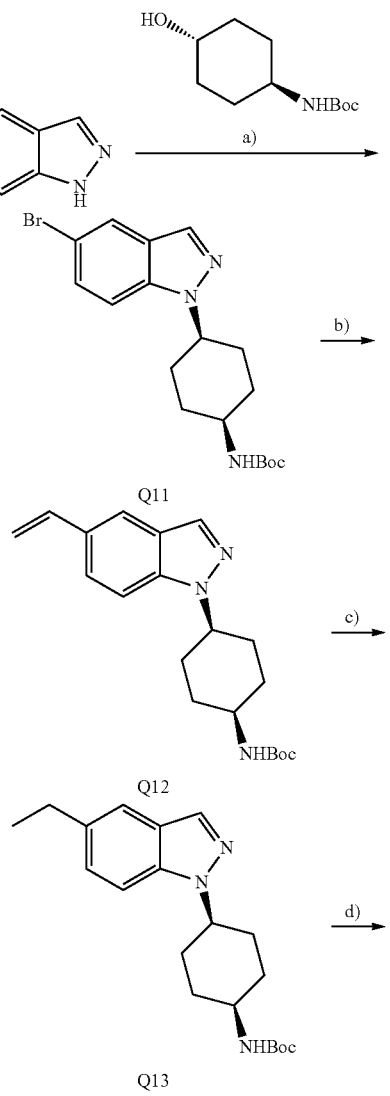

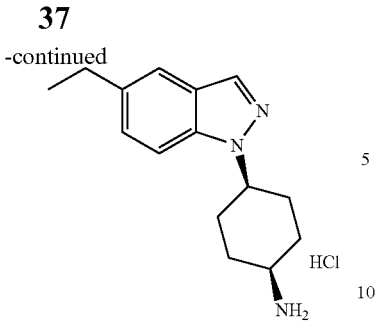

Reference Example 4 a) Preparation of tert-butyl cis-4-(5-bromo-1H-indazol-1-yl)cyclohexylcarbamate (Compound Q11)

A solution of 5-bromoindazole (15 g), tert-butyl trans-4-hydroxycyclohexylcarbamate (50 g) and triphenylphosphine (50 g) in THF was stirred at 0° C. for 15 minutes. To the reaction solution was added dropwise diisopropylazodicarboxylate (38.5 g) under nitrogen atmosphere at 0° C., and the mixture was stirred at 50° C. for 1 day. Then, the solvent was removed out, ethyl acetate (300 mL) and petroleum ether (90 mL) were added thereto, and the mixture was stirred at room temperature for 2 hours. The reaction solution was filtered, the solvent was evaporated under reduced pressure, and the residue was purified by silica gel column chromatography (ethyl acetate:petroleum ether=1:80-1:15 as the eluting solvent) to give Compound Q11 (8.00 g).

$^1$H-NMR (400 MHz, CDCl$_3$): 1.48 (9H, s), 1.80 (2H, m), 1.94-2.10 (4H, m), 2.18 (2H, m), 3.93 (1H, br), 4.45 (1H, m), 4.90 (1H, br), 7.31 (1H, d, J=9.2 Hz), 7.46 (1H, dd, J=9.2 Hz, 0.8 Hz), 7.89 (1H, d, J=0.8 Hz), 7.96 (1H, s).

b) Preparation of tert-butyl cis-4-(5-vinyl-1H-indazol-1-yl)cyclohexylcarbamate (Compound Q12)

A solution of the above-obtained Compound Q11 (5.00 g), 2,4,6-trivinylcyclotriboroxan (4.57 g), cesium carbonate (12.40 g), 1,1'-bis(diphenylphosphino)ferrocene palladium dichloride (0.75 g) in dioxane (150 mL)-water (25 mL) was stirred under nitrogen atmosphere at 90° C. for 15 hours. Then, the solvent was removed out, the mixture was partitioned between ethyl acetate and water, and the organic layer was washed with brine and dried over Na$_2$SO$_4$. The residue was purified by silica gel column chromatography (ethyl acetate:petroleum ether=1:30-1:10 as the eluting solvent) to give Compound Q12 (4.00 g).

$^1$H-NMR (400 MHz, CDCl$_3$): 1.49 (9H, s), 1.82 (2H, m), 1.96-2.12 (4H, m), 2.20 (2H, m), 3.94 (1H, br), 4.47 (1H, m), 4.92 (1H, br), 5.24 (1H, d, J=10.8 Hz), 5.75 (1H, d, J=17.6 Hz), 6.85 (1H, dd, J=17.6 Hz, 10.8 Hz), 7.40 (1H, d, J=8.8 Hz), 7.56 (1H, d, J=8.8 Hz), 7.71 (1H, s), 8.00 (1H, s).

c) Preparation of tert-butyl cis-4-(5-ethyl-1H-indazol-1-yl)cyclohexylcarbamate (Compound Q13)

A solution of the above-obtained Compound Q12 (4.00 g) and palladium (II) hydroxide/carbon (20%, 400 mg) in ethanol (100 mL) was stirred under hydrogen atmosphere at room temperature for 16 hours. Then, the mixture was filtered through Celite and the solvent was removed out to give Compound Q13 (3.50 g).

$^1$H-NMR (400 MHz, CDCl$_3$): 1.28 (3H, t, J=7.6 Hz), 1.48 (9H, s), 1.79 (2H, m), 1.95-2.10 (4H, m), 2.26 (2H, m), 2.77 (2H, q, J=7.6 Hz), 3.93 (1H, br), 4.46 (1H, m), 4.98 (1H, br), 7.26 (1H, d, J=8.8 Hz), 7.36 (1H, d, J=8.8 Hz), 7.54 (1H, s), 7.95 (1H, s).

d) Preparation of cis-4-(5-ethyl-1H-indazol-1-yl)cyclohexylamine hydrochloride (Reference Example 4)

To a solution of the above-obtained Compound Q13 (2.50 g) in ethyl acetate (15 mL) was added 4 mol/L HCl-ethyl acetate (15 mL), and the mixture was stirred at room temperature for 8 hours. Then, the solvent was evaporated under reduced pressure, and the residue was washed with ethyl acetate, collected by filtration and dried under reduced pressure to give Reference Example 4 (2.0 g).

$^1$H-NMR (400 MHz, dDMSO): 1.22 (3H, t, J=7.6 Hz), 1.87-2.02 (6H, m), 2.21 (2H, m), 2.71 (2H, q, J=7.6 Hz), 3.35 (1H, m), 4.73 (1H, m), 7.25 (1H, d, J=8.8 Hz), 7.54 (1H, s), 7.64 (1H, d, J=8.8 Hz), 7.98 (1H, s).

REFERENCE EXAMPLE 5 cis-4-(5-ethyl-1H-indazol-1-yl)cyclohexanecarboxylic acid (Reference Example 5)

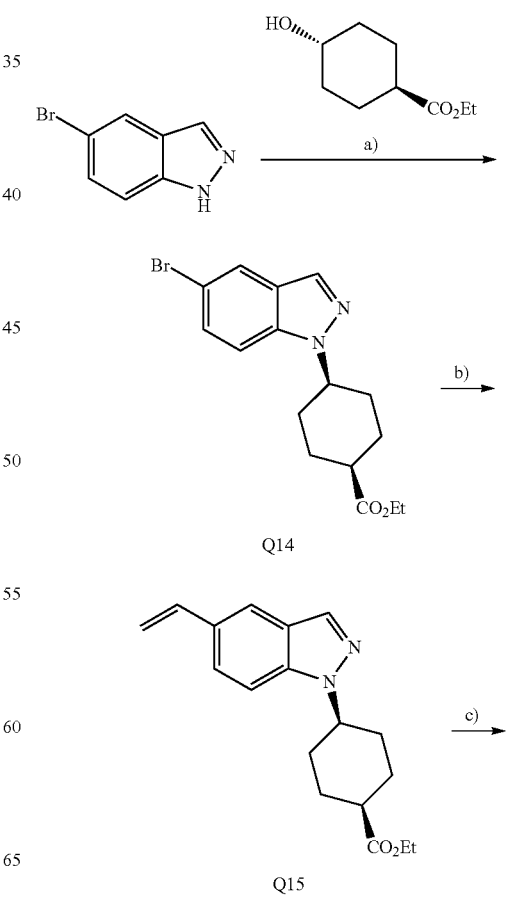

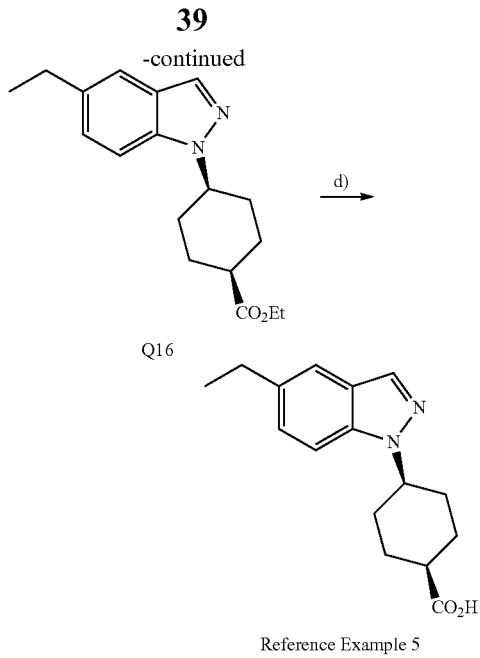

Reference Example 5 a) Preparation of ethyl cis-4-(5-bromo-1H-indazol-1-yl)cyclohexanecarboxylate (Compound Q14)

A solution of 5-bromoindazole (5.00 g), ethyl trans-4-hydroxycyclohexanecarboxylate (8.73 g), triphenylphosphine (13.3 g) in THF (150 mL) was stirred at 0° C. for 15 minutes. To the reaction solution was added dropwise diethylazodicarboxylate (9.03 g) under nitrogen atmosphere at 0° C., and the mixture was stirred at 50° C. for 13 hours. Then, the solvent was removed out, and ethyl acetate (100 mL) and petroleum ether (30 mL) were added thereto. The mixture was stirred at room temperature for 2 hours. The reaction solution was filtered, the solvent was evaporated under reduced pressure, and the residue was purified by silica gel column chromatography (ethyl acetate:petroleum ether=1:80-1:15 as the eluting solvent) to give Compound Q14 (3.50 g).

$^1$H-NMR (400 MHz, CDCl$_3$): 1.28 (3H, t, J=7.6 Hz), 1.76 (2H, m), 1.95 (2H, m), 2.27 (2H, m), 2.35 (2H, m), 2.70 (1H, m), 4.20 (1H, q, J=7.6 Hz), 4.45 (1H, m), 7.35 (1H, d, J=8.8 Hz), 7.43 (1H, d, J=8.8H), 7.85 (1H, s), 7.91 (1H, s).

b) Preparation of ethyl cis-4-(5-vinyl-1H-indazol-1-yl)cyclohexanecarboxylate (Compound Q15)

A solution of the above-obtained Compound Q14 (3.80 g), 2,4,6-trivinylcyclotriboroxan (3.90 g), cesium carbonate (10.5 g), 1,1'-bis(diphenylphosphino)ferrocene palladium dichloride (0.38 g) in dioxane (80 mL)-water (8 mL) was stirred under nitrogen atmosphere at 90° C. for 18 hours. Then, the solvent was removed out, the mixture was partitioned between ethyl acetate and water, and the organic layer was washed with brine and dried over Na$_2$SO$_4$. The residue was purified by silica gel column chromatography (ethyl acetate:petroleum ether=1:30-1:10 as the eluting solvent) to give Compound Q15 (2.10 g).

$^1$H-NMR (400 MHz, CDCl$_3$): 1.28 (3H, t, J=7.6 Hz), 1.75 (2H, m), 1.98 (2H, m), 2.25 (2H, m), 2.40 (2H, m), 2.70 (1H, m), 4.22 (1H, q, J=7.6 Hz), 4.47 (1H, m), 5.20 (1H, d, J=10.8 Hz), 5.72 (1H, d, J=17.6 Hz), 6.82 (1H, dd, J=17.6 Hz, 10.8 Hz), 7.49 (1H, d, J=8.8 Hz), 7.52 (1H, d, J=8.8H), 7.67 (1H, s), 7.95 (1H, s).

c) Preparation of ethyl cis-4-(5-ethyl-1H-indazol-1-yl)cyclohexanecarboxylate (Compound Q16)

A solution of the above-obtained Compound Q15 (3.00 g), palladium (II) hydroxide/carbon (20%, 300 mg) in ethanol (80 mL) was stirred under hydrogen atmosphere at room temperature for 16 hours. Then, the mixture was filtered through Celite and the solvent was removed out to give Compound Q16 (2.80 g).

$^1$H-NMR (400 MHz, CDCl$_3$): 1.29 (7H, m), 1.76 (2H, m), 2.00 (2H, m), 2.27 (2H, m), 2.41 (2H, m), 2.70-2.80 (3H, m), 4.25 (1H, q, J=7.6 Hz), 4.48 (1H, m), 7.23 (1H, d, J=8.8 Hz), 7.38 (1H, d, J=8.8 Hz), 7.53 (1H, s), 7.92 (1H, s).

d) Preparation of cis-4-(5-ethyl-1H-indazol-1-yl)cyclohexanecarboxylic acid (Reference Example 5)

To a solution of the above-obtained Compound Q16 (2.00 g) and lithium hydroxide (32 mg) in methanol (5 mL) were added water (5 mL) and THF (5 mL), and the mixture was stirred at room temperature for 7 hours. The solvent was removed out, water (30 mL) was added thereto, and the mixture was adjusted to pH 5 to 6 with 10% aqueous HCl solution and then extracted with ethyl acetate. The solvent was removed out to give Reference Example 5.

$^1$H-NMR (400 MHz, CDCl$_3$): 1.25 (3H, t, J=7.6 Hz), 1.76 (2H, m), 1.75 (2H, m), 1.98 (2H, m), 2.25-2.50 (4H, m), 2.70-2.83 (3H, m), 4.45 (1H, m), 7.23 (1H, d, J=8.8 Hz), 7.37 (1H, d, J=8.8 Hz), 7.51 (1H, s), 7.95 (1H, s).

REFERENCE EXAMPLE 6

5-($^2$H$_3$)methyl-1-(piperidin-4-yl)-1H-indazole hydrochloride

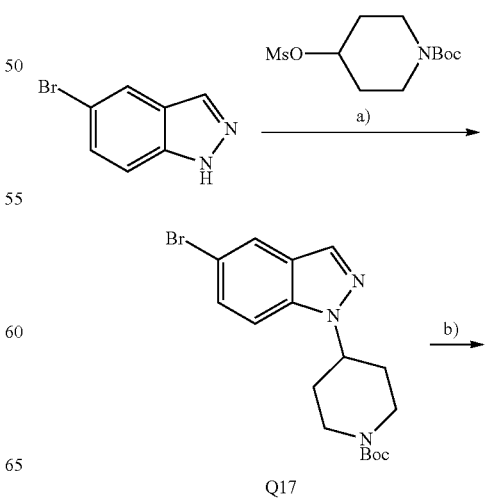

Q17

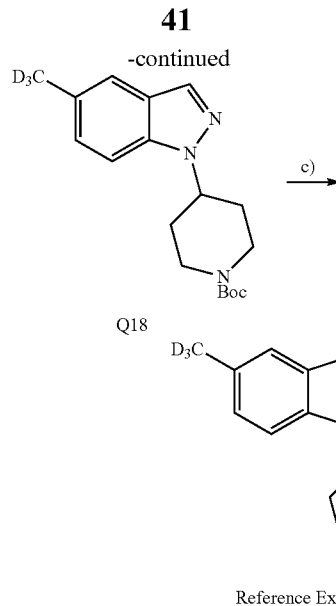

Q18

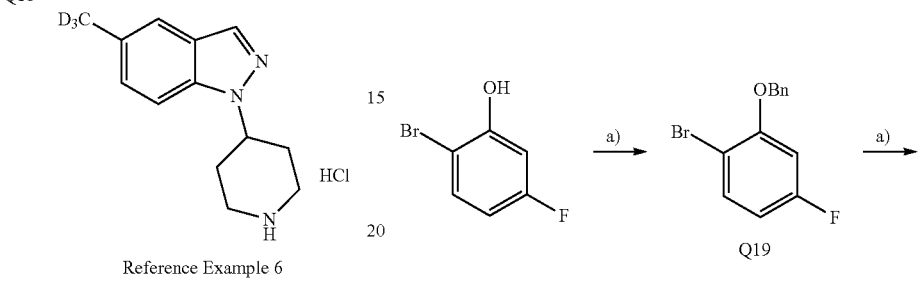

Reference Example 6 a) Preparation of tert-butyl 4-(5-bromo-1H-indazol-1-yl)piperidine-1-carboxylate (Compound Q17)

To a suspension of potassium tert-butoxide (37.25 g) in tetrahydrofuran (1000 mL) was added 5-bromoindazole (54.52 g), and the mixture was stirred at room temperature for 15 minutes. To the reaction solution was added tert-butyl 4-(methylsulfonyloxy)piperidine-1-carboxylate (98.74 g), and the reaction solution was heated at reflux for 1 day. Then, the mixture was partitioned between ethyl acetate and water, and the organic layer was washed with brine and dried over $Na_2SO_4$. The residue was purified by silica gel column chromatography (ethyl acetate:hexane=1:3 as the eluting solvent) to give Compound Q17 (45.68 g).
$^2$H-NMR (400 MHz, $CDCl_3$): 1.49 (9H, s), 2.00 (2H, m), 2.21 (2H, m), 2.96 (2H, m), 4.31 (2H, m), 4.52 (1H, m), 7.34 (1H, d, J=8.8 Hz), 7.45 (1H, d, J=1.7 Hz, 8.8 Hz), 7.88 (1H, d, J=1.7 Hz), 7.94 (1H, s).

b) Preparation of tert-butyl 4-[5-($^2H_3$)methyl-1H-indazol-1-yl]piperidine-1-carboxylate (Compound Q18)

To a solution of Compound Q17 (5.70 g) in anhydrous tetrahydrofuran (60 mL) was added dropwise at −78° C. n-butyllithium (2.6 mol/L in n-hexane, 7.61 mL). The reaction solution was stirred at −78° C. for 3 hours, and deuterated methyl iodide (4.35 g) was added thereto at −78° C. The mixture was stirred at room temperature for 16 hours, and saturated aqueous $NH_4Cl$ solution was added thereto at ice temperature. The mixture was partioned between ethyl acetate and water, and the organic layer was washed with brine and dried over $Na_2SO_4$. The residue was purified by silica gel column chromatography (ethyl acetate:hexane=5:2 as the eluting solvent) to give Compound Q18 (3.64 g).
$^1$H-NMR (400 MHz, $CDCl_3$): 1.49 (9H, s), 2.02 (2H, t, J=10.5 Hz), 2.22 (2H, m), 2.96 (2H, m), 4.31 (2H, s), 4.54 (1H, m), 7.21 (1H, m), 7.34 (1H, d, J=8.5 Hz), 7.50 (1H, m), 7.90 (1H, s).

c) Preparation of 5-($^2H_3$)methyl-1-(piperidin-4-yl)-1H-indazole hydrochloride (Reference Example 6)

To a solution of Compound Q18 (225 mg) in dioxane (3 mL) was added at room temperature 4 mol/L HCl-dioxane (3.3 mL), and the mixture was stirred at 55° C. for 2 hours. Then, the solvent was evaporated under reduced pressure to give Reference Example 6 (225 mg).

REFERENCE EXAMPLE 7

Preparation of 4-(4-ethoxy-5-methyl-1H-indazol-1-yl)piperidine hydrochloride

-continued

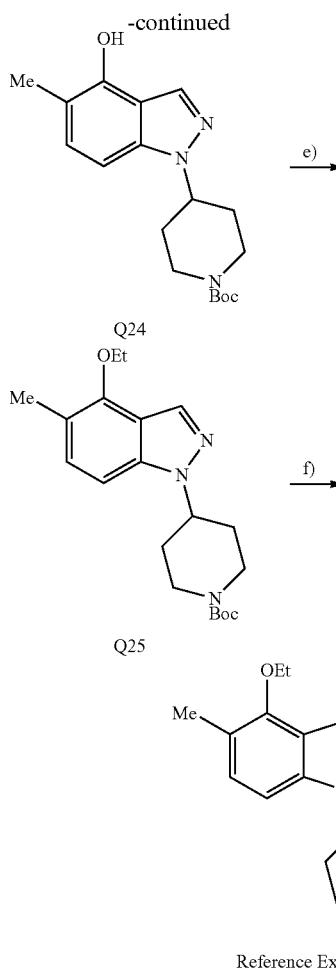

b) Preparation of 4-(benzyloxy)-5-bromo-1H-indazole (Compound Q21)

To a solution of Compound Q20 (3.0 g) in 1,2-dimethoxyethane (15 mL) were added potassium carbonate (1.47 g) and O-methylhydroxyamine hydrochloride (810 mg), and the mixture was stirred at room temperature for 5 hours. The insoluble matter was removed by filtration and the solvent was evaporated under reduced pressure. To the residue were added 1,2-dimethoxyethane (15 mL) and hydrazine hydrate (15 mL), and the mixture was heated at reflux for 21 hours. The reaction solution was cooled to room temperature, the 1,2-dimethoxyethane layer was washed with brine, the mixture was dried over anhydrous MgSO$_4$, and the solvent was evaporated under reduced pressure. The residue was purified by silica gel column chromatography (hexane:ethyl acetate=100:0-40:60 as the eluting solvent) to give Compound Q21 (1.37 g).

$^1$H-NMR (300 MHz, CDCl$_3$) δ: 5.40 (2H, s), 7.06-7.16 (1H, m), 7.30-7.62 (6H, m), 8.06 (1H, s), 10.58 (1H, br s).

c) Preparation of tert-butyl 4-[4-(benzyloxy)-5-bromo-1H-indazol-1-yl]piperidine-1-carboxylate (Compound Q22)

To a suspension of sodium hydride (271 mg) in anhydrous dimethylformamide (20 mL) was added Compound Q21 (1.37 g), and the mixture was stirred at room temperature for 5 minutes. To the reaction solution was added tert-butyl 4-(methylsulfonyloxy)piperidine-1-carboxylate (1.89 g), and the mixture was stirred at 80° C. for 2 hours. The reaction solution was cooled to room temperature, water (100 mL) was added thereto, and the mixture was extracted with ethyl acetate. The organic layer was dried over anhydrous MgSO$_4$ and the solvent was evaporated under reduced pressure. The residue was purified by silica gel column chromatography (hexane:ethyl acetate=100:0-50:50 as the eluting solvent) to give Compound Q22 (1.26 g).

$^1$H-NMR (300 MHz, CDCl$_3$) δ: 1.49 (9H, s), 1.92-2.08 (2H, m), 2.09-2.29 (2H, m), 2.84-3.06 (2H, m), 4.19-4.39 (2H, m), 4.41-4.58 (1H, m), 5.39 (2H, s), 7.00-7.08 (1H, m), 7.28-7.60 (6H, m), 7.99 (1H, s).

d) Preparation of tert-butyl 4-[4-(benzyloxy)-5-methyl-1H-indazol-1-yl]piperidine-1-carboxylate (Compound Q23)

To a solution of Compound Q22 (1.2 g) and bis(tri-tert-butylphosphine)palladium (63 mg) in anhydrous tetrahydrofuran (12 mL) was added dropwise under nitrogen atmosphere chloromethylzinc (0.5 mol/L in tetrahydrofuran, 1.24 mL), and the mixture was stirred at room temperature for 24 hours. To the reaction solution was added water (50 mL), and the insoluble matter was removed by filtration. The filtrate was extracted with ethyl acetate, the organic layer was dried over anhydrous MgSO$_4$, and the solvent was evaporated under reduced pressure. The residue was purified by silica gel column chromatography (hexane ethyl acetate=100:0-50:50 as the eluting solvent) to give Compound Q23 (981 mg).

$^1$H-NMR (300 MHz, CDCl$_3$) δ: 1.92-2.09 (2H, m), 2.11-2.41 (2H, m), 2.32 (3H, s), 2.83-3.10 (2H, m), 4.19-4.61 (3H, m), 5.33 (2H, s), 7.01-7.09 (1H, m), 7.14-7.23 (1H, m), 7.32-7.55 (5H, m), 8.02 (1H, s).

e) Preparation of tert-butyl 4-(4-ethoxy-5-methyl-1H-indazol-1-yl)piperidine-1-carboxylate (Compound Q25)

To a solution of Compound Q23 (981 mg) in ethanol/ethyl acetate (3/1, 20 mL) was added palladium hydroxide on car- Reference Example 7 a) Preparation of 2-(benzyloxy)-3-bromo-6-fluorobenzaldehyde (Compound Q20)

To a solution of 2-bromo-5-fluorophenol (10 g) in acetone (100 mL) were added potassium carbonate (8.68 g) and benzyl bromide (7.51 mL), and the mixture was heated at reflux for 18 hours. The reaction solution was cooled to room temperature and the insoluble matter was removed by filtration to give Compound Q19 as a crude product.

A solution of diisopropylamine (2.88 mL) in anhydrous tetrahydrofuran (40 mL) was cooled to −78° C. To the mixture was added dropwise n-butyllithium (2.6 mol/L in n-hexane, 6.19 mL), and the mixture was stirred at −78° C. for 10 minutes. To the mixture was added dropwise a solution of Compound Q19 (4.10 g) in anhydrous tetrahydrofuran (10 mL) over 15 minutes. The reaction solution was stirred at −78° C. for 1 hour, dimethylformamide (1.25 mL) was added thereto, and the mixture was stirred at the same temperature for 5 minutes. The reaction solution was warmed to room temperature, saturated aqueous NH$_4$Cl solution (100 mL) was added to the solution, and the mixture was extracted with ethyl acetate. The organic layer was dried over anhydrous MgSO$_4$, and the solvent was evaporated under reduced pressure. The residue was recrystallized from a mixed solution of ethyl acetate/hexane to give Compound Q20 (3.08 g).

$^1$H-NMR (400 MHz, CDCl$_3$) δ: 5.03 (2H, s), 6.78-6.90 (1H, m), 7.22-7.51 (5H, m), 7.64-7.78 (1H, m), 10.14 (1H, s).

bon (100 mg), and the mixture was stirred under hydrogen atmosphere for 16 hours. The reaction solution was filtered through Celite and the filtrate was evaporated under reduced pressure to give Compound Q24 as a crude product. To acetone (10 mL) were added the obtained Compound Q24, potassium carbonate (817 mg) and ethyl iodide (0.284 mL), and the mixture was heated at reflux for 24 hours. The reaction solution was cooled to room temperature, the insoluble matter was removed by filtration, and the filtrate was evaporated under reduced pressure. The residue was purified by silica gel column chromatography (hexane:ethyl acetate=100:0-20:80 as the eluting solvent) to give Compound Q25 (611 mg).

$^1$H-NMR (300 MHz, CDCl$_3$) δ: 1.46 (3H, t, J=7.1 Hz), 1.94-2.07 (2H, m), 2.13-2.27 (2H, m), 2.32 (3H, s), 2.85-3.04 (2H, m), 4.21-4.43 (2H, m), 4.37 (2H, q, J=7.1 Hz), 4.43-4.55 (1H, m), 6.98-7.04 (1H, m), 7.15-7.20 (1H, m), 8.02 (1H, s).

f) Preparation of 4-ethoxy-5-methyl-1-(piperidin-4-yl)-1H-indazole hydrochloride (Reference Example 7)

To a solution of Compound Q25 (611 mg) in ethyl acetate (15 mL) was added 4 mol/L HCl-dioxane (1.8 mL), and the mixture was stirred at room temperature for 3 hours. The solvent was evaporated under reduced pressure, the residue was washed with ethyl acetate, and the precipitated crystal was collected by filtration to give Reference Example 7 (420 mg).

$^1$H-NMR (300 MHz, DMSO-D6) δ: 1.36 (3H, t, J=7.0 Hz), 1.98-2.14 (2H, m), 2.17-2.41 (2H, m), 2.23 (3H, s), 2.99-3.22 (2H, m), 3.32-3.50 (2H, m), 4.34 (2H, q, J=7.0 Hz), 4.81-4.98 (1H, m), 7.16-7.29 (2H, m), 8.17 (1H, s), 8.79-9.03 (1H, m), 9.06-9.29 (1H, m).

EXAMPLE 1

N-(trans-4-methoxycyclohexyl)-4-(5-methyl-1H-indazol-1-yl)piperidine-1-carboxamide

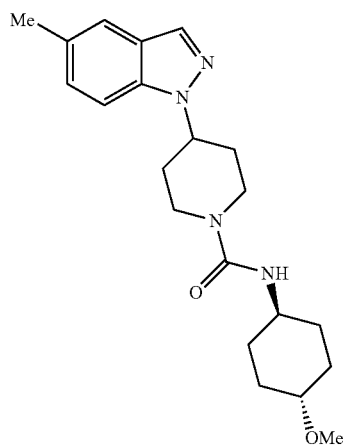

Example 1

To a solution of Reference Example 1 (600 mg) in DMF (5 mL) were added trans-phenyl-4-methoxycyclohexane carbamate (564 mg) and diisopropylethylamine (1.24 mL), and the mixture was stirred with heating at 70° C. for 16 hours. Then, the mixture was partitioned between ethyl acetate and water, the organic layer was dried over Na$_2$SO$_4$, and the solvent was evaporated under reduced pressure. The residue was purified by silica gel column chromatography (ethyl acetate as the eluting solvent) to give Example 1 (564 mg).

$^1$H-NMR (400 MHz, CDCl$_3$): 1.16 (2H, m), 1.36 (2H, m), 2.06 (6H, m), 2.25 (2H, m), 2.46 (3H, s), 2.93-3.21 (3H, m), 3.35 (3H, s), 3.68 (1H, m), 4.10 (2H, m), 4.28 (1H, m), 4.55 (2H, m), 7.21 (1H, d, J=8, 8 Hz), 7.34 (1H, d, J=8, 8 Hz), 7.50 (1H, s), 7.90 (1H, s).

EXAMPLE 2

4-(3-ethoxy-5-ethyl-1H-indazol-1-yl)-N-(tetrahydro-2H-pyran-4-yl)piperidine-1-carboxamide

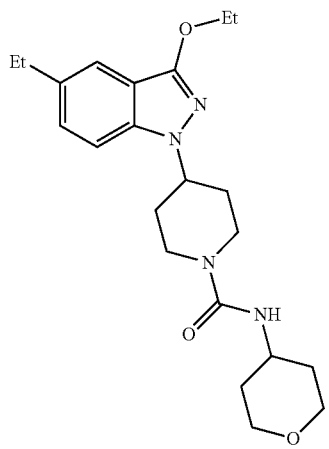

Example 2

To a solution of the above-obtained Reference Example 2 (136 mg) in DMF (3 mL) were added phenyl-4-pyran carbamate (97 mg) and diisopropylethylamine (307 μL), and the mixture was stirred with heating at 70° C. for 16 hours. Then, the mixture was partitioned between ethyl acetate and water, the organic layer was washed with brine and dried over Na$_2$SO$_4$, and the solvent was evaporated under reduced pressure. The residue was purified by silica gel column chromatography (ethyl acetate as the eluting solvent) to give Example 2 (71 mg).

$^1$H-NMR (400 MHz, CDCl$_3$): 1.28 (3H, t, J=7.2 Hz), 1.48 (7H, m), 1.99 (2H, m), 2.21 (2H, m), 2.74 (2H, q, J=7.2 Hz), 3.03 (2H, m), 3.51 (2H, m), 3.98 (3H, m), 4.12 (2H, m), 4.30-4.50 (3H, m), 4.58 (1H, m), 7.23 (2H, m), 7.48 (1H, s).

EXAMPLE 3

(4,4-difluorocyclohexyl)(4-(5-ethoxy-1H-indazol-1-yl)piperidin-1-yl)methanone

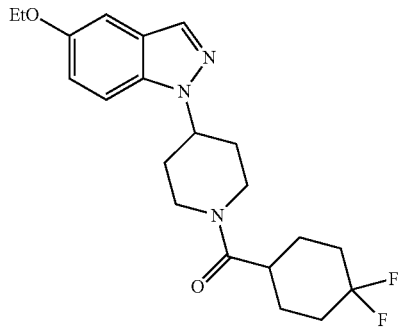

Example 3

To a solution of the above-obtained Reference Example (25 mg), EDCI·HCl (25 mg), HOBt (17 mg) and diisopropylethylamine (62 μL) in DMF (1.0 mL) was added 4,4-difluorocyclohexanecarboxylic acid (14 mg), and the mixture was stirred at room temperature for 1 day. Then, the mixture was partitioned between dichloromethane and water, the organic layer was washed with brine, and the residue was purified by silica gel column chromatography (ethyl acetate:hexane=2:1 as the eluting solvent) to give Example 3 (18 mg).

$^1$H-NMR (400 MHz, CDCl$_3$): 1.38 (3H, t, J=7.0 Hz), 1.87-1.66 (6H, m), 2.16-2.02 (6H, m), 2.56 (1H, s), 2.77 (1H, s), 3.23 (1H, s), 3.99 (3H, q, J=7.0 Hz), 4.53 (1H, m), 4.70 (1H, m), 7.00 (2H, m), 7.26 (1H, m), 7.82 (1H, s).

EXAMPLE 4

N-(cis-4-(5-ethyl-1H-indazol-1-yl)cyclohexyl)-4,4-difluorocyclohexanecarboxamide

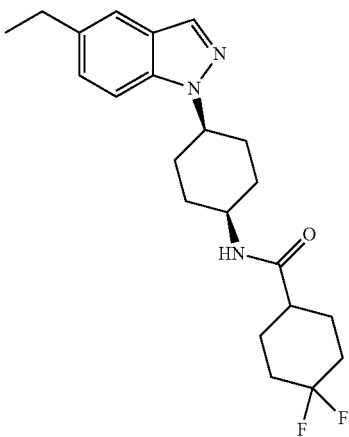

Example 4

To a solution of the above-obtained Reference Example (94 mg), EDCI·HCl (95 mg), HOBt (66 mg), and diisopropylethylamine (236 μL) in DMF (2.0 mL) was added 4,4-difluorocyclohexanecarboxylic acid (55 mg), and the mixture was stirred at room temperature for 1 day. Then, the mixture was partitioned between dichloromethane and water, the organic layer was washed with brine, and the residue was purified by silica gel column chromatography (ethyl acetate:hexane=2:1 as the eluting solvent) to give Example 4 (72 mg).

$^1$H-NMR (400 MHz, CDCl$_3$): 1.30 (3H, t, J=7.6 Hz), 1.65-2.08 (12H, m), 2.10-2.30 (5H, m), 2.78 (2H, q, J=7.6 Hz), 4.25 (1H, m), 4.51 (1H, m), 5.81 (1H, m), 7.26 (1H, d, J=8.8 Hz), 7.54 (1H, d, J=8.4 Hz), 7.55 (1H, s), 7.96 (1H, s).

EXAMPLE 5

1-(4,4-difluorocyclohexyl)-3-(cis-4-(5-ethyl-1H-indazol-1-yl)cyclohexyl)urea

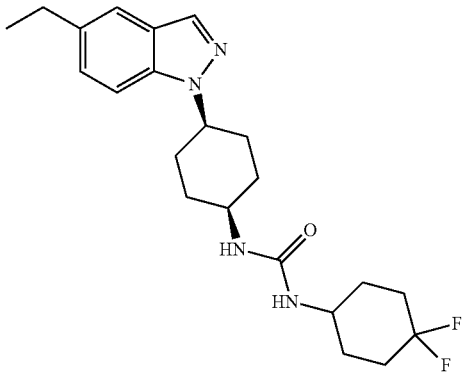

Example 5

To a solution of the above-obtained Reference Example (131 mg) in DMF (3 mL) were added phenyl 4,4-difluorocyclohexane carbamate (119 mg) and diisopropylethylamine (328 μL), and the mixture was stirred with heating at 70° C. for 16 hours. Then, the mixture was partitioned between ethyl acetate and water, the organic layer was washed with brine and dried over Na$_2$SO$_4$, and the solvent was evaporated under reduced pressure. The residue was purified by silica gel column chromatography (ethyl acetate as the eluting solvent) to give Example 5 (24 mg).

$^1$H-NMR (400 MHz, CDCl$_3$): 1.25 (3H, t, J=7.6 Hz), 1.50 (2H, m), 1.70-2.25 (13H, m), 2.75 (2H, q, J=7.6 Hz), 3.65 (1H, m), 4.08 (1H, m), 4.45 (1H, m), 4.55 (1H, m), 5.00 (1H, m), 7.25 (1H, d, J=8.8 Hz), 7.45 (1H, d, J=8.4 Hz), 7.51 (1H, s), 7.93 (1H, s).

EXAMPLE 6 cis-N-(4,4-difluorocyclohexyl)-4-(5-ethyl-1H-indazol-1-yl)cyclohexanecarboxamide

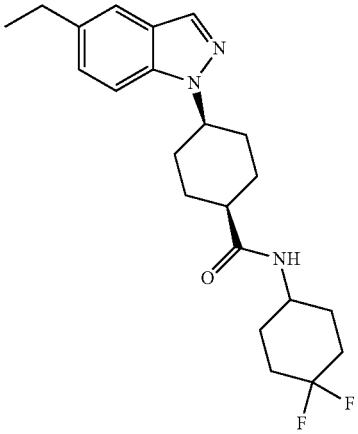

Example 6

To a solution of the above-obtained Reference Example (155 mg), EDCI·HCl (107 mg), HOBt (74 mg), and diisopropylethylamine (399 μL) in DMF (3.0 mL) was added 4,4-difluorocyclohexylamine (77 mg), and the mixture was stirred at room temperature for 1 day. Then, the mixture was partitioned between dichloromethane and water, the organic layer was washed with brine, and the residue was purified by silica gel column chromatography (ethyl acetate:hexane=2:1 as the eluting solvent) to give Example 6 (127 mg).

$^1$H-NMR (400 MHz, CDCl$_3$): 1.26 (3H, t, J=7.2 Hz), 1.50 (2H, m), 1.70-2.22 (12H, m), 2.30-2.48 (3H, m), 2.72 (2H, q, J=7.2 Hz), 3.92 (1H, m), 4.52 (1H, m), 5.45 (1H, m), 7.21 (1H, d, J=8.8 Hz), 7.37 (1H, d, J=8.8 Hz), 7.49 (1H, s), 7.87 (1H, s).

EXAMPLES 7 to 101

The compounds in Table 1 were prepared in the same manner as Examples 1 to 2 except that the corresponding starting compounds were used.

TABLE 1

| Ex. | $R^{1A}$ | $R^{1B}$ | $R^{1C}$ | $R^{1D}$ | $R^{3A}$ | $R^{3B}$ | A | n | (LC-MS: [M + H]$^+$/ Rt (min)) | LC-MS Method |
|---|---|---|---|---|---|---|---|---|---|---|
| 7 | H | H | Me | H | H | c-Pen | CH | 1 | 327.5/ 3.71 | C |
| 8 | H | H | Me | H | H | c-Hex | CH | 1 | 341.4/ 3.87 | C |
| 9 | H | H | Me | H | H | tetrahydropyran-4-yl | CH | 1 | 343.4/ 3.27 | C |
| 10 | H | H | Me | H |   | 4,4-difluorocyclohexyl | CH | 1 | 363.5/ 3.91 | C |
| 11 | H | H | Me | H |   | 4-methoxycyclohexyl | CH | 1 | 357.4/ 3.56 | C |
| 12 | H | H | Me | H | H | 2,2-dimethyltetrahydropyran-4-yl | CH | 1 | 371.5/ 3.40 | C |
| 13 | H | H | Me | H | H | 4,4-difluorocyclohexyl | CH | 1 | 377.6/ 3.79 | C |
| 14 | H | H | iPr | H | H | tetrahydropyran-4-yl | CH | 1 | 371.5/ 4.63 | A |
| 15 | H | H | n-Pr | H | H | tetrahydropyran-4-yl | CH | 1 | 371.4/ 4.63 | A |
| 16 | H | H | Et | H | H | trans-4-methoxycyclohexyl | CH | 1 | 385.6/ 4.66 | A |

TABLE 1-continued
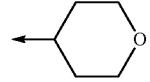
| Ex. | $R^{1A}$ | $R^{1B}$ | $R^{1C}$ | $R^{1D}$ | $R^{3A}$ | $R^{3B}$ | A | n | (LC-MS: [M + H]⁺/ Rt (min)) | LC-MS Method |
|---|---|---|---|---|---|---|---|---|---|---|
| 17 | H | H | OEt | H | H | c-Pen | CH | 1 | 357.3/ 0.901 | D |
| 18 | H | H | OEt | H | H | c-Hex | CH | 1 | 371.4/ 0.955 | D |
| 19 | H | H | OEt | H | H | 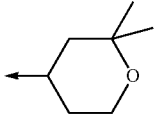 | CH | 1 | 373.3/ 0.738 | D |
| 20 | H | H | Et | H | H | c-Pen | CH | 1 | 341.3/ 0.987 | D |
| 21 | H | H | Et | H | H | 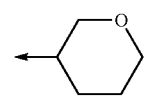 | CH | 1 | 385.4/ 0.899 | D |
| 22 | H | H | Et | H | H |  | CH | 1 | 357.3/ 0.857 | D |
| 23 | H | H | Et | H | H | 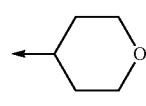 | CH | 1 | 391.3/ 1.004 | D |
| 24 | H | H | Et | H | H |  | CH | 1 | 357.3/ 0.828 | D |
| 25 | H | H | 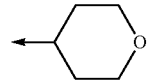 | H | H | 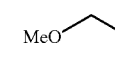 | CH | 1 | 386.2/ 4.24 | A |
| 26 | H | H | 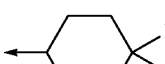 | H | H |  | CH | 1 | 435.6/ 4.54 | A |
| 27 | H | H | EtO | H | H | 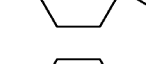 | N | 1 | 407.5/ 4.54 | A |
| 28 | H | H | F | H | H | 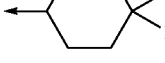 | CH | 1 | 381.3/ 3.64 | C |
| 29 | H | H | F | H | H |  | CH | 1 | 375.3/ 3.26 | C |

TABLE 1-continued
| Ex. | R^1A | R^1B | R^1C | R^1D | R^3A | R^3B | A | n | (LC-MS: [M + H]+/ Rt (min)) | LC-MS Method |
|---|---|---|---|---|---|---|---|---|---|---|
| 30 | H | H | EtO | H | H | 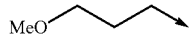 | CH | 1 | 401.4/ 3.38 | C |
| 31 | H | H | MeO~ | H | H | c-Pen | CH | 1 | 385.4/ 3.63 | C |
| 32 | H | H | MeO~ | H | H | 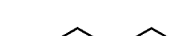 | CH | 1 | 429.4/ 3.38 | C |
| 33 | H | H | Cl | H | H | c-Pen | CH | 1 | 347.3/ 3.79 | C |
| 34 | H | H | Cl | H | H | 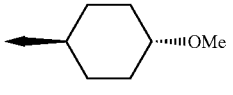 | CH | 1 | 397.2/ 3.87 | C |
| 35 | H | H | Cl | H | H | 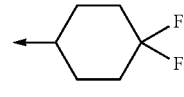 | CH | 1 | 391.1/ 3.52 | C |
| 36 | MeO~ | H | Me | H | H | 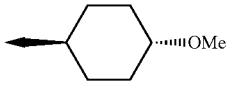 | CH | 1 | 421.5/ 4.60 | A |
| 37 | H | c-Pr | H | H | H | 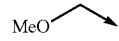 | CH | 1 | 397.0/ 4.63 | A |
| 38 | H | H | H | H | H | 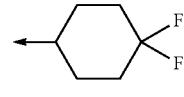 | CH | 1 | 363.2/ 3.67 | A |
| 39 | H | H | H | H | H | c-Hex | CH | 1 | 327.0/ 4.19 | A |
| 40 | H | H | OMe | H | H | c-Hex | CH | 1 | 356.8/ 4.21 | A |
| 41 | H | H | OMe | H | H | 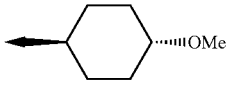 | CH | 1 | 393.0/ 3.68 | A |
| 42 | Et | H | Me | H | H | 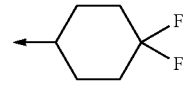 | CH | 1 | 405.4/ 4.86 | A |
| 43 | Et | H | Me | H | H | 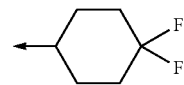 | CH | 1 | 371.0/ 4.57 | A |

TABLE 1-continued

[Structure: indazole with substituents R1A, R1B, R1C, R1D on positions, A in ring, N-piperidine with (CH2)n linker, N-C(=O)-NR3AR3B]

| Ex. | R1A | R1B | R1C | R1D | R3A | R3B | A | n | (LC-MS: [M + H]+/ Rt (min)) | LC-MS Method |
|---|---|---|---|---|---|---|---|---|---|---|
| 44 | H | c-Pr | H | H | H | trans-cyclohexyl-OEt | CH | 1 | 411.1/ 4.71 | A |
| 45 | Me | H | Me | H | H | 4,4-difluorocyclohexyl | CH | 1 | 371.0/ 4.51 | A |
| 46 | H | H | OiPr | H | H | 4,4-difluorocyclohexyl | CH | 1 | 421.0/ 4.63 | A |
| 47 | H | H | OiPr | H | H | trans-cyclohexyl-OMe | CH | 1 | 415.5 4.45 | A |
| 48 | H | H | OiPr | H | H | c-Hex | CH | 1 | 385.0/ 4.68 | A |
| 49 | H | H | OiPr | H | H | c-Pen | CH | 1 | 371.0/ 4.54 | A |
| 50 | H | H | H | H | H | 4,4-difluorocyclohexyl | C-Et | 1 | 391.0/ 4.47 | A |
| 51 | H | H | H | H | Et | trans-cyclohexyl-OMe | CH | 1 | 385.4/ 4.50 | A |
| 52 | tetrahydropyran-4-yl | H | Me | H | H | 4,4-difluorocyclohexyl | CH | 1 | 461.4/ 3.90 | C |
| 53 | Et | H | H | H | H | 4,4-difluorocyclohexyl | CH | 1 | 391.2/ 3.91 | C |
| 54 | H | H | MeOCH2CH2 | H | H | 4,4-difluorocyclohexyl | CH | 1 | 407.2/ 3.45 | C |
| 55 | tetrahydropyran-4-yl | H | Me | H | H | trans-cyclohexyl-OMe | CH | 1 | 455.5/ 3.58 | C |
| 56 | OEt | H | Et | H | H | c-Pen | CH | 1 | 385.2/ 2.47 | B |

TABLE 1-continued
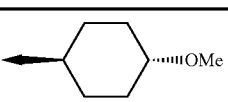
| Ex. | $R^{1A}$ | $R^{1B}$ | $R^{1C}$ | $R^{1D}$ | $R^{3A}$ | $R^{3B}$ | A | n | (LC-MS: [M + H]+/ Rt (min)) | LC-MS Method |
|---|---|---|---|---|---|---|---|---|---|---|
| 57 | OEt | H | Et | H | H | 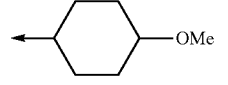 | CH | 1 | 429.2/ 2.29 | B |
| 58 | OiPr | H | Et | H | H | c-Pen | CH | 1 | 399.2/ 1.95 | B |
| 59 | OiPr | H | Et | H | H | 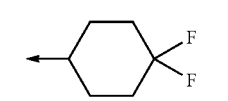 | CH | 1 | 443.2/ 1.81 | B |
| 60 | OEt | H | Et | H | H | c-Hex | CH | 1 | 399.2/ 2.06 | B |
| 61 | OEt | H | Et | H | H | 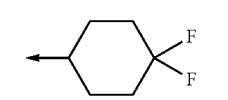 | CH | 1 | 435.2/ 1.99 | B |
| 62 | OiPr | H | Et | H | H | 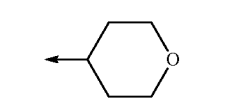 | CH | 1 | 449.2/ 2.29 | B |
| 63 | OiPr | H | Et | H | H |  | CH | 1 | 415.2/ 2.07 | B |
| 64 | H | Et | H | H | H | 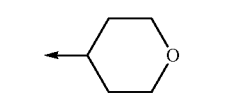 | CH | 1 | 391.0/ 4.65 | A |
| 65 | H | H | Br | H | H |  | CH | 1 | 408.1/ 4.26 | A |
| 66 | H | Et | H | H | H | 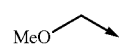 | CH | 1 | 385.5/ 4.30 | A |
| 67 | 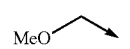 | H | Me | H | H | c-Pen | CH | 1 | 371.2/ 4.57 | A |
| 68 | 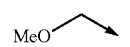 | H | Me | H | H | c-Hex | CH | 1 | 385.5/ 4.74 | A |
| 69 | 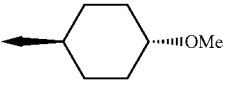 | H | Me | H | H | 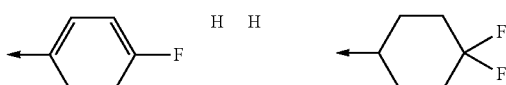 | CH | 1 | 415.5/ 4.40 | A |
| 70 | H | H | 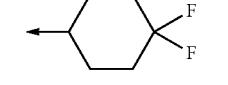 | H | H | 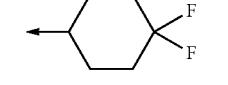 | CH | 1 | 457.8/ 4.96 | A |

TABLE 1-continued

| Ex. | $R^{1A}$ | $R^{1B}$ | $R^{1C}$ | $R^{1D}$ | $R^{3A}$ | $R^{3B}$ | A | n | (LC-MS: $[M+H]^+$/ Rt (min)) | LC-MS Method |
|---|---|---|---|---|---|---|---|---|---|---|
| 71 | H | H | Br | H | H | cyclohexyl-OMe (trans) | CH | 1 | 436.4/ 4.45 | A |
| 72 | H | H | Et | H | H | tetrahydropyran | CH | 1 | 343.5/ 4.25 | A |
| 73 | H | H | Et | H | H | 4,4-difluorocyclohexyl | CH | 2 | 405.4/ 4.89 | A |
| 74 | H | H | c-Pr | H | H | cyclohexyl-OMe (trans) | CH | 1 | 397.0/ 4.63 | A |
| 75 | H | H | c-Pr | H | H | tetrahydropyran | CH | 1 | 368.9/ 4.46 | A |
| 76 | H | H | n-Pr | H | H | cyclohexyl-OMe (trans) | CH | 1 | 399.4/ 4.85 | A |
| 77 | H | H | c-Pr | H | H | 4,4-difluorocyclohexyl | CH | 1 | 403.2/ 4.78 | A |
| 78 | H | H | Me | H | H | 2,2-difluorocyclohexyl (R) | CH | 1 | 377.5/ 4.53 | A |
| 79 | H | H | Me | H | H | 2,2-difluorocyclohexyl (S) | CH | 1 | 377.2/ 4.51 | A |
| 80 | H | H | Me | H | H | 2,2-difluorocyclopentyl (S) | CH | 1 | 363.6/ 4.44 | A |

TABLE 1-continued
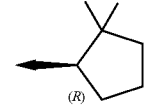
| Ex. | $R^{1A}$ | $R^{1B}$ | $R^{1C}$ | $R^{1D}$ | $R^{3A}$ | $R^{3B}$ | A | n | (LC-MS: $[M+H]^+$/ Rt (min)) | LC-MS Method |
|---|---|---|---|---|---|---|---|---|---|---|
| 81 | H | H | Me | H | H | 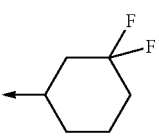 | CH | 1 | 363.3/ 4.44 | A |
| 82 | H | H | Me | H | H | 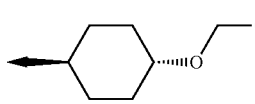 | CH | 1 | 377.4/ 4.57 | A |
| 83 | H | H | Me | H | H | 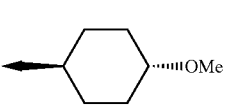 | CH | 1 | 439.1/ 4.68 | A |
| 84 | H | H | Et | H | H | 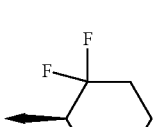 | CH | 2 | 399.0/ 4.71 | A |
| 85 | H | H | MeO | H | H | 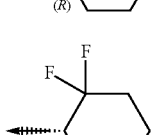 | CH | 1 | 392.8/ 4.28 | A |
| 86 | H | H | MeO | H | H | 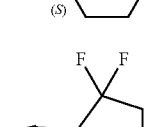 | CH | 1 | 392.8/ 4.30 | A |
| 87 | H | H | MeO | H | H | 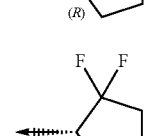 | CH | 1 | 379.0/ 4.16 | A |
| 88 | H | H | MeO | H | H | 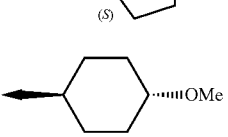 | CH | 1 | 379.0/ 4.15 | A |
| 89 | Me | H | Me | H | H |  | CH | 1 | 385.4/ 4.59 | A |

TABLE 1-continued

| Ex. | $R^{1A}$ | $R^{1B}$ | $R^{1C}$ | $R^{1D}$ | $R^{3A}$ | $R^{3B}$ | A | n | (LC-MS: [M + H]$^+$/ Rt (min)) | LC-MS Method |
|---|---|---|---|---|---|---|---|---|---|---|
| 90 | H | H | Me | H | H | cyclohexyl-OEt | CH | 1 | 385.0/ 4.57 | A |
| 91 | H | H | Me | H | H | cyclohexyl-OMe | CH | 1 | 371.0/ 4.46 | A |
| 92 | H | H | Et | H | H | cyclohexyl-OMe | CH | 1 | 385.4/ 4.67 | A |
| 93 | H | Me | H | H | H | cyclohexyl-F,F | CH | 1 | 377.3/ 4.54 | A |
| 94 | H | Me | H | H | H | cyclohexyl-OMe | CH | 1 | 371.0/ 4.38 | A |
| 95 | H | Me | H | H | H | cyclohexyl-OMe | CH | 1 | 371.0/ 4.41 | A |
| 96 | H | Me | H | H | H | cyclohexyl-OEt | CH | 1 | 385.4/ 4.51 | A |
| 97 | H | Me | H | H | H | cyclohexyl-OCHF$_2$ | CH | 1 | 407.2/ 4.54 | A |
| 98 | H | Br | H | H | H | cyclohexyl-OMe | CH | 1 | 435.1/ 4.63 | A |
| 99 | H | H | Et | H | H | cyclohexyl-F,F | N | 1 | 392.0/ 4.49 | A |
| 100 | H | H | Et | H | H | cyclohexyl-OMe | N | 1 | 386.2/ 4.31 | A |

TABLE 1-continued

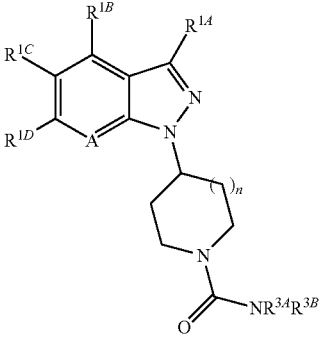

| Ex. | R¹ᴬ | R¹ᴮ | R¹ᶜ | R¹ᴰ | R³ᴬ | R³ᴮ | A | n | (LC-MS: [M + H]⁺/ Rt (min)) | LC-MS Method |
|---|---|---|---|---|---|---|---|---|---|---|
| 101 | H | H | Et | H | H | tetrahydropyran-4-yl | N | 1 | 358.0/ 4.09 | A |

EXAMPLES 102 to 118

The compounds in Table 2 were prepared in the same manner as Example 3 except that the corresponding starting compounds were used.

TABLE 2

[Structure: 5-R¹ᶜ-indazole-1-yl piperidine with N-C(O)-R⁴]

| Ex. | R¹ᶜ | R⁴ | (LC-MS: [M + H]⁺/ Rt (min)) | LC-MS Method |
|---|---|---|---|---|
| 102 | Br | tetrahydropyran-4-yl | 394.0/4.01 | A |
| 103 | iBu | tetrahydropyran-4-yl | 370.3/4.70 | A |
| 104 | F | tetrahydropyran-4-yl | 332.4/3.89 | A |
| 105 | Me | c-Hex | 326.5/4.08 | C |
| 106 | Me | c-Pen | 312.3/3.93 | C |
| 107 | iPr | tetrahydropyran-4-yl | 356.2/4.66 | A |

TABLE 2-continued

| Ex. | R¹ᶜ | R⁴ | (LC-MS: [M + H]⁺/ Rt (min)) | LC-MS Method |
|---|---|---|---|---|
| 108 | n-Pr | tetrahydropyran-4-yl | 356.3/4.65 | A |
| 109 | OEt | c-Hex | 356.3/1.01 | C |
| 110 | OEt | c-Pen | 342.3/0.959 | C |
| 111 | Et | tetrahydropyran-4-yl | 342.3/0.868 | C |
| 112 | OEt | 4-fluorophenyl | 368.1/3.79 | C |
| 113 | Et | 4,4-difluorocyclohexyl | 376.4/4.57 | A |
| 114 | OEt | 5-fluoropyridin-2-yl | 369.2/4.28 | A |

TABLE 2-continued
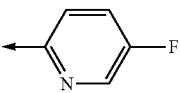
| Ex. | R1C | R4 | (LC-MS: [M + H]+/ Rt (min)) | LC-MS Method |
|---|---|---|---|---|
| 115 | OiPr | 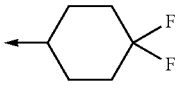 | 383.0/4.39 | A |
| 116 | OiPr |  | 406.3/4.55 | A |
| 117 | Et | 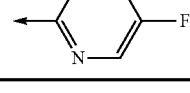 | 370.2/3.86 | C |
| 118 | Et | 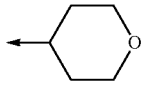 | 353.3/3.74 | C |
EXAMPLES 119 to 126
The compounds in Table 3 were prepared in the same manner as Examples 4 and 5 except that the corresponding starting compounds were used.
TABLE 3
| Ex. | R1A | R1C | R4 | (LC-MS: [M + H]+/ Rt (min)) | LC-MS Method |
|---|---|---|---|---|---|
| 119 | H | Et | c-Hex | 354.1/2.18 | B |
| 120 | H | Et | 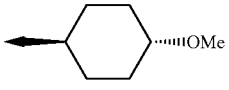 | 356.1/1.88 | B |
| 121 | H | Et |  | 328.1/2.11 | B |
| 122 | H | Et | 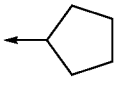 | 384.1/2.00 | B |
| 123 | H | Et |  | 340.1/2.11 | B |

TABLE 3-continued

| Ex. | R$^{1A}$ | R$^{1C}$ | R$^4$ | (LC-MS: [M + H]$^+$/ Rt (min)) | LC-MS Method |
|---|---|---|---|---|---|
| 124 | H | Et | (trans-4-OMe-cyclohexyl) | 384.1/2.04 | B |
| 125 | MeO-CH$_2$- | Me | (trans-4-OMe-cyclohexyl) | 414.4/4.86 | A |
| 126 | MeO-CH$_2$- | Me | (4,4-difluorocyclohexyl) | 420.1/4.92 | A |

EXAMPLES 127 to 131

The compounds in Table 4 were prepared in the same manner as Example 6 except that the corresponding starting compounds were used.

TABLE 4

| Ex. | R$^{1C}$ | R$^{3A}$ | R$^{3B}$ | (LC-MS: [M + H]$^+$/ Rt (min)) | LC-MS Method |
|---|---|---|---|---|---|
| 127 | Et | H | c-Hex | 354.2/2.32 | B |
| 128 | Et | H | c-Pen | 340.1/2.10 | B |
| 129 | Et | H | tetrahydropyran-4-yl | 356.2/2.04 | B |
| 130 | Et | H | 4-methoxycyclohexyl | 384.2/1.85 | B |
| 131 | Et | H | tert-butyl | 327.2/2.31 | B |

EXAMPLES 132 to 141

The compounds in Table 5 were prepared in the same manner as Example 3 except that the corresponding starting compounds were used.

TABLE 5

| Ex. | R¹ᴬ | R¹ᴮ | R¹ᶜ | R⁴ | (LC-MS: [M + H]⁺/ Rt (min)) | LC-MS Method |
|---|---|---|---|---|---|---|
| 132 | H | H | OEt | 5-CF₃-pyridin-2-yl | 418.8/4.63 | A |
| 133 | H | H | Me | 4,4-difluorocyclohexyl | 362.1/4.48 | A |
| 134 | H | H | F | 4,4-difluorocyclohexyl | 366.0/4.32 | A |
| 135 | MeOCH₂CH₂- | H | Me | 4,4-difluorocyclohexyl | 406.7/4.48 | A |
| 136 | MeOCH₂CH₂- | H | Et | 4,4-difluorocyclohexyl | 420.0/4.69 | A |
| 137 | H | H | H | 4,4-difluorocyclohexyl | 348.1/4.27 | A |
| 138 | H | H | Me | 4,4-difluorocyclohexyl | 362.0/4.56 | A |
| 139 | H | Et | H | 4,4-difluorocyclohexyl | 376.1/4.66 | A |
| 140 | H | H | c-Pr | tetrahydropyran-4-yl | 354.4/4.42 | A |
| 141 | H | H | c-Pr | trans-4-methoxycyclohexyl | 382.5/4.63 | A |

EXAMPLES 142 and 143

The compounds in Table 6 were prepared in the same manner as Examples 1 and 2 except that the corresponding starting compounds were used.

TABLE 6

| Ex. | R$^{1C}$ | R$^4$ | (LC-MS: [M + H]$^+$/ Rt (min)) | LC-MS Method |
|---|---|---|---|---|
| 142 | Et | (tetrahydropyran-4-yl) | 383.1/1.93 | B |
| 143 | Et | (4,4-difluorocyclohexyl) | 417.2/1.83 | B |

EXAMPLE 144

N-(trans-4-methoxycyclohexyl)-4-[5-($^2$H$_3$)methyl-1H-indazol-1-yl]piperidine-1-carboxamide

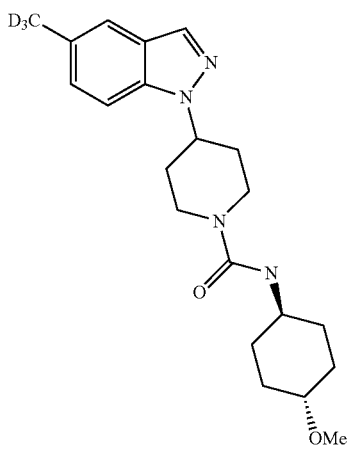

Example 144

To a solution of Reference Example 6 (225 mg) in acetonitrile (5 mL) were added trans-phenyl-4-methoxycyclohexane carbamate (176 mg) and diisopropylethylamine (0.62 mL), and the mixture was stirred with heating at 80° C. for 16 hours. Then, the mixture was partitioned between ethyl acetate and water, the organic layer was dried over Na$_2$SO$_4$, and the solvent was evaporated under reduced pressure. The residue was purified by silica gel column chromatography (ethyl acetate as the eluting solvent) to give Example 144 (127 mg).

$^1$H-NMR (400 MHz, CDCl$_3$): 1.16 (2H, m), 1.36 (2H, m), 2.07 (6H, m), 2.25 (2H, m), 2.46 (3H, s), 2.97-3.07 (2H, m), 3.13 (1H, m), 3.35 (3H, s), 3.68 (1H, m), 4.11 (2H, m), 4.31 (1H, m), 4.55 (2H, m), 7.21 (1H, dd, J=1.7 Hz, 8.6 Hz), 7.34 (1H, d, J=8, 8 Hz), 7.50 (1H, m), 7.90 (1H, s). LC-MS: [M+H]$^+$/Rt (min)=374.4/4.63 (Method A)

EXAMPLE 145

4-(4-ethoxy-5-methyl-1H-indazol-1-yl)-N-(trans-4-methoxycyclohexyl)piperidine-1-carboxamide

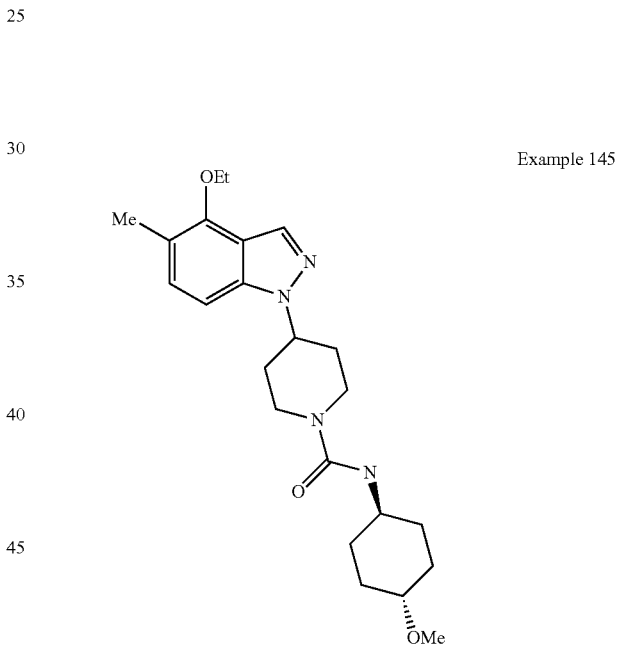

Example 145

To a solution of Reference Example 7 (89 mg) and diisopropylethylamine (0.156 mL) in acetonitrile (4 mL) was added trans-phenyl-4-methoxycyclohexane carbamate (75 mg), and the mixture was stirred at 80° C. for 17 hours. The solvent was evaporated under reduced pressure, and the residue was purified by silica gel column chromatography (hexane:ethyl acetate=40:60-1:100 as the eluting solvent) and then recrystallized (ethyl acetate:hexane) to give Example 145 (61 mg).

$^1$H-NMR (300 MHz, CDCl$_3$) δ: 1.04-1.56 (4H, m), 1.46 (3H, t, J=7.0 Hz), 1.94-2.41 (8H, m), 2.32 (3H, s), 2.92-3.21 (3H, m), 3.35 (3H, s), 3.59-3.77 (1H, m), 4.02-4.18 (2H, m), 4.29 (1H, d, J=7.2 Hz), 4.37 (2H, q, J=7.0 Hz), 4.43-4.60 (1H, m), 6.96-7.04 (1H, m), 7.13-7.21 (1H, m), 8.01 (1H, s).

EXAMPLES 146 to 303

The compounds in Table 7 were prepared in the same manner as Examples 1, 2, 144 and 145 except that the corresponding starting compounds were used.

TABLE 7

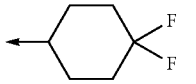

| Ex. | $R^{1A}$ | $R^{1B}$ | $R^{1C}$ | $R^{1D}$ | $R^{3A}$ | $R^{3B}$ | (LC-MS: [M + H]$^+$/ Rt (min)) | LC-MS Method |
|---|---|---|---|---|---|---|---|---|
| 146 | OMe | H | Me | H | H | 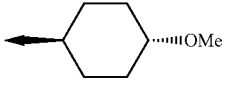 | 357.2/1.61 | B |
| 147 | OMe | H | Me | H | H |  | 401.2/1.47 | B |
| 148 | OMe | H | Me | H | H | 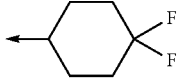 | 373.2/1.15 | B |
| 149 | OMe | H | Et | H | H |  | 421.0/2.41 | B |
| 150 | OMe | H | Et | H | H | 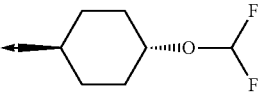 | 387.1/2.14 | B |
| 151 | OMe | H | Et | H | H | c-Hex | 385.1/1.83 | B |
| 152 | OMe | H | Et | OMe | H | c-Pen | 371.1/1.70 | B |
| 153 | OiPr | H | Et | H | H | c-Hex | 413.1/2.37 | B |
| 154 | H | H | Me | H | H | 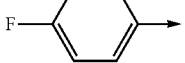 | 407/1.030 | F |
| 155 | H | H | 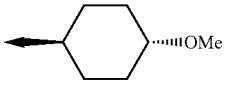 | H | H | 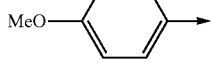 | 451/1.084 | F |
| 156 | H | H | 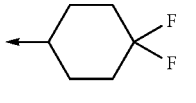 | H | H | 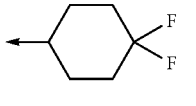 | 469/1.170 | F |
| 157 | 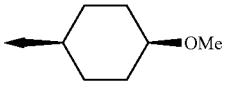 | H | Et | H | H |  | 435/1.116 | F |
| 158 | H | Et | H | H | H |  | 385.4/4.65 | A |

TABLE 7-continued

| Ex. | R¹ᴬ | R¹ᴮ | R¹ᶜ | R¹ᴰ | R³ᴬ | R³ᴮ | (LC-MS: [M + H]⁺/ Rt (min)) | LC-MS Method |
|---|---|---|---|---|---|---|---|---|
| 159 | H | Et | H | H | H | cyclohexyl-OCHF₂ | 421.1/4.70 | A |
| 160 | H | c-Pr | H | H | H | cyclohexyl-OMe | 397.0/4.68 | A |
| 161 | H | c-Pr | H | H | H | 4,4-difluorocyclohexyl | 403.4/4.84 | A |
| 162 | H | H | Me | H | H | cyclohexyl-OCH₂-cyclopropyl | 411/1.057 | F |
| 163 | H | H | CF₃ | H | H | cyclohexyl-OMe | 424.5/4.59 | A |
| 164 | H | H | CF₃ | H | H | 4,4-difluorocyclohexyl | 431.4/471 | A |
| 165 | H | MeOCH₂- | H | H | H | c-Hex | 371.1/1.99 | B |
| 166 | H | MeOCH₂- | H | H | H | 4,4-difluorocyclohexyl | 407.1/1.93 | B |
| 167 | H | EtOCH₂- | H | H | H | c-Hex | 385.2/2.10 | B |
| 168 | H | EtOCH₂- | Et | H | H | 4,4-difluorocyclohexyl | 421.1/2.04 | B |
| 169 | H | CF₃ | H | H | H | 4,4-difluorocyclohexyl | 431.1/1.84 | B |
| 170 | H | H | Me | H | H | 1-methyl-4-methoxycyclohexyl | 385/1.045 | F |
| 171 | H | H | c-Pr | H | H | c-Pen | 353/1.101 | F |
| 172 | H | H | c-Pr | H | H | t-Bu | 341/1.123 | F |

TABLE 7-continued

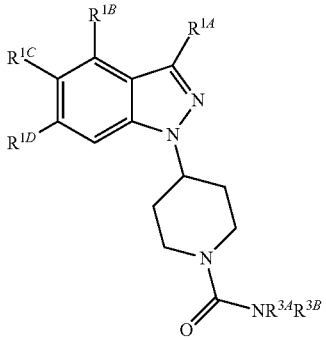

| Ex. | R<sup>1A</sup> | R<sup>1B</sup> | R<sup>1C</sup> | R<sup>1D</sup> | R<sup>3A</sup> | R<sup>3B</sup> | (LC-MS: [M + H]<sup>+</sup>/ Rt (min)) | LC-MS Method |
|---|---|---|---|---|---|---|---|---|
| 173 | H | H | c-Pr | H | | cyclohexyl | 353/1.215 | D |
| 174 | H | H | c-Pr | H | | tetrahydropyranyl | 355/0.962 | F |
| 175 | H | H | c-Pr | H | H | cyclohexylmethyl | 381/1.183 | F |
| 176 | H | H | c-Pr | H | H | c-Pr | 325/0.929 | F |
| 177 | H | H | c-Pr | H | H | tetrahydropyran-3-yl | 369/0.940 | F |
| 178 | H | H | CF<sub>3</sub> | H | H | trans-4-OCD<sub>3</sub>-cyclohexyl | 428/1.93 | E |
| 179 | H | H | c-Pr | H | H | 4-Me-4-OMe-cyclohexyl | 411/1.131 | F |
| 180 | H | OiPr | H | H | H | c-Hex | 385.2/2.46 | B |
| 181 | H | OMe | H | H | H | c-Hex | 357.1/2.21 | B |
| 182 | H | OMe | H | H | H | 4,4-difluorocyclohexyl | 393.1/2.15 | B |
| 183 | H | OiPr | H | H | H | 4,4-difluorocyclohexyl | 421.1/2.39 | B |
| 184 | H | OEt | H | H | H | trans-4-OMe-cyclohexyl | 401.2/1.95 | B |
| 185 | H | H | c-Pr | H | H | c-Bu | 339/1.107 | F |
| 186 | H | H | c-Pr | H | H | trans-4-(2-methoxyethoxy)-cyclohexyl | 411/1.014 | F |

TABLE 7-continued

| Ex. | R$^{1A}$ | R$^{1B}$ | R$^{1C}$ | R$^{1D}$ | R$^{3A}$ | R$^{3B}$ | (LC-MS: [M + H]$^+$/ Rt (min)) | LC-MS Method |
|---|---|---|---|---|---|---|---|---|
| 187 | H | H | c-Pr | H | H | 5-CF$_3$-pyridin-2-yl | 430/1.127 | F |
| 188 | H | H | c-Pr | H |  | 4,4-difluorocyclohexyl (CH$_2$) | 389/1.175 | D |
| 189 | H | H | c-Pr | H | H | trans-4-OMe-cyclohexyl | 397.4/4.61 | A |
| 190 | H | F | H | H | H | 4,4-difluorocyclohexyl | 381.1/1.58 | B |
| 191 | H | OEt | H | H | H | c-Hex | 371.1/2.35 | B |
| 192 | H | OEt | H | H | H | 4,4-difluorocyclohexyl | 407.2/2.28 | B |
| 193 | H | H | c-Pr | H | H | 4-OMe-benzyl | 405/1.091 | F |
| 194 | H | H | c-Pr | H | H | benzyl | 375/1.105 | F |
| 195 | H | H | c-Pr | H | H | 4-CF$_3$-benzyl | 443/1.221 | F |
| 196 | H | H | pyridin-3-yl | H | H | 4,4-difluorocyclohexyl | 440/0.714 | F |
| 197 | H | H | H | c-Pr | H | cis-4-OMe-cyclohexyl | 397.3/4.55 | A |
| 198 | H | H | CN | H | H | 4,4-difluorocyclohexyl | 388.3/4.16 | A |
| 199 | H | H | c-Pr | H | H | c-Hex | 367/1.219 | F |

TABLE 7-continued

| Ex. | R$^{1A}$ | R$^{1B}$ | R$^{1C}$ | R$^{1D}$ | R$^{3A}$ | R$^{3B}$ | (LC-MS: [M + H]$^+$/ Rt (min)) | LC-MS Method |
|---|---|---|---|---|---|---|---|---|
| 200 | H | H | c-Pr | H | H | 1-methylcyclopropyl | 339/0.981 | F |
| 201 | H | OCHF$_2$ | H | H | H | 4,4-difluorocyclohexyl | 429.2/2.06 | B |
| 202 | H | OCHF$_2$ | H | H | H | trans-4-methoxycyclohexyl | 423.2/1.93 | B |
| 203 | H | H | c-Pr | H | H | 1-acetylpiperidin-4-yl | 410/0.857 | F |
| 204 | H | H | c-Pr | H | H | 6-chloropyridazin-3-yl | 397/1.022 | F |
| 205 | H | H | c-Pr | H | H | trans-4-(difluoromethoxy)cyclohexyl | 433/1.127 | F |
| 206 | H | H | c-Pr | H | H | 1-(4-methoxyphenyl)cyclopropyl | 431/1.102 | F |
| 207 | H | H | EtOCH$_2$ | H | H | 4,4-difluorocyclohexyl | 421.3/4.34 | A |
| 208 | OiPr | H | Me | H | H | tetrahydropyran-4-yl | 401/1.742 | E |
| 209 | OCHF$_2$ | H | Et | H | H | tetrahydropyran-4-yl | 423/1.694 | E |
| 210 | H | H | c-Pr | H | H | 2,2-dimethyltetrahydropyran-4-yl | 397/0.970 | F |

TABLE 7-continued

| Ex. | R¹ᴬ | R¹ᴮ | R¹ᶜ | R¹ᴰ | R³ᴬ | R³ᴮ | (LC-MS: [M + H]⁺/ Rt (min)) | LC-MS Method |
|---|---|---|---|---|---|---|---|---|
| 211 | H | H | c-Pr | H | H | trans-4-methoxycyclohexyl | 397/1.019 | F |
| 212 | H | H | Me | H | H | trans-4-methoxycyclohexyl | 371/0.950 | F |
| 213 | H | MeOCH₂– | Me | H | H | 4,4-difluorocyclohexyl | 421/0.962 | F |
| 214 | H | MeOCH₂– | Me | H | H | trans-4-methoxycyclohexyl | 415/0.871 | F |
| 215 | H | MeOCH₂– | c-Pr | H | H | 4,4-difluorocyclohexyl | 447/1.046 | F |
| 216 | H | MeOCH₂– | c-Pr | H | H | trans-4-methoxycyclohexyl | 441/0.957 | F |
| 217 | H | H | c-Pr | H | H | 3,3-difluorocyclobutyl | 375/1.015 | F |
| 218 | H | H | Me | H | H | 3,3-difluorocyclobutyl | 349/0.949 | F |
| 219 | H | H | OCF₃ | H | H | trans-4-methoxycyclohexyl | 441/1.62 | E |
| 220 | H | H | Me | H | H | trans-4-(methoxymethyl)cyclohexyl | 385.5/4.59 | A |
| 221 | H | H | c-Pr | H | H | trans-4-(methoxymethyl)cyclohexyl | 411.5/4.75 | A |

TABLE 7-continued

| Ex. | R$^{1A}$ | R$^{1B}$ | R$^{1C}$ | R$^{1D}$ | R$^{3A}$ | R$^{3B}$ | (LC-MS: [M + H]$^+$/ Rt (min)) | LC-MS Method |
|---|---|---|---|---|---|---|---|---|
| 222 | H | F | Me | H | H | 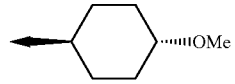 4,4-difluorocyclohexyl | 395/1.051 | F |
| 223 | H | F | Me | H | H | 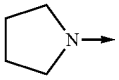 trans-4-methoxycyclohexyl | 389/0.961 | F |
| 224 | H | H |  pyrrolidin-1-yl | H | H | 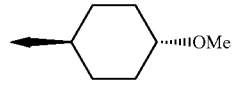 4,4-difluorocyclohexyl | 432/1.52 | E |
| 225 | H | Me | Me | H | H | 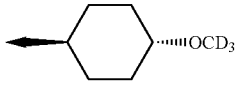 trans-4-methoxycyclohexyl | 385/0.963 | F |
| 226 | H | H | OCF$_3$ | H | H | 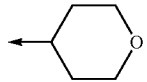 trans-4-(OCD$_3$)cyclohexyl | 444/1.96 | E |
| 227 | H | H | OCF$_3$ | H | H | 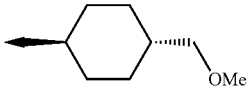 tetrahydropyran-4-yl | 413/1.51 | E |
| 228 | H | H | OCF$_3$ | H | H | 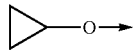 trans-4-(methoxymethyl)cyclohexyl | 455/1.71 | E |
| 229 | H | H | OCF$_3$ | H | H | c-Pen | 397/1.75 | E |
| 230 | H | H |  cyclopropyl-O- | H | H | 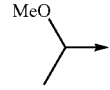 trans-4-methoxycyclohexyl | 413/0.941 | F |
| 231 | H | 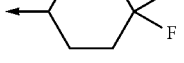 iPrO | H | H | H | 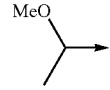 4,4-difluorocyclohexyl | 421/0.980 | F |
| 232 | H | 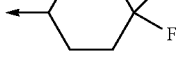 iPrO | Me | H | H | 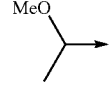 4,4-difluorocyclohexyl | 435/1.035 | F |
| 233 | H | 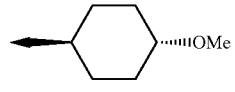 iPrO | Me | H | H | trans-4-methoxycyclohexyl | 429/0.944 | F |

TABLE 7-continued

| Ex. | R¹ᴬ | R¹ᴮ | R¹ᶜ | R¹ᴰ | R³ᴬ | R³ᴮ | (LC-MS: [M + H]⁺/ Rt (min)) | LC-MS Method |
|---|---|---|---|---|---|---|---|---|
| 234 | H | H | OEt | H | H | cyclohexyl-CH₂OMe (trans) | 415/1.90 | E |
| 235 | H | H | OiPr | H | H | cyclohexyl-CH₂OMe (trans) | 429/1.95 | E |
| 236 | H | H | F | H | H | cyclohexyl-CH₂OMe (trans) | 389/1.80 | E |
| 237 | H | H | Cl | H | H | cyclohexyl-CH₂OMe (trans) | 405/2.00 | E |
| 238 | H | H | Br | H | H | cyclohexyl-CH₂OMe (trans) | 450/2.00 | E |
| 239 | H | H | MeO-CH₂CH₂- | H | H | 4,4-difluorocyclohexyl | 421/1.80 | E |
| 240 | Et | H | OMe | H | H | cyclohexyl-OMe (trans) | 415/1.872 | E |
| 241 | Et | H | OMe | H | H | 4,4-difluorocyclohexyl | 421/1.960 | E |
| 242 | Me | H | OMe | H | H | cyclohexyl-OMe (trans) | 401/1.761 | E |
| 243 | Me | H | OMe | H | H | 4,4-difluorocyclohexyl | 407/1.863 | E |
| 244 | Et | H | OMe | H | H | tetrahydropyran-4-yl | 387.0/0.879 | F |
| 245 | H | H | OCH(CH₃)₂-CH₂- (isobutoxy) | H | H | cyclohexyl-OMe (trans) | 415.3/4.52 | A |

TABLE 7-continued

| Ex. | R$^{1A}$ | R$^{1B}$ | R$^{1C}$ | R$^{1D}$ | R$^{3A}$ | R$^{3B}$ | (LC-MS: [M + H]$^+$/ Rt (min)) | LC-MS Method |
|---|---|---|---|---|---|---|---|---|
| 246 | H | H | MeO-cyclopropyl- | H | H | trans-4-methoxycyclohexyl | 427/1.75 | E |
| 247 | H | H | CH(OMe)CH$_3$- | H | H | trans-4-methoxycyclohexyl | 429/1.73 | E |
| 248 | H | H | MeO-cyclopropyl- | H | H | 4,4-difluorocyclohexyl | 433/1.78 | E |
| 249 | H | H | cyclopropyl-O- | H | H | 4,4-difluorocyclohexyl | 419/1.094 | F |
| 250 | H | cyclopropyl-O- | | H | H | 4,4-difluorocyclohexyl | 419/1.075 | F |
| 251 | H | H | CH(OMe)CH$_3$- | H | H | 4,4-difluorocyclohexyl | 435/1.83 | E |
| 252 | H | H | MeOCH$_2$CH(CH$_3$)- | H | H | 4,4-difluorocyclohexyl | 435/1.86 | E |
| 253 | H | OMe | Me | H | H | 4,4-difluorocyclohexyl | 401/1.802 | E |
| 254 | H | OMe | Me | H | H | trans-4-methoxycyclohexyl | 405/1.871 | E |
| 255 | H | OMe | Et | H | H | trans-4-methoxycyclohexyl | 415/1.913 | E |
| 256 | H | OMe | Et | H | H | 4,4-difluorocyclohexyl | 421/1.986 | E |
| 257 | c-Pr | H | OMe | H | H | trans-4-methoxycyclohexyl | 427/0.901 | F |
| 258 | OMe | H | Me | H | H | c-Hex | 371.1/1.75 | B |

TABLE 7-continued
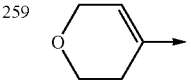
| Ex. | R[1A] | R[1B] | R[1C] | R[1D] | R[3A] | R[3B] | (LC-MS: [M + H]+/ Rt (min)) | LC-MS Method |
|---|---|---|---|---|---|---|---|---|
| 259 | 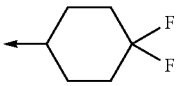 | H | OMe | H | H | 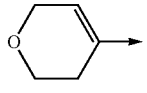 | 475/0.920 | F |
| 260 | 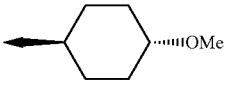 | H | OMe | H | H | 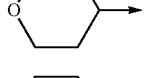 | 469/0.849 | F |
| 261 | 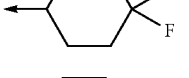 | H | OMe | H | H | 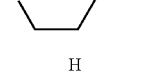 | 477/1.001 | F |
| 262 | 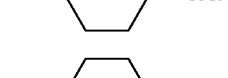 | H | OMe | H | H | 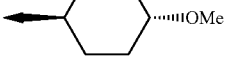 | 471/0.946 | F |
| 263 | H | OMe | c-Pr | H | H | 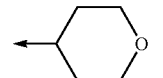 | 427/0.907 | F |
| 264 | OMe | H | OCF$_3$ | H | H | 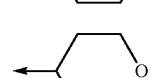 | 443/2.05 | E |
| 265 | OEt | H | OCF$_3$ | H | H | 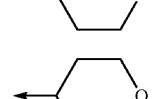 | 457/2.13 | E |
| 266 | OMe | H | CF$_3$ | H | H | 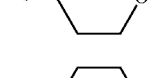 | 427/2.00 | E |
| 267 | OEt | H | CF$_3$ | H | H | 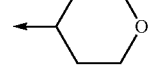 | 441/2.11 | E |
| 268 | H | OMe | Me | H | H | 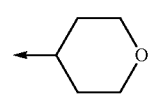 | 373/0.880 | F |
| 269 | H | OEt | Me | H | H |  | 421/1.090 | F |
| 270 | OMe | H | Me | H | H |  | 407.2/1.67 | B |

TABLE 7-continued
| Ex. | $R^{1A}$ | $R^{1B}$ | $R^{1C}$ | $R^{1D}$ | $R^{3A}$ | $R^{3B}$ | (LC-MS: $[M+H]^+$/ Rt (min)) | LC-MS Method |
|---|---|---|---|---|---|---|---|---|
| 271 | H | OEt | Et | H | H | 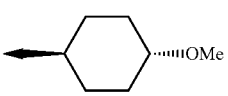 | 435/1.259 | F |
| 272 | H | OEt | Et | H | H | 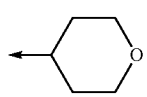 | 429/1.101 | F |
| 273 | H | OEt | Me | H | H | 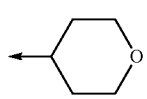 | 387/0.970 | F |
| 274 | H | OEt | Et | H | H | 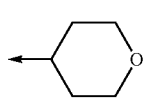 | 401/1.017 | F |
| 275 | H | OMe | Et | H | H | 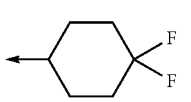 | 387/0.917 | F |
| 276 | H | Me | c-Pr | H | H | 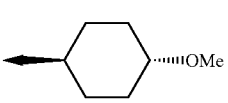 | 417/1.148 | F |
| 277 | H | Me | c-Pr | H | H | 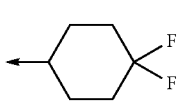 | 411/1.094 | F |
| 278 | H | Me | OMe | H | HF | 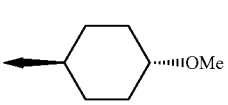 | 407/1.066 | F |
| 279 | H | Me | OMe | H | H | 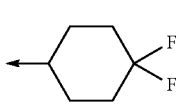 | 401/0.935 | F |
| 280 | H | c-Pr | OMe | H | H | 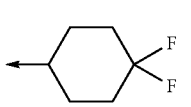 | 433/1.106 | F |
| 281 | H | Me | OEt | H | H | 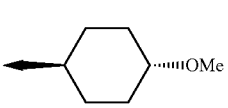 | 421/1.082 | F |
| 282 | H | Me | OEt | H | H |  | 415/1.010 | F |

TABLE 7-continued

| Ex. | R$^{1A}$ | R$^{1B}$ | R$^{1C}$ | R$^{1D}$ | R$^{3A}$ | R$^{3B}$ | (LC-MS: [M + H]$^+$/ Rt (min)) | LC-MS Method |
|---|---|---|---|---|---|---|---|---|
| 283 | H | Me | c-Pr | H | H | tetrahydropyran-4-yl | 383/0.975 | F |
| 284 | H | OMe | Br | H | H | 4,4-difluorocyclohexyl | 472/1.056 | F |
| 285 | H | OMe | Br | H | H | trans-4-methoxycyclohexyl | 466/0.976 | F |
| 286 | H | Me | Br | H | H | 4,4-difluorocyclohexyl | 456/1.131 | F |
| 287 | H | Et | OMe | H | H | 4,4-difluorocyclohexyl | 421/1.117 | F |
| 288 | H | Et | OMe | H | H | trans-4-methoxycyclohexyl | 415/0.965 | F |
| 289 | H | Et | OMe | H | H | tetrahydropyran-4-yl | 387/0.912 | F |
| 290 | H | H | OCHF$_2$ | H | H | 4,4-difluorocyclohexyl | 429/1.000 | F |
| 291 | H | H | OCHF$_2$ | H | H | trans-4-methoxycyclohexyl | 423/0.936 | F |
| 292 | H | H | OCHF$_2$ | H | H | tetrahydropyran-4-yl | 395/0.848 | F |
| 293 | H | Me | OCHF$_2$ | H | H | trans-4-methoxycyclohexyl | 437/0.967 | F |
| 294 | H | Me | OCHF$_2$ | H | H | tetrahydropyran-4-yl | 409/0.894 | F |

TABLE 7-continued
| Ex. | R$^{1A}$ | R$^{1B}$ | R$^{1C}$ | R$^{1D}$ | R$^{3A}$ | R$^{3B}$ | (LC-MS: [M + H]$^+$/ Rt (min)) | LC-MS Method |
|---|---|---|---|---|---|---|---|---|
| 295 | H | H | Me | H | H |  | 374/1.84 | E |
| 296 | H | H | c-Pr | H | H | 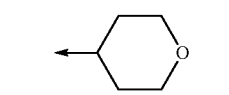 | 400/1.98 | E |
| 297 | H | H | CF$_3$ | H | H | 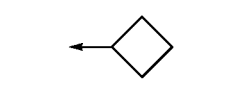 | 397.2/4.62 | A |
| 298 | H | H | CF$_3$ | H | H | 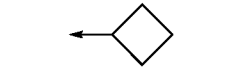 | 367.2/4.82 | A |
| 299 | H | H | OCF$_3$ | H | H | 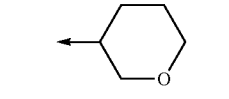 | 383.0/4.91 | A |
| 300 | H | H | OCF$_3$ | H | H | 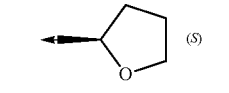 | 413.7/4.79 | A |
| 301 | H | H | OCF$_3$ | H | H | 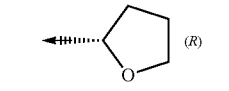 (S) | 399.7/4.67 | A |
| 302 | H | H | H | H | H | 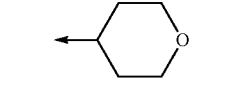 (R) | 399.7/4.69 | A |
| 303 | H | OMe | c-Pr | H | H | 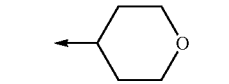 | 399/0.951 | F |
| 304 | H | OCF$_3$ | H | H | H | 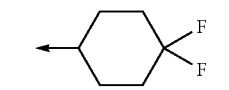 | 413.0/0.971 | F |
| 305 | H | OMe | OMe | H | H |  | 423/0.971 | F |
| 306 | H | OMe | OMe | H | H |  | 417/0.781 | F |

TABLE 7-continued

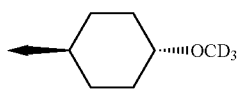

| Ex. | R1A | R1B | R1C | R1D | R3A | R3B | (LC-MS: [M + H]+/ Rt (min)) | LC-MS Method |
|---|---|---|---|---|---|---|---|---|
| 307 | H | Et | H | H | H | 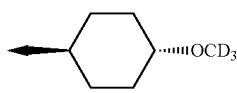 cyclohexyl-OCD3 | 388/1.925 | E |
| 308 | H | H | CD3 | H | H | 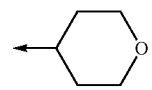 cyclohexyl-OCD3 | 377/1.808 | E |
| 309 | OCD3 | H | CF3 | H | H | tetrahydropyran-4-yl | 430/1.992 | E |
| 310 | OCD3 | H | CF3 | H | H | 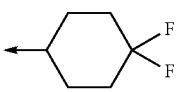 4,4-difluorocyclohexyl | 464/2.150 | E |
| 311 | H | H | CD3 | H | H | 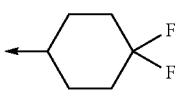 4,4-difluorocyclohexyl | 380/1.850 | E |
| 312 | H | H | CD3 | H | H | 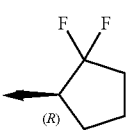 (R)-2,2-difluorocyclopentyl | 380/1.815 | E |
| 313 | H | H | CD3 | H | H | 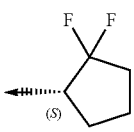 (S)-2,2-difluorocyclopentyl | 380/1.850 | E |
| 314 | H | H | CD3 | H | H |  cyclohexyl-OEt | 388/1.867 | E |
| 315 | H | H | CD3 | H | H | c-Pen | 330/1.858 | E |
| 316 | 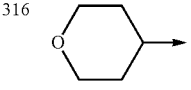 tetrahydropyran-4-yl | H | Me | H | H | 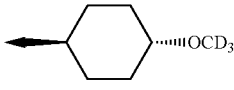 cyclohexyl-OCD3 | 458/1.942 | E |
| 317 | H | OMe | CF3 | H | H | 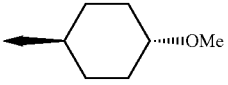 cyclohexyl-OMe | 455/0.867 | F |
| 318 | H | OMe | Et | H | H | 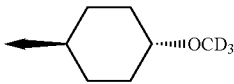 cyclohexyl-OCD3 | 418/1.942 | E |

TABLE 7-continued

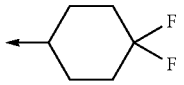

| Ex. | $R^{1A}$ | $R^{1B}$ | $R^{1C}$ | $R^{1D}$ | $R^{3A}$ | $R^{3B}$ | (LC-MS: $[M+H]^+$/ Rt (min)) | LC-MS Method |
|---|---|---|---|---|---|---|---|---|
| 319 | H | H | OCD₃ | H | H | 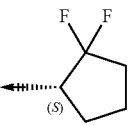 | 396/0.988 | F |
| 320 | H | H | OCD₃ | H | H | 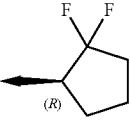 (S) | 396/0.960 | F |
| 321 | H | H | OCD₃ | H | H | 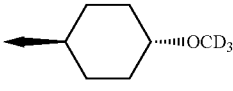 (R) | 396/0.948 | F |
| 322 | H | H | Oc-Pr | H | H | 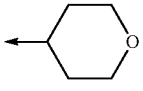 ''''OCD₃ | 416/0.948 | F |
| 323 | H | OCD₃ | c-Pr | H | H |  | 402/0.943 | F |
| 324 | H | H | OCD₃ | H | H | c-Hex | 360/0.976 | F |
| 325 | H | H | Et | H | H | 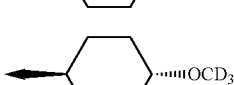 ''''OCD₃ | 388/1.942 | E |
| 326 | H | H | OCHF₂ | H | H | 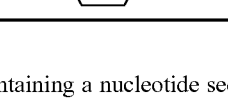 ''''OCD₃ | 426/1.692 | E |

TEST EXAMPLE

Hereinafter, pharmacological test results of the representative compounds of the present invention are demonstrated and pharmacological actions of such compounds are explained, but the present invention should not be limited thereto.

TEST EXAMPLE 1

Evaluation of PAM Activity with Human α7 nACh Receptor Stably Expressing Cells (1) Human α7 nAChR stably expressing cells (cat#CCL-82.2, ATCC, USA) were used as a host cell. PcDNA3.1Zeo Human α7 nAChR stably expressing cells were generated and cultured. In detail, GH4C1 cells derived from rat pituitary vector containing a nucleotide sequence encoding a protein GenBank BAC81731 and pcDNA3.1 vector containing human α7 nAChR gene (cat#V790-20, invitrogen, Carlsbad, Calif., USA) were transfected to the cells to give aequorins and human α7 nAChR stably expressing cells respectively. The aequorins and human α7 nAChR stably expressing cells were screened with Zeocin (cat#R25001, invitrogen, Carlsbad, Calif., USA) and Geneticin (cat#10131-027, invitrogen, Carlsbad, Calif., USA) respectively.

The cells were cultured in F-10 Nutrient Mixture (Ham) medium (cat#11550-043, invitrogen, Carlsbad, Calif., USA) containing 2.5% fetal bovine serum (cat#2917354, ICN Biomedicals, Inc, USA), 15% inactivated horse serum (cat#26050-088, invitrogen, Carlsbad, Calif., USA), 1 μg/mL Geneticin, and 5 μg/mL Puromycin (cat#14861-84, invitrogen, Carlsbad, Calif., USA), in a Collagen Type 1-coated dish (cat#4030-010, iwaki, Tokyo, Japan). During the culture, the medium was replaced with fresh medium in every 2 to 3 days, and the cells were treated with TrypLE Express (cat#45604-021, invitrogen, Carlsbad, Calif., USA) to collect them in every 7 days. Thus, the cells were subcultured.

7 Days after subculturing, the cells were treated with TrypLE Express to collect them when they were about 80% confluent. The cells were suspended in a reaction medium containing Hanks (cat#14065-056, invitrogen, Carlsbad, Calif., USA)/20 mmol/L Hepes (cat#15630-080, invitrogen, Carlsbad, Calif., USA), Buffer (pH 7.4), F-10 Nutrient Mixture (Ham), and 0.1 mg/mL Geneticin, and the suspension was seeded in a 384-well plate (cat#781090, Greiner, Germany) at 20000 cells/25 μL per well.

On the next day after seeding, Viviren (cat#E649X, Promega, Madison, Wis., USA) was added to the medium so that the final concentration could be 4 μmol/L (15 μL/well). The plates were centrifuged and then placed in the dark for 4 hours at room temperature.

(2) Preparation of the Test Samples

Each of the test compounds was dissolved in DMSO to prepare each test sample at a concentration of 1000-fold the final concentration. To the solution was added Hanks/20 mM HEPES/0.2% BSA (cat#A3803, Sigma, St. Louis, Mo., USA), and the concentration was adjusted to 6-fold the final concentration.

(3) Evaluation of PAM Activity

FDSS7000 (Hamamatsu Photonics) was used to detect the luminescence signal evoked by α7 nAChR stimulation. The cells and a luminescent substrate were put on a plate, and the test sample was added thereto. After 150 seconds, ACh whose concentration shows 20% ($EC_{20}$) of the maximal signal was added thereto. After the addition of ACh, the luminescence signal (the central wavelength: 465 nm) was measured for 138 seconds to calculate RLU (Max-Min). The ratio of the RLU (Max-Min) of the test-compound-containing wells to that of the control wells was defined as PAM activity. Table 8 shows α7 PAM activity data of the representative compounds in the present invention.

TABLE 8

| Ex. | α7PAM (%) @ 10 μmol/L |
|---|---|
| 1 | 1209 |
| 2 | 625 |
| 3 | 512 |
| 4 | 2344 |
| 5 | 1368 |
| 6 | 285 |
| 7 | 1044 |
| 8 | 3053 |
| 9 | 332 |
| 10 | 355 |
| 11 | 221 |
| 12 | 231 |
| 13 | 3399 |
| 14 | 728 |
| 15 | 1025 |
| 16 | 1764 |
| 17 | 2469 |
| 18 | 6779 |
| 19 | 306 |
| 20 | 2215 |
| 21 | 523 |
| 22 | 1425 |
| 23 | 6196 |
| 24 | 745 |
| 25 | 253 |
| 26 | 521 |
| 27 | 1673 |
| 28 | 340 |
| 29 | 206 |
| 30 | 908 |
| 31 | 1191 |
| 32 | 430 |
| 33 | 430 |
| 34 | 445 |
| 35 | 411 |
| 36 | 897 |
| 37 | 481 |
| 38 | 1101 |
| 39 | 1892 |
| 40 | 3205 |
| 41 | 3749 |
| 42 | 241 |
| 43 | 528 |
| 44 | 322 |
| 45 | 1576 |
| 46 | 544 |
| 47 | 375 |
| 48 | 1202 |
| 49 | 429 |
| 50 | 219 |
| 51 | 295 |
| 52 | 366 |
| 53 | 309 |
| 54 | 657 |
| 55 | 603 |
| 56 | 676 |
| 57 | 382 |
| 58 | 577 |
| 59 | 433 |
| 60 | 846 |
| 61 | 1092 |
| 62 | 653 |
| 63 | 358 |
| 64 | 1133 |
| 65 | 385 |
| 66 | 466 |
| 67 | 436 |
| 68 | 430 |
| 69 | 242 |
| 70 | 719 |
| 71 | 763 |
| 72 | 158 |
| 73 | 453 |
| 74 | 1226 |
| 75 | 621 |
| 76 | 420 |
| 77 | 1780 |
| 78 | 987 |
| 79 | 1064 |
| 80 | 1033 |
| 81 | 819 |
| 82 | 888 |
| 83 | 420 |
| 84 | 179 |
| 85 | 1081 |
| 86 | 1481 |
| 87 | 514 |
| 88 | 1063 |
| 89 | 1506 |
| 90 | 1467 |
| 91 | 217 |
| 92 | 356 |
| 93 | 934 |
| 94 | 154 |
| 95 | 133 |
| 96 | 143 |
| 97 | 117 |

TABLE 8-continued

| Ex. | α7PAM (%) @ 10 μmol/L |
|---|---|
| 98 | 89 |
| 99 | 755 |
| 100 | 198 |
| 101 | 338 |
| 102 | 228 |
| 103 | 281 |
| 104 | 190 |
| 105 | 338 |
| 106 | 164 |
| 107 | 159 |
| 108 | 207 |
| 109 | 267 |
| 110 | 291 |
| 111 | 410 |
| 112 | 265 |
| 113 | 654 |
| 114 | 189 |
| 115 | 182 |
| 116 | 279 |
| 117 | 209 |
| 118 | 188 |
| 119 | 2154 |
| 120 | 654 |
| 121 | 1601 |
| 122 | 410 |
| 123 | 1445 |
| 124 | 1230 |
| 125 | 119 |
| 126 | 118 |
| 127 | 806 |
| 128 | 429 |
| 129 | 325 |
| 130 | 252 |
| 131 | 107 |
| 132 | 361 |
| 133 | 568 |
| 134 | 237 |
| 135 | 310 |
| 136 | 327 |
| 137 | 328 |
| 138 | 642 |
| 139 | 1018 |
| 140 | 265 |
| 141 | 448 |
| 142 | 238 |
| 143 | 574 |
| 144 | 637 |
| 145 | 804 |
| 146 | 513 |
| 147 | 181 |
| 148 | 412 |
| 149 | 1053 |
| 150 | 643 |
| 151 | 746 |
| 152 | 707 |
| 153 | 386 |
| 154 | 811 |
| 155 | 210 |
| 156 | 358 |
| 157 | 366 |
| 158 | 292 |
| 159 | 187 |
| 160 | 207 |
| 161 | 567 |
| 162 | 1874 |
| 163 | 318 |
| 164 | 979 |
| 165 | 442 |
| 166 | 711 |
| 167 | 434 |
| 168 | 737 |
| 169 | 359 |
| 170 | 1413 |
| 171 | 1382 |
| 172 | 541 |

TABLE 8-continued

| Ex. | α7PAM (%) @ 10 μmol/L |
|---|---|
| 173 | 263 |
| 174 | 186 |
| 175 | 223 |
| 176 | 187 |
| 177 | 712 |
| 178 | 524 |
| 179 | 788 |
| 180 | 274 |
| 181 | 538 |
| 182 | 742 |
| 183 | 342 |
| 184 | 200 |
| 185 | 494 |
| 186 | 389 |
| 187 | 220 |
| 188 | 231 |
| 189 | 257 |
| 190 | 256 |
| 191 | 493 |
| 192 | 699 |
| 193 | 889 |
| 194 | 278 |
| 195 | 232 |
| 196 | 229 |
| 197 | 184 |
| 198 | 268 |
| 199 | 1497 |
| 200 | 471 |
| 201 | 370 |
| 202 | 195 |
| 203 | 271 |
| 204 | 193 |
| 205 | 1187 |
| 206 | 196 |
| 207 | 335 |
| 208 | 328 |
| 209 | 266 |
| 210 | 209 |
| 211 | 1034 |
| 212 | 1184 |
| 213 | 800 |
| 214 | 207 |
| 215 | 851 |
| 216 | 271 |
| 217 | 517 |
| 218 | 648 |
| 219 | 238 |
| 220 | 2160 |
| 221 | 1942 |
| 222 | 638 |
| 223 | 257 |
| 224 | 286 |
| 225 | 480 |
| 226 | 594 |
| 227 | 768 |
| 228 | 276 |
| 229 | 689 |
| 230 | 621 |
| 231 | 647 |
| 232 | 860 |
| 233 | 307 |
| 234 | 824 |
| 235 | 611 |
| 236 | 331 |
| 237 | 832 |
| 238 | 1031 |
| 239 | 485 |
| 240 | 833 |
| 241 | 358 |
| 242 | 901 |
| 243 | 842 |
| 244 | 324 |
| 245 | 182 |
| 246 | 364 |
| 247 | 353 |

TABLE 8-continued

| Ex. | α7PAM (%) @ 10 μmol/L |
|---|---|
| 248 | 851 |
| 249 | 1463 |
| 250 | 1215 |
| 251 | 868 |
| 252 | 364 |
| 253 | 563 |
| 254 | 1238 |
| 255 | 1096 |
| 256 | 1668 |
| 257 | 801 |
| 258 | 941 |
| 259 | 309 |
| 260 | 428 |
| 261 | 924 |
| 262 | 348 |
| 263 | 749 |
| 264 | 263 |
| 265 | 181 |
| 266 | 448 |
| 267 | 292 |
| 268 | 361 |
| 269 | 835 |
| 270 | 364 |
| 271 | 931 |
| 272 | 442 |
| 273 | 341 |
| 274 | 618 |
| 275 | 1093 |
| 276 | 1351 |
| 277 | 729 |
| 278 | 861 |
| 279 | 185 |
| 280 | 299 |
| 281 | 197 |
| 282 | 215 |
| 283 | 845 |
| 284 | 1109 |
| 285 | 293 |
| 286 | 825 |
| 287 | 645 |
| 288 | 218 |
| 289 | 255 |
| 290 | 1173 |
| 291 | 1433 |
| 292 | 413 |
| 293 | 525 |
| 294 | 523 |
| 295 | 1143 |
| 296 | 1268 |
| 297 | 340 |
| 298 | 315 |
| 299 | 302 |
| 300 | 376 |
| 301 | 246 |
| 302 | 389 |
| 303 | 1058 |
| 304 | 380 |
| 305 | 729 |
| 306 | 147 |
| 307 | 464 |
| 308 | 1021 |
| 309 | 406 |
| 310 | 134 |
| 311 | 1393 |
| 312 | 1220 |
| 313 | 1433 |
| 314 | 949 |
| 315 | 825 |
| 316 | 807 |
| 317 | 360 |
| 318 | 1084 |
| 319 | 1337 |
| 320 | 1315 |
| 321 | 994 |
| 322 | 639 |
| 323 | 886 |
| 324 | 1352 |
| 325 | 997 |
| 326 | 1251 |

Table 8 demonstrates that the present compounds have PAM activity for α7 nAChR according to the evaluation test of PAM activity. In particular, the compounds of Examples 4, 8, 13, 17, 18, 20, 23, 40, 41, 119 and 220 show a stronger PAM activity than others.

TEST EXAMPLE 2 hERG Inhibition Test

The hERG (human ether-a-go-go) potassium current in CHO cells which stably express hERG gene was recorded by whole-cell patch clamping technique using an automated patch clamp system, QPatch HT (Sophion Bioscience A/S). Inducing the hERG current, the membrane potential was held at −80 mV in voltage clamp mode, and then depolarized to −50 mV for 20 msec and then +20 mV for 5 sec. Then, the membrane potential was repolarized to −50 mV for 5 sec and the tail current amplitude was measured. The stimulation was given at a frequency of every 15 seconds, and the experiment was carried out at room temperature (22±2° C.) The compound was cumulatively administered to each cell in 4 concentrations, wherein the administration was done over 5 minutes in each concentration. The inhibition percentage of the inhibited current was calculated by comparing the current intensities before and after the compound was given in each concentration. According to Hill equation, each 50% inhibitory concentration was calculated ($IC_{50}$ [μmol/L]). The test solutions used herein were as follows: extracellular solution (mmol/L): 2 $CaCl_2$, 1 $MgCl_2$, 10 HEPES, 4 KCl, 145 NaCl, 10 glucose,
intracellular solution (mmol/L): 5.4 $CaCl_2$, 1.8 $MgCl_2$, 10 HEPES, 31 KOH, 10 EGTA, 120 KCl, 4 ATP The compounds in the Examples were tested according to Test Example 2 (hERG inhibition test), and the test results thereof are shown below.

TABLE 9

| Ex. | $IC_{50}$ (μM) | Ex. | $IC_{50}$ (μM) | Ex. | $IC_{50}$ (μM) | Ex. | $IC_{50}$ (μM) |
|---|---|---|---|---|---|---|---|
| 1 | 84.3 | 63 | >10 | 74 | 13.2 | 258 | 47.3 |

TEST EXAMPLE 3

Reactive Metabolites Test

Among metabolites generated in liver microsomes from the present compound, those which react with dansyl glutathione (dGSH) were detected and quantified. The concentration of the binding compound of metabolite and dansyl glutathione was measured with a UPLC fluorescence detection system (UPLC manufactured by Waters Corporation).

The compounds of the Examples were tested according to Test Example 3 (reactive metabolites test), and the test results thereof are shown below.

TABLE 10

| Ex. | IC$_{50}$ (µM) | Ex. | IC$_{50}$ (µM) | Ex. | IC$_{50}$ (µM) | Ex. | IC$_{50}$ (µM) |
|---|---|---|---|---|---|---|---|
| 1 | n.d. | 63 | n.d. | 74 | n.d. | 163 | n.d. |
| 227 | n.d. | 258 | n.d. | | | | | n.d. = no detection of reactive metabolites

TEST EXAMPLE 4

Rat PK Test

The present compound was administered intravenously in saline solution or orally in methylcellulose solution to 7 weeks old rats, and their blood was collected according to the following schedule:
(intravenous administration) 5 minutes, 15 minutes, 30 minutes, 1 hour, 2 hours, 4 hours, 6 hours and 24 hours after the administration
(oral administration) 15 minutes, 30 minutes, 1 hour, 2 hours, 4 hours, 6 hours and 24 hours after the administration The collected blood was centrifuged at 3000 rpm for 10 minutes in a refrigerated centrifuge set at 4° C. The obtained plasma was measured with a HPLC to give a time curve of plasma level, thereby calculating the pharmacokinetic parameters.

The test herein demonstrated that the present compounds have excellent pharmacokinetics. For example, the compounds in Examples 1, 163 and 227 have a bioavailability of 41%, 41% and 69% respectively.

TEST EXAMPLE 5

Measurement of Protein Binding Ratio

The protein-binding ratio of the present compounds in serum was measured by an equilibrium dialysis method using 96-well Equilibrium Dialyzer MW10K (HARVARD APPARATUS). The human serum used herein was frozen human serum pools (Cosmo Bio, No. 12181201), and the buffer used herein was PBS pH 7.4 (GIBCO, No. 10010-0231).

The test herein demonstrated that the present compounds have a low protein-binding ratio. For example, the compound in Example 1 had a protein binding ratio of 84.7% in the plasma, and that of 91.9% in the brain.

TEST EXAMPLE 6

Measurement of Brain Penetration

The plasma and brain homogenates were deproteinized with methanol and then centrifuged. The supernatant was filtered, and the obtained sample was quantified with LC-MS/MS to calculate the concentration of the plasma and brain.

The test herein demonstrated that the present compounds have an excellent brain-penetration. For example, the concentration ratio of the brain to the plasma was 1.27, 2.01, 1.92 and 1.55 in the compounds of Examples 1, 163, 227 and 258 respectively.

TEST EXAMPLE 7

Evaluation of Cognitive Function with Mice in Novel Object Recognition Test (Hereinafter, Referred to as "mORT")

Slc: ddY mice (25 g to 30 g, male, Japan SLC) can be used in the novel object recognition test wherein the interval between the $1^{st}$ trial (training) and the $2^{nd}$ trial (test) correlates with the memory loss for the objects used in the $1^{st}$ trial, and a significant memory-loss is observed when the $2^{nd}$ trial is performed 24 hours after the $1^{st}$ trial. According to the test mechanism, the present compounds were administered prior to the $1^{st}$ trial, and the enhancement effect on memory in the $2^{nd}$ trial was evaluated.

The test herein demonstrated that the present compounds can exhibit effects of improving cognitive function even with an extremely low dose in a continuous manner. For example, the compound in Example 1 had a minimum effective dose of 0.1 mg/kg, and the efficacy did not decrease at a dose of 0.3 mg/kg, 1.0 mg/Kg or 3 mg/kg. The compound in Example 74 had a minimum effective dose of 0.1 mg/kg, and the efficacy did not decrease at a dose of 0.3 mg/kg, 1.0 mg/kg or 3 mg/kg. Furthermore, the compounds in Example 63 and 66 showed the efficacy at doses of 3 mg/Kg and 1 mg/Kg respectively.

TEST EXAMPLE 8

Evaluation on Improvement Against Cognitive Impairment with Rats in Y-Shaped Maze Test (Hereinafter, Referred to as "Y-Maze Test")

In Y-maze test, 0.6 mg/kg scopolamine HBr (cat#S0929, Sigma Aldrich, Japan) can be subcutaneously administered to Slc: Wistar rats (280 g to 300 g, male, Japan SLC) to cause cognitive impairment and decrease the percentage of alternation behavior. According to the test mechanism, the present compounds were treated prior to the administration of scopolamine, and the improvement effect on cognitive impairment was evaluated.

The test herein demonstrated that the present compounds can exhibit effects of improving cognitive function even with an extremely low dose in a continuous manner. For example, the compound in Example 1 significantly improved cognitive function from a dose of 0.3 mg/kg. The compound in Example 74 significantly improved cognitive function from a dose of 0.3 mg/kg. The compound in Example 63 showed a tendency to improve cognitive function from a dose of 0.3 mg/kg.

INDUSTRIAL APPLICABILITY

As explained above, the compound of Formula (I) or a pharmaceutically acceptable salt thereof has potent modulatory-effects on the activity of α7 nicotinic acetylcholine receptor (α7 nAChR), and is thus useful for treating, for example, diseases associated with cholinergic properties in the central nervous system (CNS) and/or peripheral nervous system (PNS), diseases associated with smooth muscle contraction, endocrine disorders, neurodegenerative disorders, diseases such as inflammation and pain, and diseases associated with withdrawal symptoms caused by addictive drug abuse.

The invention claimed is:
1. A compound of Formula (I):

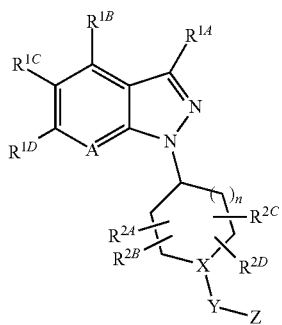

(I)

or a pharmaceutically acceptable salt thereof wherein

A is $CR^{1E}$,

X—Y—Z is N—CO—NR$^{3A}$R$^{3B}$ or N—CO—R$^4$, $R^{1A}$ is a $C_{1-6}$ alkyl optionally substituted with 1 to 5 substituents independently selected from the group consisting of a fluorine atom, a hydroxy group, a $C_{1-6}$ alkoxy, a $C_{3-6}$ cycloalkyl, —NR$^6$R$^7$, —CONR$^6$R$^7$ and —NR$^6$COR$^7$; a $C_{3-10}$ cycloalkyl or a 4- to 10-membered saturated heterocycle, wherein the cycloalkyl and the saturated heterocycle are optionally substituted with 1 to 5 substituents independently selected from the group consisting of a fluorine atom, a hydroxy group, a $C_{1-6}$ alkyl, a $C_{1-6}$ alkoxy and —NR$^6$R$^7$; a $C_{1-6}$ alkoxy optionally substituted with 1 to 5 substituents independently selected from the group consisting of a fluorine atom, a hydroxy group, a $C_{1-6}$ alkoxy, —$NR^6R^7$, —$CONR^6R^7$ and —$NR^6COR^7$; a hydrogen atom; a halogen; —$NR^6R^7$; a cyano group; —$CONR^6R^7$; —$NR^6COR^7$; or —$SO_2R^6$, provided that both $R^6$ and $R^7$ are not a hydrogen atom, $R^{1B}$ to $R^{1E}$ are each independently a $C_{1-6}$ alkyl optionally substituted with 1 to 5 substituents independently selected from the group consisting of a fluorine atom, a hydroxy group, a $C_{1-6}$ alkoxy, a $C_{3-6}$ cycloalkyl, —$NR^6R^{7'}$, —$CONR^6R^{7'}$ and —$NR^6COR^{7'}$; a $C_{3-10}$ cycloalkyl or a 4- to 10-membered saturated heterocycle, wherein the cycloalkyl and the saturated heterocycle are optionally substituted with 1 to 5 substituents independently selected from the group consisting of a fluorine atom, a hydroxy group, a $C_{1-6}$ alkyl, a $C_{1-6}$ alkoxy, —$NR^6R^{7'}$, —$CONR^6R^{7'}$ and —$NR^6COR^{7'}$; a $C_{1-6}$ alkoxy or a $C_{3-10}$ cycloalkoxy, wherein the alkoxy and the cycloalkoxy are optionally substituted with 1 to 5 substituents independently selected from the group consisting of a fluorine atom, a hydroxy group, a $C_{1-6}$ alkoxy, —$CONR^6R^{7'}$ and —$NR^6COR^{7'}$; a hydrogen atom; a hydroxy group; a halogen; an aryl or a heteroaryl, wherein the aryl and the heteroaryl are optionally substituted with 1 to 5 substituents independently selected from the group consisting of a halogen, a hydroxy group, a $C_{1-6}$ alkyl optionally substituted with 1 to 5 fluorine atoms, a $C_{1-6}$ alkoxy, —$NR^6R^{7'}$, —$CONR^6R^{7'}$ and —$NR^6COR^{7'}$; —$NR^6R^{7'}$; a cyano group; —$CONR^6R^{7'}$; —$NR^6COR^{7'}$; or —$SO_2R^{6'}$, provided that both $R^{6'}$ and $R^{7'}$ are not a hydrogen atom, $R^{2A}$ to $R^{2D}$ are each independently a $C_{1-6}$ alkyl optionally substituted with 1 to 5 substituents independently selected from the group consisting of a halogen, a hydroxy group, a $C_{1-6}$ alkoxy and —$NR^8R^9$; a hydrogen atom; a halogen; a hydroxy group; or a $C_{1-6}$ alkoxy optionally substituted with 1 to 5 fluorine atoms, or when two of $R^{2A}$ to $R^{2D}$ are a $C_{1-6}$ alkyl, they may be taken together to form a 4- to 10-membered saturated carbocyclic ring optionally substituted with 1 to 5 substituents independently selected from the group consisting of a fluorine atom, a hydroxy group, a $C_{1-6}$ alkyl, a $C_{1-6}$ alkoxy and —$NR^8R^9$, $R^{3A}$, $R^{3B}$ and $R^4$ are each independently a $C_{1-10}$ alkyl optionally substituted with 1 to 5 substituents independently selected from the group consisting of phenyl, a monocyclic heteroaryl, a 4- to 10-membered saturated heterocycle, a $C_{3-10}$ cycloalkyl, a fluorine atom, a hydroxy group, a $C_{1-6}$ alkoxy optionally substituted with 1 to 5 fluorine atoms, and —$NR^{10}R^{11}$; a $C_{3-10}$ cycloalkyl; a 4- to 10-membered saturated heterocycle; phenyl; a monocyclic heteroaryl; or a hydrogen atom, wherein the cycloalkyl, the saturated heterocycle, the phenyl and the monocyclic heteroaryl may be optionally substituted with 1 to 5 substituents independently selected from the group consisting of an aryl optionally substituted with 1 to 5 substituents independently selected from the group consisting of a fluorine atom, a $C_{1-6}$ alkoxy and —$NR^{10}R^{11}$, a halogen, a hydroxy group, a $C_{1-6}$ alkyl optionally substituted with 1 to 5 substituents independently selected from the group consisting of a fluorine atom, a $C_{1-6}$ alkoxy and —$NR^{10}R^{11}$, a $C_{1-6}$ alkoxy optionally substituted with 1 to 5 substituents independently selected from the group consisting of a $C_{3-6}$ cycloalkyl, a $C_{3-6}$ cycloalkyl-$C_{1-6}$ alkyl, a $C_{1-6}$ alkoxy and a fluorine atom, a $C_{1-6}$ alkylcarbonyl, and —$NR^{10}R^{11}$, provided that (1) $R^{3A}$ and $R^{3B}$ may be taken together to form a 4- to 10-membered saturated heterocycle optionally substituted with 1 to 5 substituents independently selected from the group consisting of a fluorine atom, a hydroxy group, a $C_{1-6}$ alkyl, a $C_{1-6}$ alkoxy and —$NR^{10}R^{11}$, (2) only one of $R^{3A}$ and $R^{3B}$ can be a hydrogen atom, and (3) $R^4$ is not a hydrogen atom, $R^6$ to $R^{11}$, $R^{6'}$ and $R^{7'}$ are the same or different and are a hydrogen atom or a $C_{1-6}$ alkyl optionally substituted with 1 to 5 fluorine atoms, provided that in each combination of $R^6$-$R^7$, $R^{6'}$-$R^{7'}$, $R^8$-$R^9$, and $R^{10}$-$R^{11}$, (1) when one is a hydrogen atom, the other one is not a hydrogen atom, and (2) each combination may be taken together to form a 4- to 10-membered saturated heterocycle optionally substituted with 1 to 5 substituents independently selected from the group consisting of a fluorine atom, a hydroxy group, a $C_{1-6}$ alkyl, a $C_{1-6}$ alkoxy and —$NR^6R^7$, and n is 1.

2. The compound of claim 1 or a pharmaceutically acceptable salt thereof wherein either $R^{3A}$ or $R^{3B}$ is a hydrogen atom.

3. The compound of claim 1 or a pharmaceutically acceptable salt thereof wherein $R^{2A}$ to $R^{2D}$ are each independently a $C_{1-6}$ alkyl optionally substituted with 1 to 5 fluorine atoms; a $C_{1-6}$ alkoxy; a hydrogen atom; or a fluorine atom.

4. The compound of claim 1 or a pharmaceutically acceptable salt thereof wherein $R^{3A}$, $R^{3B}$ and $R^4$ are each independently a $C_{1-10}$ alkyl optionally substituted with 1 to 5 substituents independently selected from the group consisting of a 4- to 10-membered saturated heterocycle, a $C_{3-10}$ cycloalkyl, a fluorine atom, a hydroxy group, a $C_{1-6}$ alkoxy optionally substituted with 1 to 5 fluorine atoms and —$NR^{10}R^{11}$; $C_{3-10}$ cycloalkyl; a 4- to 10-membered saturated heterocycle; a nitrogen-containing monocyclic heteroaryl; or a hydrogen atom, wherein the cycloalkyl, the saturated heterocycle and the nitrogen-containing monocyclic heteroaryl may be optionally substituted with 1 to 5 substituents independently selected from the group consisting of a fluorine atom, a hydroxy group, a $C_{1-6}$ alkyl optionally substituted with 1 to 5 substituents independently selected from the group consisting of a fluorine atom, a $C_{1-6}$ alkoxy and —$NR^{10}R^{11}$, a $C_{1-6}$ alkoxy optionally substituted with a $C_{3-6}$ cycloalkyl or 1 to 5 fluorine atoms and —$NR^{10}R^{11}$, provided that (1) $R^{3A}$ and $R^{3B}$ may be taken together to form a 4- to 10-membered nitrogen-containing saturated heterocycle optionally substituted with 1 to 5 substituents independently selected from the group consisting of a fluorine atom, a hydroxy group, a $C_{1-6}$ alkyl, a $C_{1-6}$ alkoxy and —$NR^{10}R^{11}$, (2) only one of $R^{3A}$ and $R^{3B}$ can be a hydrogen atom, and (3) $R^4$ is not a hydrogen atom.

5. The compound of claim 1 or a pharmaceutically acceptable salt thereof wherein $R^{1A}$ to $R^{1E}$ are each independently a $C_{1-6}$ alkyl optionally substituted with 1 to 5 substituents independently selected from the group consisting of a fluorine atom, a $C_{3-6}$ cycloalkyl, a hydroxy group and a $C_{1-6}$ alkoxy; a $C_{3-8}$ cycloalkyl optionally substituted with 1 to 5 substituents independently selected from the group consisting of a fluorine atom, a hydroxy group, a $C_{1-6}$ alkyl and a $C_{1-6}$ alkoxy; a $C_{1-6}$ alkoxy optionally substituted with 1 to 5 substituents independently selected from the group consisting of a fluorine atom, a hydroxy group and a $C_{1-6}$ alkoxy; a hydrogen atom; a halogen; or a 4- to 10-membered saturated heterocycle optionally substituted with a $C_{1-6}$ alkyl.

6. The compound of claim 1 or a pharmaceutically acceptable salt thereof wherein $R^{3A}$, $R^{3B}$ and $R^4$ are each independently a $C_{1-10}$ alkyl optionally substituted with 1 to 5 substituents independently selected from the group consisting of a fluorine atom and a $C_{1-6}$ alkoxy optionally substituted with 1 to 5 fluorine atoms; a $C_{3-10}$ cycloalkyl; a 4- to 10-membered saturated heterocycle; or a hydrogen atom, wherein the cycloalkyl and the saturated heterocycle are each optionally substituted with 1 to 5 substituents independently selected from the group consisting of a fluorine atom, a $C_{1-6}$ alkyl optionally substituted with 1 to 5 substituents independently selected from the group consisting of a fluorine atom and a $C_{1-6}$ alkoxy, and a $C_{1-6}$ alkoxy optionally substituted with 1 to 5 fluorine atoms, provided that (1) only one of $R^{3A}$ and $R^{3B}$ can be a hydrogen atom, and (2) $R^4$ is not a hydrogen atom.

7. The compound of claim 1 or a pharmaceutically acceptable salt thereof wherein $R^{1A}$ to $R^{1E}$ are each independently a $C_{1-6}$ alkyl optionally substituted with 1 to 5 substituents independently selected from the group consisting of a fluorine atom and a $C_{1-6}$ alkoxy; a $C_{3-8}$ cycloalkyl optionally substituted with 1 to 5 substituents independently selected from the group consisting of a fluorine atom, a $C_{1-6}$ alkyl and a $C_{1-6}$ alkoxy; a $C_{1-6}$ alkoxy optionally substituted with 1 to 5 substituents independently selected from the group consisting of a fluorine atom and a $C_{1-6}$ alkoxy; a hydrogen atom; or a halogen.

8. The compound of claim 1 or a pharmaceutically acceptable salt thereof wherein X—Y—Z is N—CO—NR$^{3A}$R$^{3B}$.

9. The compound of claim 1 selected from the group consisting of:
N-(trans-4-methoxycyclohexyl)-4-(5-methyl-1H-indazol-1-yl)piperidine-1-carboxamide,
4-(3-ethoxy-5-ethyl-1H-indazol-1-yl)-N-(tetrahydro-2H-pyran-4-yl)piperidine-1-carboxamide,
(4,4-difluorocyclohexyl)(4-(5-ethoxy-1H-indazol-1-yl)piperidin-1-yl)methanone,
N-cyclohexyl-4-(5-methyl-1H-indazol-1-yl)piperidine-1-carboxamide,
N-(4,4-difluorocyclohexyl)-4-(5-methyl-1H-indazol-1-yl)piperidine-1-carboxamide,
4-(5-propyl-1H-indazol-1-yl)-N-(tetrahydro-2H-pyran-4-yl)piperidine-1-carboxamide,
4-(5-ethyl-1H-indazol-1-yl)-N-(trans-4-methoxycyclohexyl)piperidine-1-carboxamide,
N-cyclohexyl-4-(5-ethoxy-1H-indazol-1-yl)piperidine-1-carboxamide,
4-(5-ethyl-1H-indazol-1-yl)-N-(tetrahydro-2H-pyran-3-yl)piperidine-1-carboxamide,
N-(4,4-difluorocyclohexyl)-4-(5-ethoxy-1H-indazol-1-yl)piperidine-1-carboxamide,
N-(4,4-difluorocyclohexyl)-4-(5-fluoro-1H-indazol-1-yl)piperidine-1-carboxamide,
4-(5-chloro-1H-indazol-1-yl)-N-cyclopentylpiperidine-1-carboxamide,
4-(5-chloro-1H-indazol-1-yl)-N-(4,4-difluorocyclohexyl)piperidine-1-carboxamide,
N-(4,4-difluorocyclohexyl)-4-(3-(methoxymethyl)-5-methyl-1H-indazol-1-yl)piperidine-1-carboxamide,
N-(4,4-difluorocyclohexyl)-4-(5-methoxy-1H-indazol-1-yl)piperidine-1-carboxamide,
N-(4,4-difluorocyclohexyl)-4-(3-ethyl-5-methyl-1H-indazol-1-yl)piperidine-1-carboxamide,
N-(4,4-difluorocyclohexyl)-4-(3,5-dimethyl-1H-indazol-1-yl)piperidine-1-carboxamide,
N-(4,4-difluorocyclohexyl)-4-(5-isopropoxy-1H-indazol-1-yl)piperidine-1-carboxamide,
N-cyclohexyl-4-(5-isopropoxy-1H-indazol-1-yl)piperidine-1-carboxamide,
N-(4,4-difluorocyclohexyl)-4-(5-methyl-3-(tetrahydro-2H-pyran-4-yl)-1H-indazol-1-yl)piperidine-1-carboxamide,
4-(5-ethyl-3-isopropoxy-1H-indazol-1-yl)-N-(tetrahydro-2H-pyran-4-yl)piperidine-1-carboxamide,
N-(4,4-difluorocyclohexyl)-4-(4-ethyl-1H-indazol-1-yl)piperidine-1-carboxamide,
4-(4-ethyl-1H-indazol-1-yl)-N-(trans-4-methoxycyclohexyl)piperidine-1-carboxamide,
N-(4,4-difluorocyclohexyl)-4-(5-(4-fluorophenyl)-1H-indazol-1-yl)piperidine-1-carboxamide,
4-(5-cyclopropyl-1H-indazol-1-yl)-N-(trans-4-methoxycyclohexyl)piperidine-1-carboxamide,
(R)—N-(2,2-difluorocyclohexyl)-4-(5-methyl-1H-indazol-1-yl)piperidine-1-carboxamide,
(S)—N-(2,2-difluorocyclohexyl)-4-(5-methyl-1H-indazol-1-yl)piperidine-1-carboxamide,
(S)—N-(2,2-difluorocyclopentyl)-4-(5-methyl-1H-indazol-1-yl)piperidine-1-carboxamide,
(R)—N-(2,2-difluorocyclopentyl)-4-(5-methyl-1H-indazol-1-yl)piperidine-1-carboxamide,
N-(trans-4-ethoxycyclohexyl)-4-(5-methyl-1H-indazol-1-yl)piperidine-1-carboxamide, and
(4-(5-isobutyl-1H-indazol-1-yl)piperidin-1-yl)(tetrahydro-2H-pyran-4-yl)methanone,
or a pharmaceutically acceptable salt thereof.

10. The compound of claim 1 selected from the group consisting of:
N-(trans-4-methoxycyclohexyl)-4-(5-methyl-1H-indazol-1-yl)piperidine-1-carboxamide,
(4,4-difluorocyclohexyl)(4-(5-ethoxy-1H-indazol-1-yl)piperidin-1-yl)methanone,
N-(4,4-difluorocyclohexyl)-4-(5-methyl-1H-indazol-1-yl)piperidine-1-carboxamide,
4-(5-ethyl-1H-indazol-1-yl)-N-(trans-4-methoxycyclohexyl)piperidine-1-carboxamide,
4-(5-ethyl-3-isopropoxy-1H-indazol-1-yl)-N-(tetrahydro-2H-pyran-4-yl)piperidine-1-carboxamide,
4-(4-ethyl-1H-indazol-1-yl)-N-(trans-4-methoxycyclohexyl)piperidine-1-carboxamide,
4-(5-cyclopropyl-1H-indazol-1-yl)-N-(trans-4-methoxycyclohexyl)piperidine-1-carboxamide, and
N-(trans-4-ethoxycyclohexyl)-4-(5-methyl-1H-indazol-1-yl)piperidine-1-carboxamide, or a pharmaceutically acceptable salt thereof.

11. A pharmaceutical composition comprising a compound of claim 1 or a pharmaceutically acceptable salt thereof.

12. A method for treating cognitive impairment associated with schizophrenia (CIAS), which comprises administering a therapeutically effective amount of a compound of claim 1 or a pharmaceutically acceptable salt thereof to a patient in need thereof.

* * * * *